United States Patent
Druyor-Sanchez et al.

(10) Patent No.: US 8,609,023 B1
(45) Date of Patent: Dec. 17, 2013

(54) MEMORY MANAGEMENT METHOD AND APPARATUS FOR AUTOMATED BIOLOGICAL REACTION SYSTEM

(75) Inventors: Bobbi Druyor-Sanchez, Tucson, AZ (US); Anthony Ford, Tucson, AZ (US); Bronwen Heilman, Tucson, AZ (US); Darin McDaniel, Tucson, AZ (US); Brian McGraw, Tucson, AZ (US); Stephen Mead, Tucson, AZ (US); William Richards, Tucson, AZ (US); Wayne Showalter, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 09/571,989

(22) Filed: May 16, 2000

Related U.S. Application Data

(60) Division of application No. 09/469,601, filed on Dec. 21, 1999, now abandoned, which is a continuation of application No. 08/909,335, filed on Aug. 11, 1997, now Pat. No. 6,093,574.

(51) Int. Cl.
*G01N 21/00* (2006.01)

(52) U.S. Cl.
USPC ............ 422/63; 422/64; 422/67; 422/68.1; 436/43; 436/50; 436/180

(58) Field of Classification Search
USPC ............ 707/3, 109.1; 235/375; 700/17, 213, 700/266; 705/27, 28; 422/63, 67
See application file for complete search history.

(56) References Cited

U.S. PATENT DOCUMENTS

| 2,234,079 A | 3/1941 | Miller |
| 3,650,437 A | 3/1972 | Binnings et al. |

(Continued)

FOREIGN PATENT DOCUMENTS

| CA | 2 531 690 | 1/2005 | ............ G01N 35/00 |
| CA | 2 532 790 | 1/2005 | ............ G01N 35/02 |

(Continued)

OTHER PUBLICATIONS

Vernay Umbrella Check Valves, Vernay Laboratories, Inc. 1995.

(Continued)

*Primary Examiner* — Brian R Gordon
(74) *Attorney, Agent, or Firm* — Muirhead and Saturnelli, LLC

(57) ABSTRACT

A method and apparatus for an automated biological reaction system is provided. In the processing of a biological reaction system, there is a need for consistently placing an amount of liquid on a slide. In order to accomplish this, several methods are used including a consistency pulse and a volume adjust means. Moreover, in order to reliably operate an automated biological reaction system, the dispenser must be reliable, easy to assemble and accurate. Among other things, in order to accomplish this, the dispense chamber is substantially in line with the reservoir chamber, the reservoir chamber piston is removed, and the flow of liquid through the dispenser is simplified. Further, in order to operate the automated biological reaction system more reliably, the system is designed in modular pieces with higher functions performed by a host device and the execution of the staining operations performed by remote devices. Also, to reliably catalog data which is used by the automated biological reaction system, data is loaded to a memory device, which in turn is used by the operator to update the operator's databases. The generation of the sequence of steps for the automated biological reaction device based on data loaded by the operator, including checks to determine the ability to complete the run, is provided.

5 Claims, 42 Drawing Sheets

(56) References Cited

U.S. PATENT DOCUMENTS

| | | | |
|---|---|---|---|
| 3,695,281 A | 10/1972 | Leon | |
| 3,854,703 A | 12/1974 | Gibbs et al. | |
| 4,362,977 A | 12/1982 | Evans et al. | |
| 4,455,280 A | 6/1984 | Shinohara et al. | |
| 4,835,372 A * | 5/1989 | Gombrich et al. | 235/375 |
| 4,953,075 A * | 8/1990 | Nau et al. | 700/17 |
| 4,964,544 A | 10/1990 | Hanna et al. | |
| 4,971,913 A | 11/1990 | Manabe et al. | |
| 5,009,185 A | 4/1991 | Stokes et al. | |
| 5,232,664 A | 8/1993 | Krawzak et al. | |
| 5,289,385 A | 2/1994 | Grandone et al. | |
| 5,314,825 A | 5/1994 | Weyrauch et al. | |
| 5,316,726 A | 5/1994 | Babson et al. | |
| 5,348,705 A | 9/1994 | Koreyasu et al. | |
| 5,373,972 A | 12/1994 | Bystrom et al. | |
| 5,417,356 A | 5/1995 | Franklin et al. | |
| 5,425,918 A | 6/1995 | Healey et al. | |
| 5,428,470 A | 6/1995 | Labriola, II | |
| 5,431,309 A | 7/1995 | Ophardt | |
| 5,439,646 A | 8/1995 | Tanimizu et al. | |
| 5,439,649 A | 8/1995 | Tseung et al. | |
| 5,443,791 A | 8/1995 | Cathcart et al. | |
| 5,445,288 A | 8/1995 | Banks | |
| 5,446,652 A | 8/1995 | Peterson et al. | |
| 5,468,388 A | 11/1995 | Goddard et al. | |
| 5,474,541 A | 12/1995 | Ritsky et al. | |
| 5,474,744 A | 12/1995 | Lerch | |
| 5,573,727 A | 11/1996 | Keefe et al. | |
| 5,595,326 A | 1/1997 | Bougamont et al. | |
| 5,595,707 A | 1/1997 | Copeland et al. | |
| 5,650,327 A | 7/1997 | Copeland et al. | |
| 5,654,199 A | 8/1997 | Copeland et al. | |
| 5,654,200 A | 8/1997 | Copeland et al. | |
| 5,687,882 A | 11/1997 | Mueller | |
| 5,690,892 A * | 11/1997 | Babler et al. | 422/63 |
| 5,695,718 A | 12/1997 | Imai et al. | |
| 5,712,989 A * | 1/1998 | Johnson et al. | 705/28 |
| 5,851,488 A * | 12/1998 | Saul et al. | 422/67 |
| 5,860,456 A | 1/1999 | Bydlon et al. | |
| 5,862,934 A | 1/1999 | Sattler et al. | |
| 5,961,492 A | 10/1999 | Kriesel et al. | |
| 5,961,923 A * | 10/1999 | Nova et al. | 506/4 |
| 5,988,857 A * | 11/1999 | Ozawa et al. | 700/213 |
| 6,045,759 A | 4/2000 | Ford et al. | |
| 6,093,474 A | 7/2000 | Sironi | |
| 6,093,574 A | 7/2000 | Druyor-Sanchez et al. | |
| 6,097,995 A * | 8/2000 | Tipton et al. | 700/266 |
| 6,192,945 B1 | 2/2001 | Ford et al. | 141/2 |
| 6,199,766 B1 | 3/2001 | Fox et al. | |
| 6,245,041 B1 | 6/2001 | Kriesel | |
| 6,416,713 B1 | 7/2002 | Ford et al. | |
| 6,623,631 B1 | 9/2003 | Graus et al. | |
| 6,685,884 B2 * | 2/2004 | Stylli et al. | 422/63 |
| 6,945,128 B2 | 9/2005 | Ford et al. | |
| 6,998,270 B2 | 2/2006 | Tseung et al. | 436/46 |
| 7,378,058 B2 | 5/2008 | Lemme et al. | |
| 8,137,619 B2 * | 3/2012 | Ford et al. | 422/63 |
| 2004/0100415 A1 | 5/2004 | Veitch et al. | 343/850 |
| 2004/0185481 A1 | 9/2004 | Numajiri | |
| 2005/0135972 A1 | 6/2005 | Lemme et al. | |
| 2005/0159982 A1 | 7/2005 | Showalter et al. | 705/2 |
| 2005/0205673 A1 | 9/2005 | Morris et al. | 235/385 |
| 2006/0190185 A1 | 8/2006 | Ford et al. | 702/19 |
| 2011/0223682 A1 * | 9/2011 | Wakamiya | 436/180 |

FOREIGN PATENT DOCUMENTS

| | | | |
|---|---|---|---|
| EP | 1 333 287 | 8/2003 | G01N 35/10 |
| FR | 2 541 244 | 8/1984 | |
| JP | 2001-512823 | 8/2001 | |
| JP | 2003-248005 | 9/2003 | |
| JP | 2004-239766 | 8/2004 | |
| JP | Hei/05-504627 | 2/2005 | |
| JP | 2005-257548 | 9/2005 | |
| JP | Hei/08-058792 | 3/2006 | |
| SU | 777440 | 12/1980 | |
| WO | WO 92/04004 | 3/1992 | |
| WO | WO99/08090 | 2/1999 | |
| WO | WO 01/54813 | 8/2001 | |
| WO | WO 03/061453 | 7/2003 | |
| WO | WO 03/064670 | 8/2003 | |
| WO | WO 2004/074845 | 9/2004 | G01N 35/00 |

OTHER PUBLICATIONS

European Search Report, 7 pgs.
U.S. Appl. No. 09/571,989, filed May 16, 2000, Druyor-Sanchez et al.
Canadian Office Action dated Nov. 1, 2007 for Application No. 2,560,628.

* cited by examiner

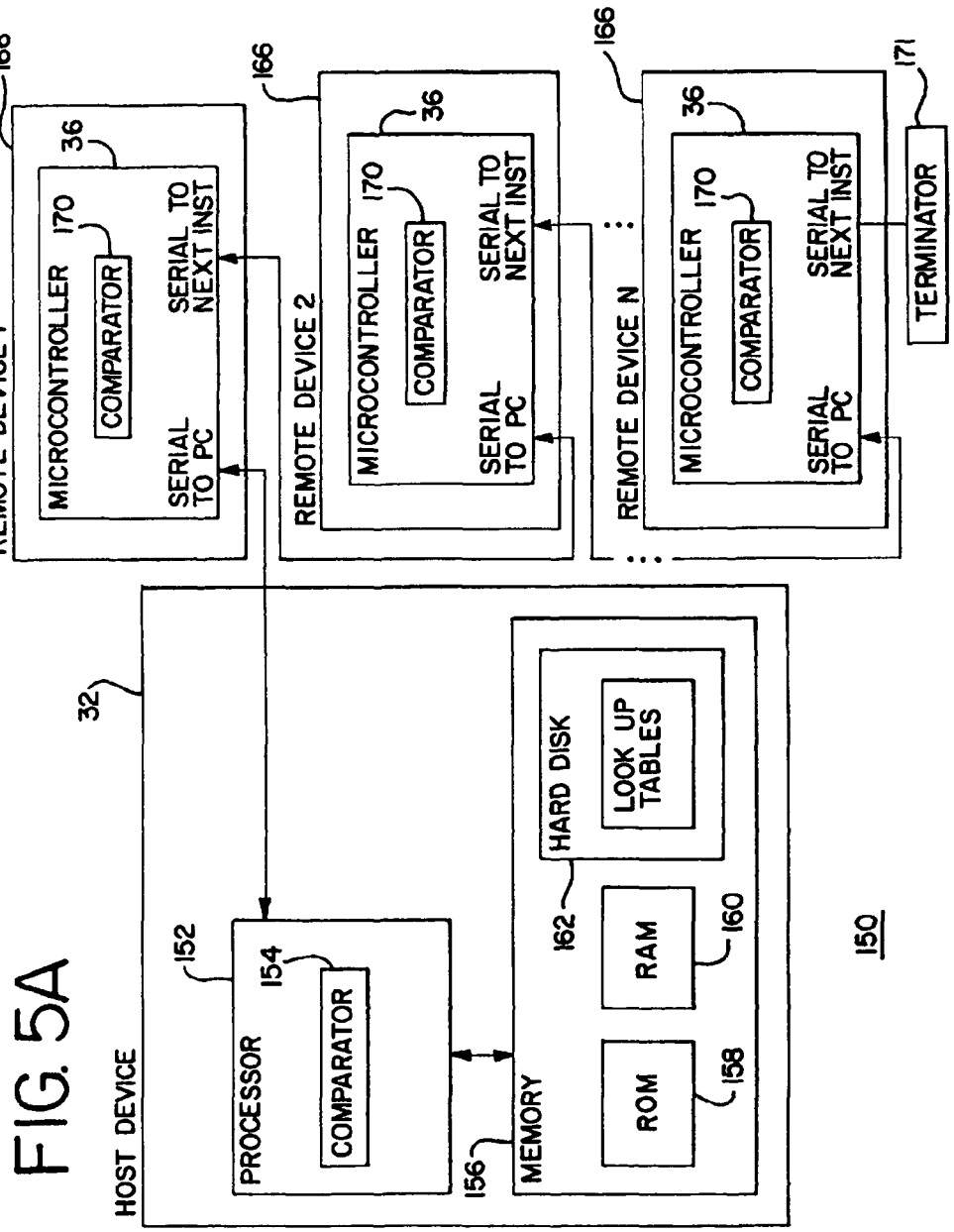

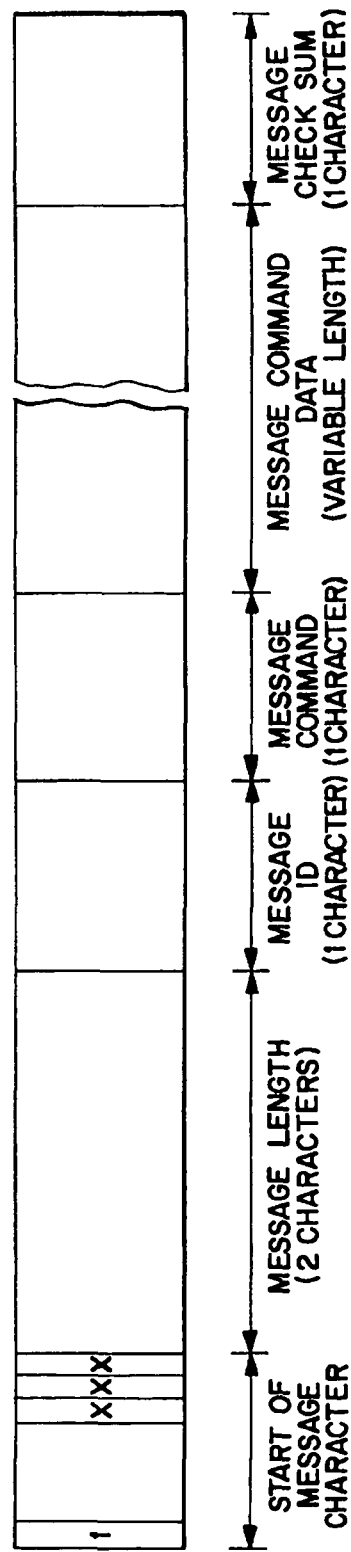

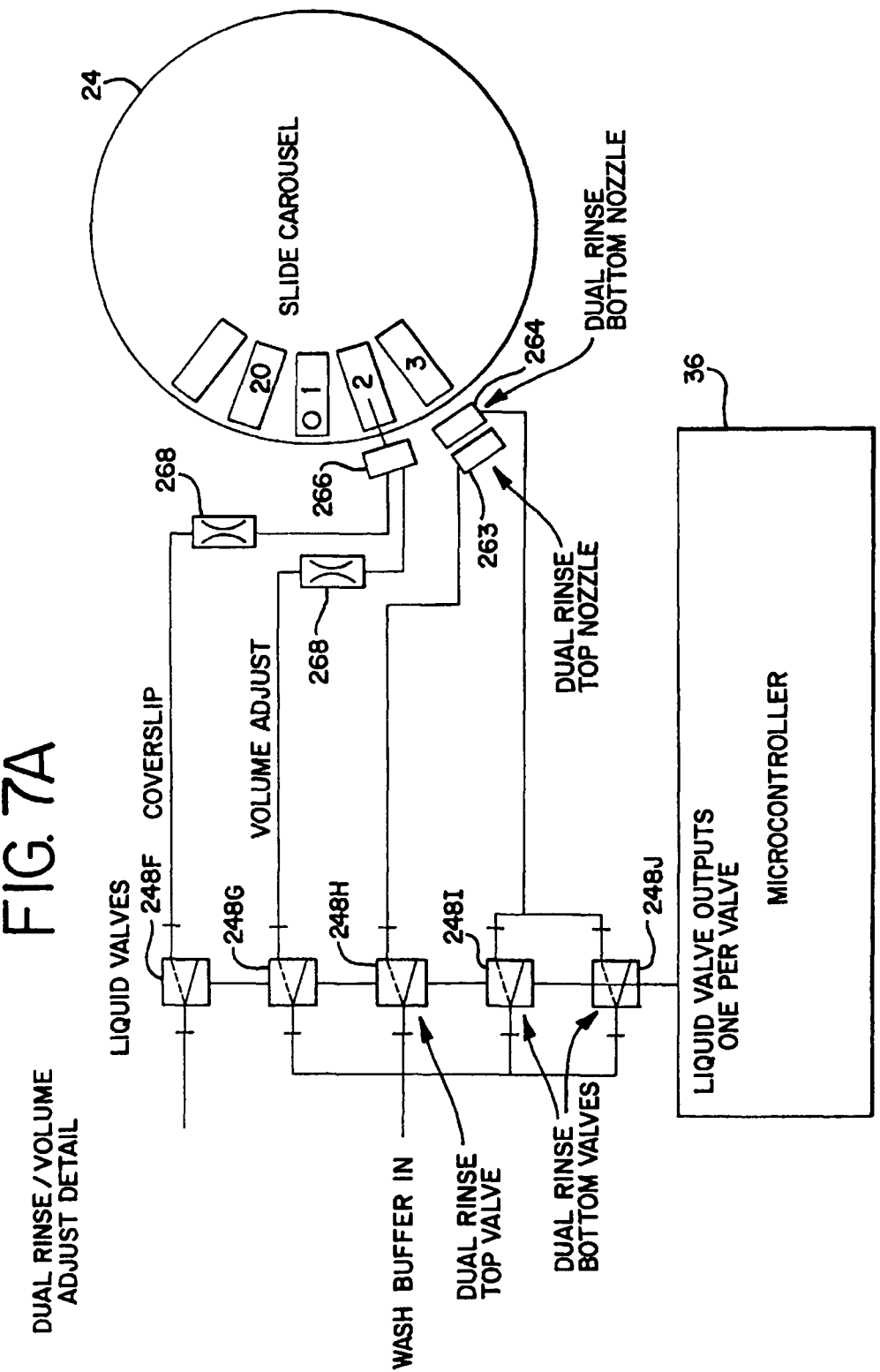

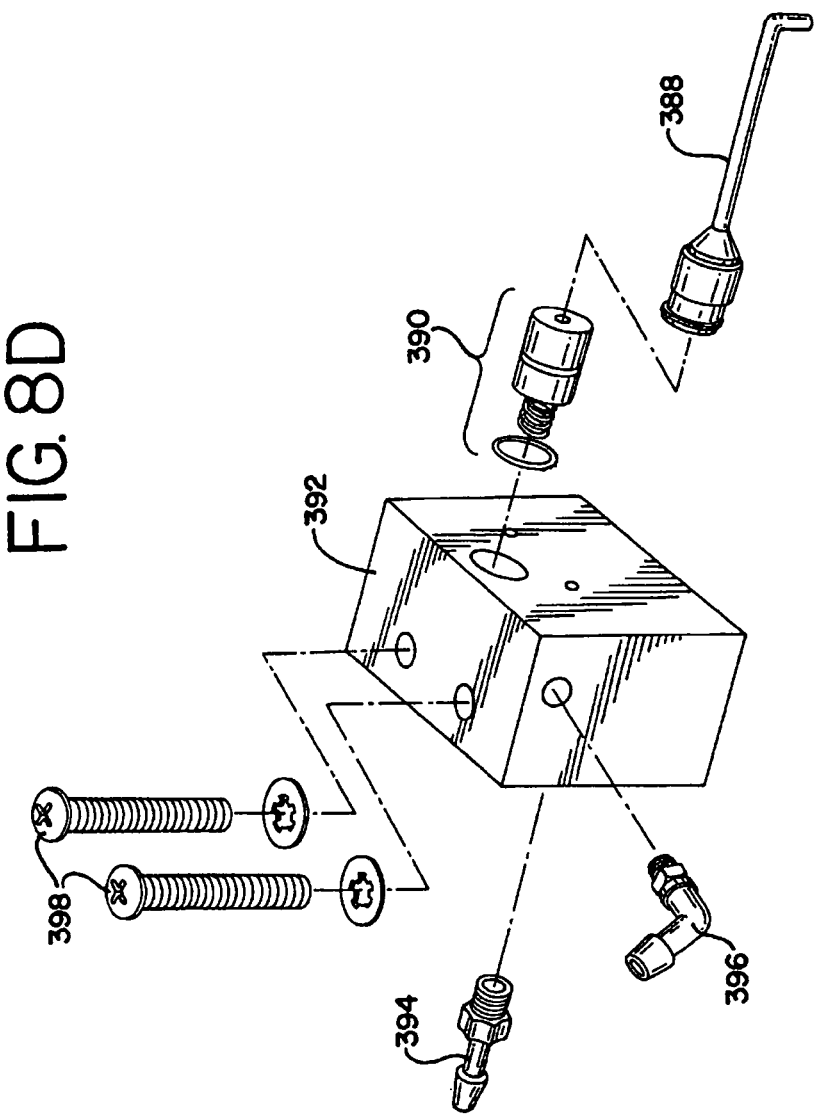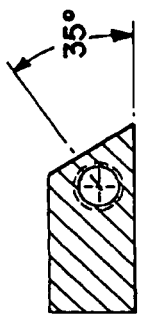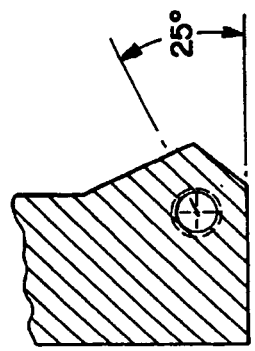

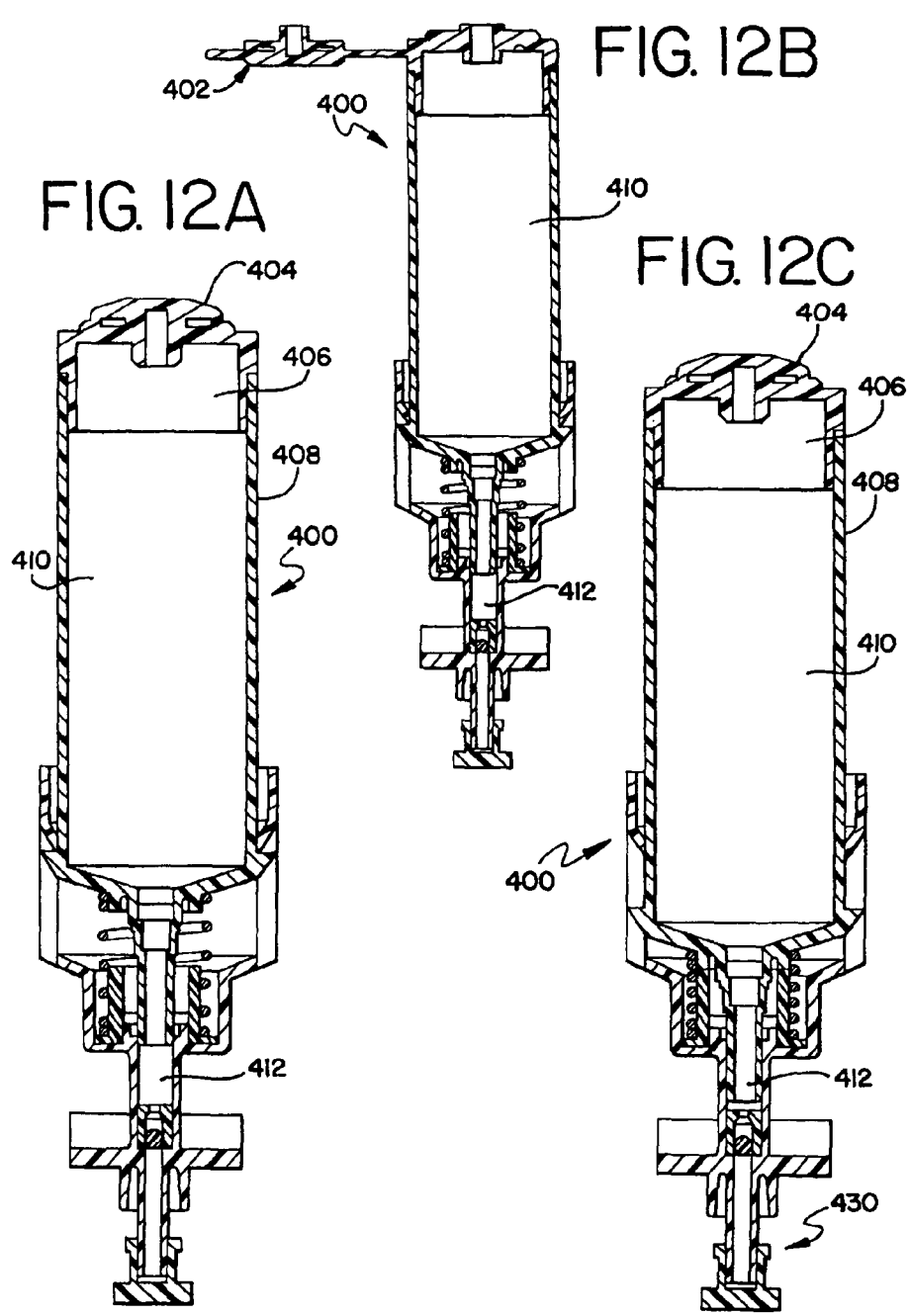

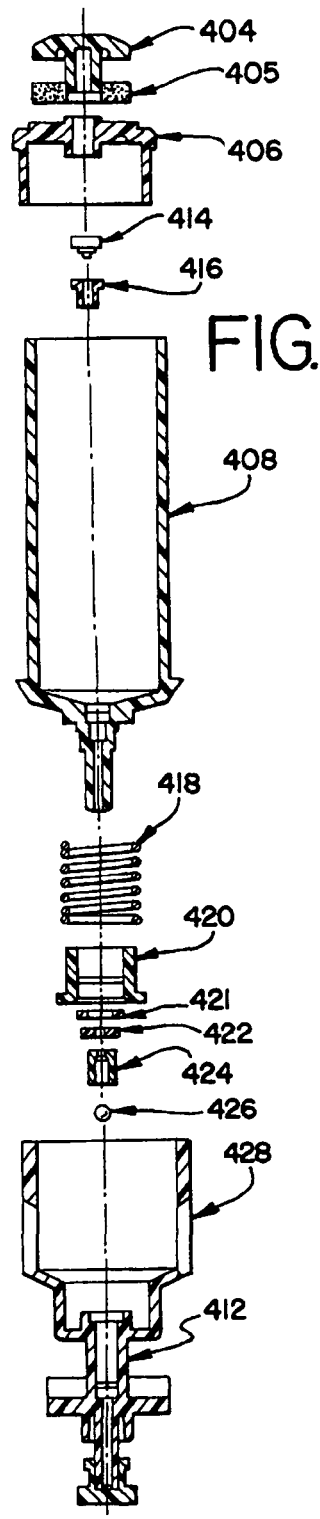
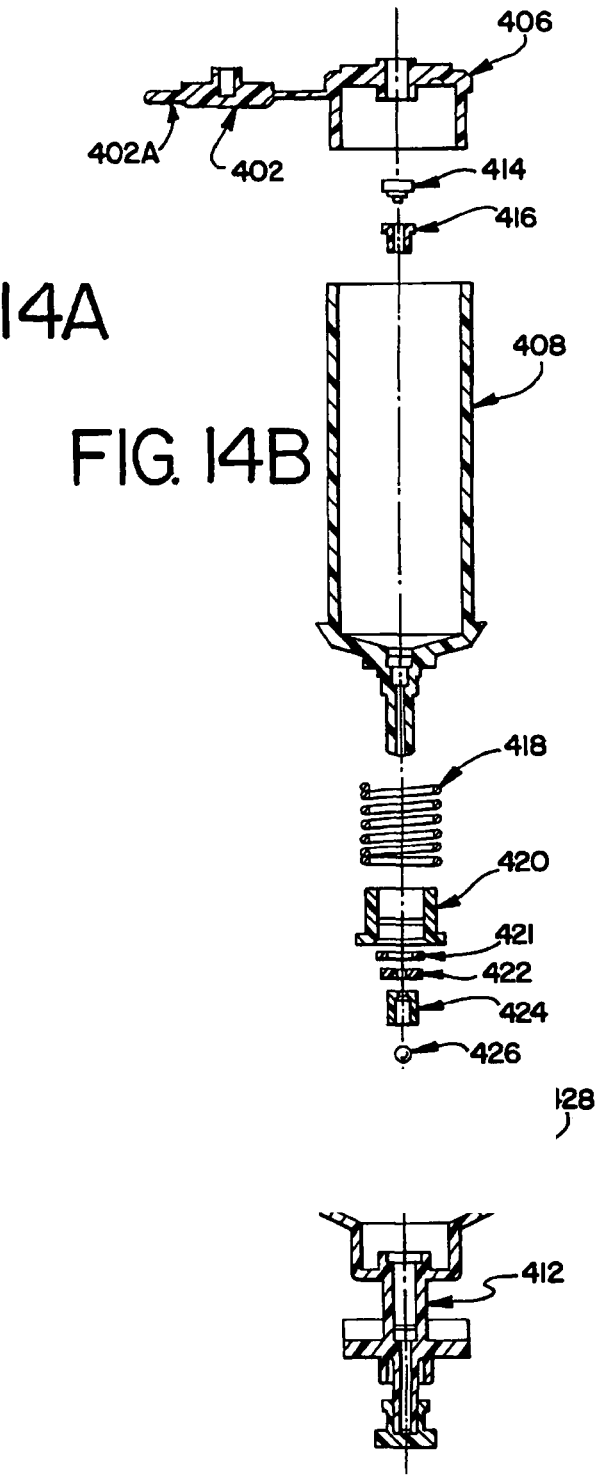
FIG. 14A
FIG. 14B

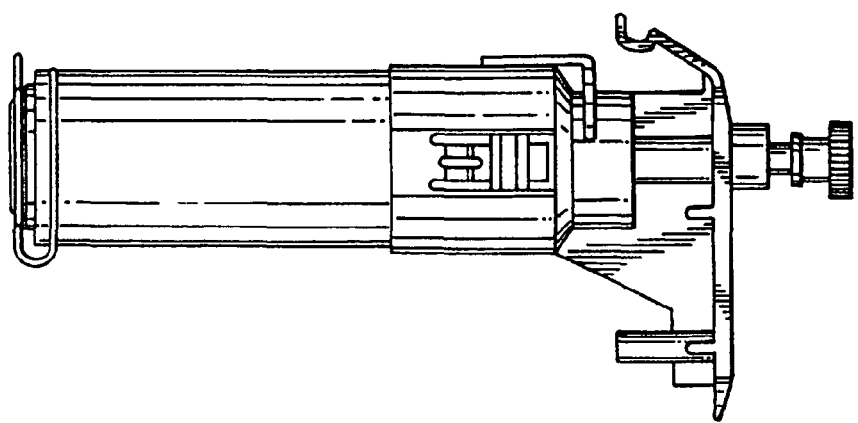
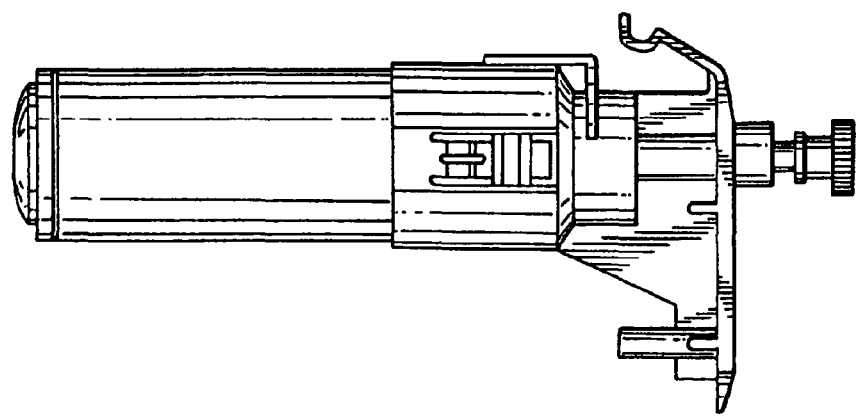

MEMORY MANAGEMENT METHOD AND APPARATUS FOR AUTOMATED BIOLOGICAL REACTION SYSTEM

REFERENCE TO RELATED APPLICATIONS

This application is a divisional of U.S. patent application Ser. No. 09/469,601, filed Dec. 21, 1999 now abandoned, which is a continuation of U.S. patent application Ser. No. 08/909,335, filed on Aug. 11, 1997, now U.S. Pat. No. 6,093,574, issued Jul. 25, 2000.

NOTICE REGARDING COPYRIGHT

A portion of the disclosure of this patent document contains matter subject to copyright protection. The copyright owner has no objection to the facsimile reproduction by anyone of the patent disclosure document as it appears in the Patent and Trademark Office files and records but otherwise retains all copyrights whatsoever.

BACKGROUND OF THE INVENTION

A. Field of the Invention

This invention relates to biological reaction systems, and more particularly relates to a method and apparatus for an automated biological reaction system.

B. Description of Related Art

Immunostaining and in situ DNA analysis are useful tools in histological diagnosis and the study of tissue morphology. Immunostaining relies on the specific binding affinity of antibodies with epitopes in tissue samples, and the increasing availability of antibodies which bind specifically with unique epitopes present only in certain types of diseased cellular tissue. Immunostaining requires a series of treatment steps conducted on a tissue section mounted on a glass slide to highlight by selective staining certain morphological indicators of disease states. Typical steps include pretreatment of the tissue section to reduce non-specific binding, antibody treatment and incubation, enzyme labeled secondary antibody treatment and incubation, substrate reaction with the enzyme to produce a fluorophore or chromophore highlighting areas of the tissue section having epitopes binding with the antibody, counterstaining, and the like. Each of these steps is separated by multiple rinse steps to remove unreacted residual reagent from the prior step. Incubations are conducted at elevated temperatures, usually around 40° C., and the tissue must be continuously protected from dehydration. In situ DNA analysis relies upon the specific binding affinity of probes with unique nucleotide sequences in cell or tissue samples and similarly involves a series of process steps, with a variety of reagents and process temperature requirements.

Automated biological reaction systems include the biological reaction apparatus and the dispensers for the reagents and other liquids used in the biological reaction apparatus. As disclosed in U.S. Pat. No. 5,595,707, inventors Copeland et al., entitled Automated Biological Reaction Apparatus, assigned to Ventana Medical Systems, Inc. which is incorporated herein by reference, the biological reaction apparatus may be computer controlled. However, the computer control is limited in that it is dedicated to and resident on the biological reaction apparatus. Moreover, the memory, which is used in conjunction with the computer control, contains data relating to the reagents including serial number, product code (reagent type), package size (250 test), and the like.

One of the requirements in a biological reaction system is consistency in testing. In particular, the biological reaction system should apply a predetermined amount of liquid upon the slide in order to consistently test each slide in the automated biological reaction apparatus. Therefore, an important focus of a biological reaction system is to consistently and efficiently apply a predetermined amount of liquid on the slide.

Further, as disclosed in U.S. Pat. No. 5,232,664 entitled Liquid Dispenser by inventors Krawzak et al. and assigned to Ventana Medical Systems, Inc., which is incorporated herein by reference, reagents must be dispensed on the slide in precise amounts using a liquid dispenser. The liquid dispenser, which is used in conjunction with the biological reaction apparatus, should be easy to manufacture, reliable and compact in size.

SUMMARY OF THE-INVENTION

In accordance with a first aspect of the invention, a method and apparatus for consistently placing an amount of liquid on a slide is provided. In accordance with a second aspect of the invention, a new dispenser for the automated biological reaction system is provided. In accordance with a third aspect of the invention, the automated biological reaction system which is modular in design is provided. The system is composed of a host device and at least one remote device. In accordance with a fourth aspect of the invention, a method and apparatus for transferring data relating to dispensers used in the automated biological reaction system is provided. Data is loaded to a memory device, which in turn is used by the operator to update the operator's databases. In accordance with a fifth aspect of the invention, the generation of the sequence of steps for the automated biological reaction device is provided. The sequence of steps is based on data loaded by the operator.

Accordingly, a primary object of the invention is to provide an automated biological reaction system which is modular in design.

Another object of the invention is to provide an automated biological reaction system which provides for a means of automatically downloading data relating to the reagents including serial numbers, reagent types, lot numbers, expiration dates, dispenser type, and the like in an efficient and reliable manner.

Another object of the invention is to provide an automated biological reaction system which consistently and efficiently applies a predetermined amount of buffer upon the slide to which a precise volume of reagent can be added upon the slide.

A further object of the invention is to provide a liquid dispenser, which is used in conjunction with the biological reaction apparatus, which is reliable.

Yet a further object of the invention is to provide a liquid dispenser, which is used with a wider array of chemistries in conjunction with the biological reaction apparatus, which is easy to manufacture.

Still another object of the invention is to provide a liquid dispenser, which is used in conjunction with the biological reaction apparatus, which is compact in size.

These and other objects, features, and advantages of the present invention are discussed or apparent in the following detailed description.

BRIEF DESCRIPTION OF-THE DRAWINGS

A presently preferred embodiment of the present invention is described herein with reference to the drawings wherein:

FIG. 5A is a block diagram of the modularity of the host and remote devices of the automated biological reaction system;

FIG. 5B is a format of the addressing for the host devices and remote devices described in FIG. 5A;

FIG. 7A is a block diagram of the dual rinse and volume adjust components of the remote device in FIG. 6A;

FIG. 8B is a side view of the angle of the dual-rinse top nozzle as shown in FIG. 8A;

FIG. 8C is a side view of the angle of the dual rinse bottom nozzle as shown in FIG. 8A;

FIG. 8D is a side view of one embodiment of the volume adjust as shown in FIG. 7A;

FIG. 12A is an elevational cutaway view of a prefilled liquid dispenser in the extended position;

FIG. 12B is an elevational cutaway view of a user fillable liquid dispenser in the extended position;

FIG. 12C is an elevational cutaway view of a prefilled liquid dispenser in the compressed position;

FIG. 14A is an exploded view of an elevational cutaway of a prefilled liquid dispenser;

FIG. 14B is an exploded view of an elevational cutaway of a user fillable liquid dispenser;

FIG. 15A is a side view of a prefilled liquid dispenser;

FIG. 15B is a side view of a customer fillable liquid dispenser with flip top;

DETAILED DESCRIPTION OF THE PREFERRED AND ALTERNATIVE EMBODIMENTS OF THE INVENTION

The automated immunostaining system of this invention performs all steps of immunohistochemical irrespective of complexity or their order, at the time and temperature, and in the environment needed. Specially prepared slides containing a bar code identifier and a mounted tissue section are placed in special supports on a carousel, subjected to a preprogrammed sequence of reactions, and are removed from the carousel, ready for examination. For purposes of clarity of the following description of the apparatus of this invention and not by way of limitation, the apparatus will be described in terms of immunohistochemical processes.

Figure 1:
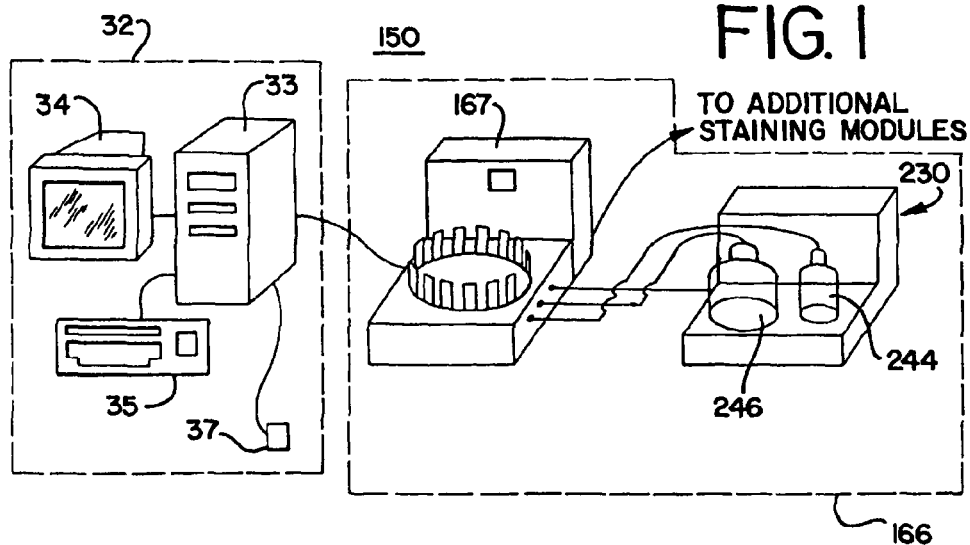
FIG. 1 is a left front, isometric view of the automated biological reaction system according to a first embodiment of this invention.
Figure 2:
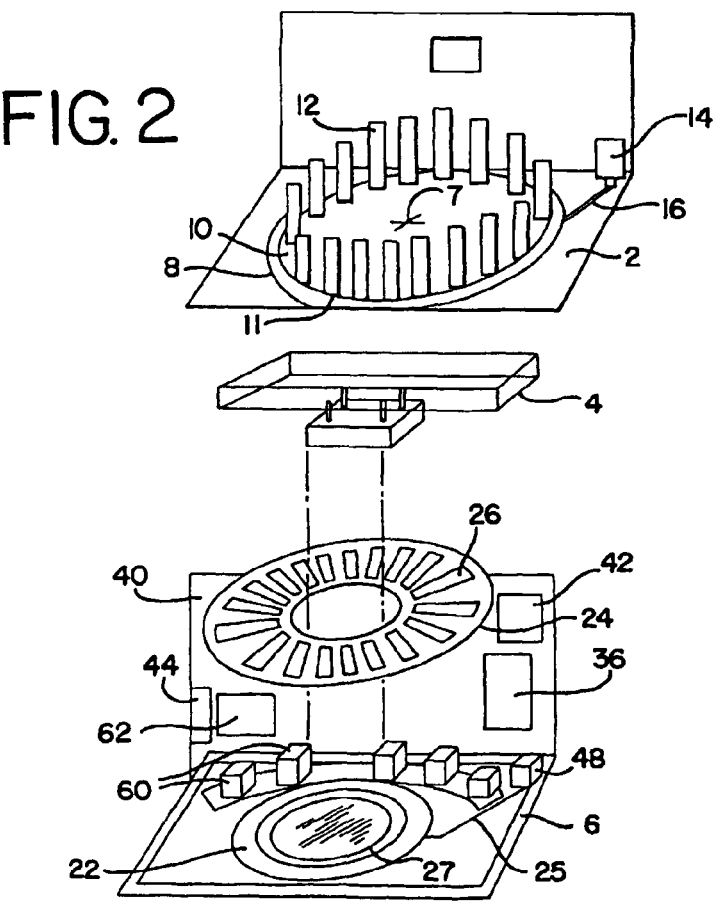
FIG. 2 is an exploded right front isometric view of the system shown in FIG. 1.

FIG. 1 is front right isometric view of the automated biological reaction system with a host device 32 and one remote device 166. The remote device 166 includes a staining module 167, bulk fluid module 230 and the host device 32 includes a host computer 33, a monitor 34, a keyboard 35 and a mouse 37. FIG. 2 is a front right isometric view of the staining module which is part of the automated biological reaction system. Liquid and air supply tubing and electrical wiring connecting the respective components are conventional, well known in the art, and are omitted from the drawings for purposes of clarity.

The apparatus has an upper section 2, intermediate section 4 and lower section 6. In the upper section 2, reagent tray 10 which supports the reagent liquid dispensers 12 is mounted for rotation about its central axis 7 on reagent carousel 8. The reagent carousel 8 and slide carousel 24 are circular in the preferred embodiment, but can be any shape which allows integration with other components in the system. Reagent liquid dispensers 12, described herein with respect to FIGS.

10-18, required for the immunohistochemical reactions to be conducted during slide treatment cycle are supported by the reagent tray 10, mounted in reagent liquid dispenser receptors 11. These receptors 11 are configured to receive reagent liquid dispenser. The receptors 11 are preferably equally spaced in a circular pattern axially concentric with the carousel axis 7. The number of receptors 11 provided should be sufficient to accommodate the number of different reagent liquid dispensers 12 required for a cycle or series of cycles. Twenty-five liquid dispenser receptors 11 are shown, but the number can be smaller or greater, and the diameter of the reagent tray 10 can be increased to accept a larger number of reagent liquid dispensers 12. The reagent carousel 8 is rotated by the stepper motor 14 drive belt 16 to a position placing a selected reagent liquid dispenser 12 in the reagent deliver position under the air cylinder reagent delivery actuator 18 over a slide to be treated with reagent.

Figure 3:
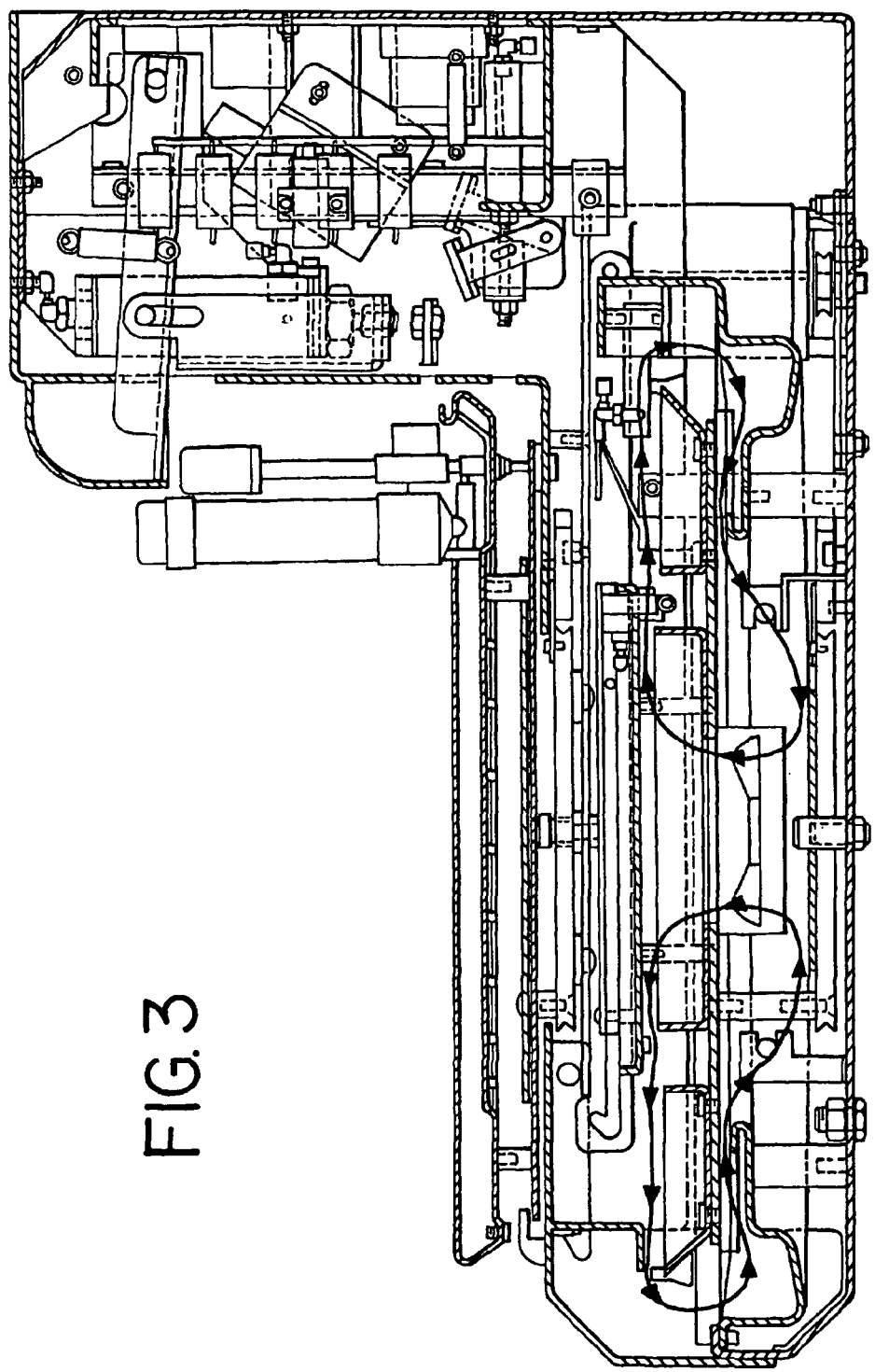
FIG. 3 is a partial exploded left front isometric view of the system shown in FIG. 1.

The intermediate section 4 comprises a vortex mixing plate to which the 4 of the 6 mix blocks are attached, the remaining two mix blocks being mounted on the lower section. The lower section 6 comprises support plate 22 upon which the slide carousel 24 is rotably mounted. The slide carousel 24 supports slide supports 26. Heated air is supplied to the apparatus via a resistive heating element and a blower. The heated air recirculates within the apparatus as shown in FIG. 3. The support plate 22 also supports a remote device microcontroller 36 on the automated biological reaction apparatus, power supply 24 and liquid and pneumatic values. The remote device microcontroller printed circuit board 36, as described subsequently, is generally a processor and can be replaced by a standard computer. The remote device microcontroller printed circuit board 36 interfaces, via an RS-485 line, with a host device 32, as described subsequently in FIGS. 5A-5C. The lower section 6 includes support plate 40 upon which are supported accessories such as power supply 42 and buffer heater 44.

In the lower section 6, the stepper motor 48 rotates the slide carousel 24, engaging drive belt 25 engaging the drive sprocket of the slide carousel 24. The annular waste liquid sump 58 surrounds the shroud 54 and is supported on the bottom of plate 22. The waste reagent and rinse liquids are collected in the sump and passed to a drain through an outlet tube in the sump bottom (not shown).

Figure 4:
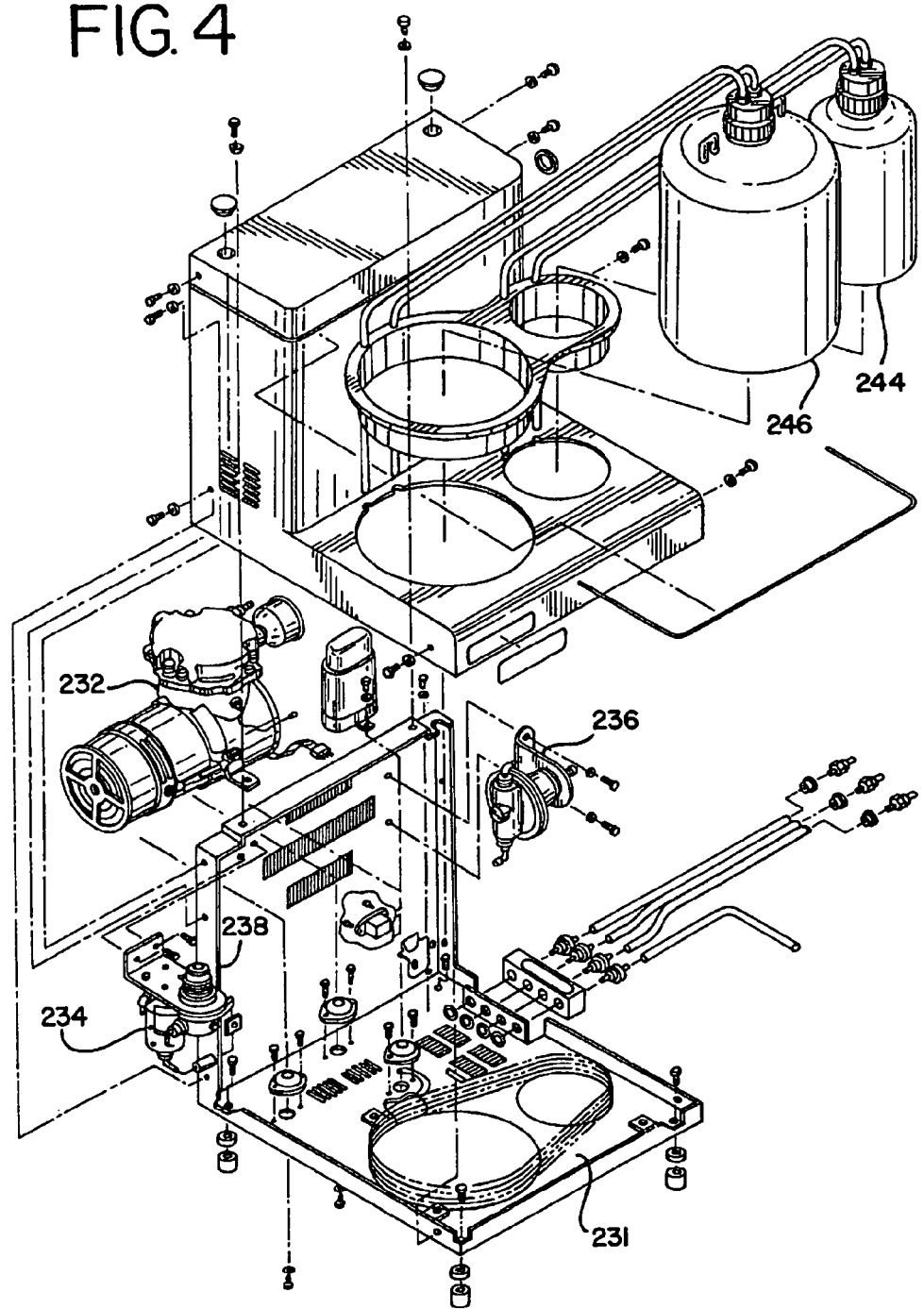
FIG. 4 is a partial exploded right rear isometric view of the apparatus shown in FIG. 1.

Rinse and Liquid Coverslip™ (which is light oil substance used to prevent evaporation of the aqueous solutions on the slide) spray blocks 60 are supplied with liquid through conventional solenoid valves 62 (see also FIG. 6A, 248F-J). Buffer heater temperature sensor 66, mounted on buffer heater 44, controls the heat energy supplied to the buffer heater 44. Slide temperature monitoring sensor 68, mounted on support plate 22, control the temperature of the air in the apparatus by controlling energy supplied to annular heater elements 27. Power supply 42 provides power to the stepper motors 14, 48 and control systems. FIG. 4 is a left front isometric view of the bulk fluid module system 230 which is included in the automated biological reaction system 150. The bulk fluid module 230 includes an air compressor 232, a pressure relief valve 238, cooling tubing 231, a water condenser and filter 234, an air pressure regulator 236, a bottle containing wash buffer 246, and a bottle containing Liquid Coverslip™ 244. The air compressor 232 provides compressed air which is regulated by the pressure relief valve (prv) 238 to 25 psi. The air passes from the compressor 232 through the cooling tubing and enters the condenser and filter 234. From the condenser and filter 234, the air passes to the pressure regulator 236. The pressure regulator 236 regulates the pressure to 13 psi. The air, maintained at 13 psi, is supplied to the wash buffer bottle 246 and the Liquid Coverslip™ bottle 244 and the staining module 167 (see FIG. 2). Water condensing out of the compressed air passes out of the condenser and filter through the pressure relief valve and exits the bulk module. Wash buffer and Liquid Coverslip™ are supplied to the staining module.

Referring to FIG. 5A, there is shown a block diagram of the automated biological reaction system 150. The automated biological reaction system 150 is segmented into a host device 32, which includes a typical personal computer, and at least one remote device 166, which includes the automated biological reaction device in FIGS. 1-4. In the preferred embodiment, there are up to eight remote devices 166 which communicate with the host device 32. Each remote device 166 on the network has a unique address so that each remote device 166 may identified and individually controlled by the host device 32. As described subsequently in FIG. 5B, the automated biological reaction system 150 can support up to eight remote devices 166 due to the 3 bits (values 0-7) dedicated to the addressing of the remote devices 166. A rotary switch is provided on the remote device 166 to allow for the identification and the changing of the 3 bit address for each remote device 166. All host messages includes this address in them, as described subsequently in FIG. 5B. However, the number of remote devices 166 can be smaller than eight, depending on the capacity requirements or practical limitations of the laboratory in terms of space. Moreover, the remote devices 166 may be immunohistochemistry staining modules or another type of instrument that performs a different type of staining.

Communication between the host device 32 and the remote devices 166 is accomplished using a serial RS-485 link, which serves as a network, that supports one host and up to 32 remotes at one time. In the preferred embodiment, addressing of the remote devices 166 allows up to 8 remotes devices to communicate with the host at one time. The RS-485 link has at least two pairs of lines for communication, one pair for transmitting and one pair for receiving. The remote devices 166 which are connected to the network "hear" the host messages but do not "hear" other remote messages. In the preferred embodiment, all communications begin with a host message, followed a short time later by a response by a remote device 166 if present. If the host device 32 sends a message and there is no remote device 166 to respond to it, the host device 32 times out. In this manner, the communication provides a simple, collision-free link between the host device 32 and the remote devices 166. In an alternative embodiment, the remote devices 166, in addition to communicating with the host device 32, address each other. For example, the remote devices 166 address each other using the unique 3 bit address, sending information about staining runs, which are described subsequently.

As shown in FIG. 5A, the host device 32 is a typical personal computer with a processor 152 which includes a comparator 154 for comparing values in the processor. The processor 152 is also in communication with memory devices 156, including non-volatile memory devices such as a ROM 158, volatile memory devices such as a RAM 160, and a hard disk 164 which contains databases or look-up tables 164. The remote device 166 includes a processor, such as a microcontroller 36 wherein the microcontroller 36 has a comparator 170 for comparing values in the microcontroller 36. In an alternative embodiment, the microcontroller 36 in the remote device 166 is replaced by a personal computer. The microcontroller 36 is manufactured by Dallas Semiconductor, model number DS2251T 128K Soft microcontroller module. The microcontroller 36 has two lines (serial to PC, serial to next inst) to facilitate communication between the host and the remote devices. As shown in FIG. 5A, the host device 32, through the processor, is connected to the serial to PC pin of the microcontroller 36 of remote device 1 (166). The serial to next Inst line of the microcontroller 36 of remote device 1 (166) is connected to the serial to PC pin of remote device 2 (166). The connections follow similarly through remote device N (166). In the preferred embodiment, there are up to 8 remote devices on the network. In order to terminate the network with the correct impedance in order to avoid any pulse reflections on the network, the serial to next instrument line is connected to a terminator 171. The terminator 171 can thereby match the impedance of the network. In the event that one of the remote devices on the network must be removed from the network, the serial to PC line and the serial to next remote device line need only be connected to each other for the remote device 166 to be removed from the network. Thereby, the network does not "see" that remote device 166 and is effectively removed from the network.

Referring to FIG. 5B, there is shown a format of the addressing for the host and remote devices 166 described in FIG. 5A. Both the host device 32 and the remote devices 166 have the same format and are distinguishable from one another only by the messages in their fields. Both the host device command and the remote device response for a given message transaction contains the same message. The first character is the start of message character. The $8^{th}$ bit is always set to 1, the lower 3 bits contain the address of the remote and bits 3-6 are unused. The host device 32 addresses the remote device 166 in this manner. The addressed remote responds in kind with its own address here.

The message length is 2 characters in length. This number indicates the number of characters in the entire message. This includes the start of message character and the message checksum character. This is the actual number of characters transmitted as seen through the host/remote serial ports. The message ID is one character in length. It tags a message with a number (1-255) that identifies it from other messages. The message ID provides identification for message acknowledges from the remote and provides safe message retry processing in the remote. The message ID is implemented by incrementing a number until it reaches 255, and thereafter returning to 0. Each successful message transmission causes the message ID to increment by 1. Retransmitted messages from the host, due to unsuccessful acknowledgments from the remote, are repeated with the same message ID as the original message. The message command is 1 character in length. For host messages, the message command indicates to the remote the type of command the message command data pertains to. For remote messages, this field is used to tell the host device 32 how the request was received. The message command data is of variable length. It contains additional message data, depending on the particular host command. The size of the message command data is dictated by the message length, described previously. After removing the other fields from around this field, the remainder is the message information. Since message commands may not require message command data, this field may not always be used. The message checksum is 1 character in length. It contains the computed checksum of all characters in the message, starting with the start of message character and including all message characters up to, but not including, this checksum field. No message is processed if the message checksum does not match the actual computed checksum of the received message.

Figure 5C:
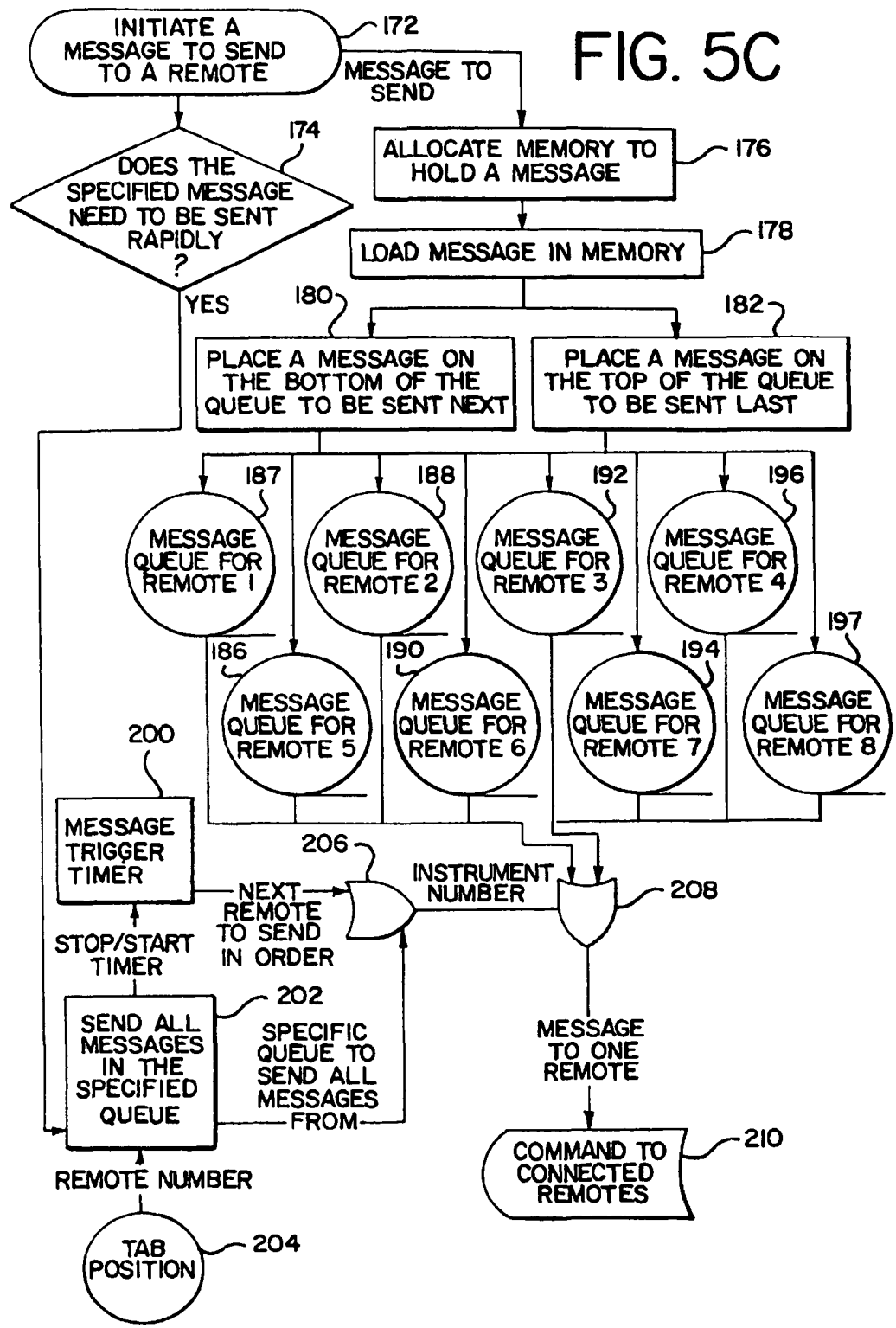
FIG. 5C is a communication transmission protocol between the host device and remote devices described in FIG. 5A.

Referring to FIG. 5C, there is shown a communication transmission protocol between the host device 32 and remote devices 166 described in FIG. 5A. Messages are downloaded from the host device 32 to the remote devices 166. The host device initiates a message to send to a remote device (172). The host device allocates memory to hold a message 176 and loads the message into memory 178. The host device 32 then places the message at the top or at the bottom of the queue 180, 182, depending on the priority of the message. Since the queue is first-in-first-out, the messages at the bottom of the queue go out first. Therefore, if a message must be sent out immediately, it is placed at the bottom of the queue 180. Otherwise, if it is an routine status message, the message is placed at the top of the queue 182. Thereafter, the messages are sent to the message queues for each of the up to eight remote devices 184, 186, 188, 190, 192, 194, 196, 198.

Ordinarily, when a message is sent from the host device 32 to a remote device 166, messages are sent periodically through use of a timer. When the host device 32 determines that a message needs to be sent rapidly 174, the timer is turned off 200 and all of the messages from the specific queue as indicated by the host are sent 202. If the host device 32 determines that the message does not need to be rapidly sent, the message is sent in the predetermined sequence based on the timer by sending the next remote in order 206. The host uses the tab position 204 which indicates which remote to send the message to.

Figure 6A:
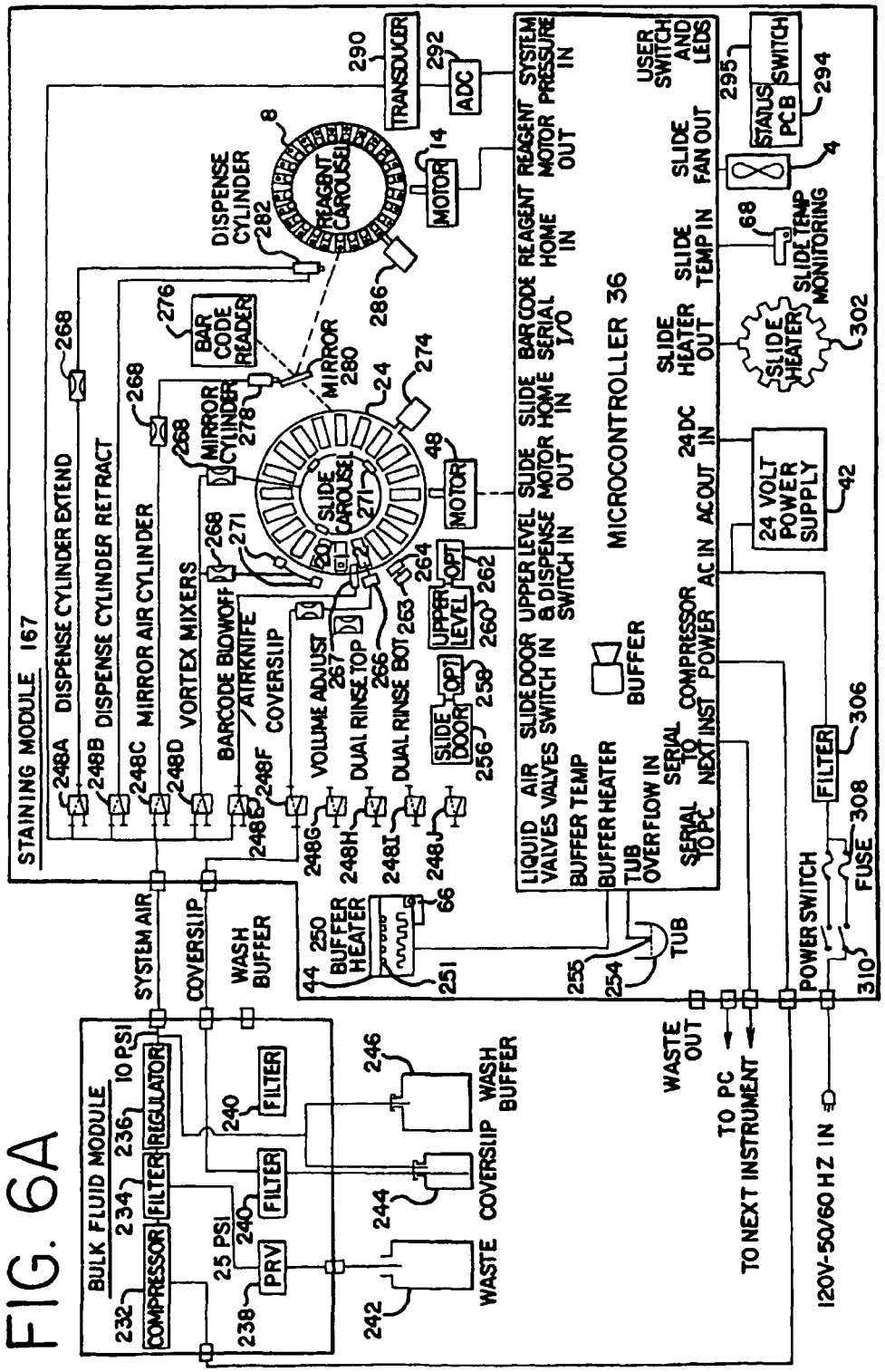
FIG. 6A is an expanded block diagram of the remote device in FIG. 5A.

Referring to FIG. 6A, there is shown an expanded block diagram of the remote device 166. As discussed previously, the remote device 166 includes a microcontroller 36. The microcontroller 36 has a user switch and LEDs line which connects to the status PCB (printed circuit board) 294. The status PCB 294 is the interface to the user for the remote device 166 and includes three LEDs (light emitting diodes) for power determination, error notification and notification of a run in progress. The status PCB 294 also includes a switch, such as a push-button switch, which is used for testing of various functions. When the push-button switch 295 is depressed, the microcontroller 36 executes the last instruction that was entered in the microcontroller 36. In this manner, the operator may test the last instruction by simply depressing the button 295 rather than going to the host device 32 (which may be in a different location) and resending the last command.

The microcontroller 36 also has a slide fan out connection which is used to control the blower fan 4. The blower fan 4 recirculates air to heat the slides on the slide carousel 24 of the remote device 166 by forcing air over the heater 302 and then over the slides. The slide temp in connection is connected to the slide temperature monitoring sensor 68 which senses the temperature of the air. The slide temperature monitoring sensor 68 is positioned in the path of the heated air and thereby sends information to the microcontroller 36 when to turn the slide heater 302 on and off. The slide heater out connection is connected to the slide heater 302 which, as discussed previously, heats the air in order to elevate the temperature of the slides. As discussed subsequently, the host device 32 downloads to the remote device 166 both the sequence of steps in a run program, and the sensor monitoring and control logic called the run rules. One of the environmental parameters is the upper and lower limit of the air temperature of the slides (used for heating the slides). If, during a run, the environmental temperature is below the lower limit, as indicated by slide temperature monitoring sensor 68, the slide heater 302 is turned on. Likewise, if the environmental temperature is above the upper limit, as indicated by slide temperature monitoring sensor 68, the slide heater 302 is turned off. The power supply 24 supplies both 24 VDC and 5 VDC to the applicable 24 VDC and 5 VDC connections. The 24 Volt power supply 24 is used to power the motors 14, 48 which move the slide carousel 24 and the reagent carousel 8 and the valves 248A-J, which are described subsequently. The 120 VAC input is sent through a power switch 310, a fuse 308 and a filter 306 to the AC In connection of the power supply 24. The 120 VAC input is also used to power the slide heater 302, buffer heater 44 and compressor 232 of the bulk fluid module, which are described subsequently. The serial to PC line and the serial to next remote device line are described with reference to FIG. 5A. The tub overflow in line receives input from a conductivity sensor 255 which senses the level of the waste in the tub 254. When the conductivity sensor 255 senses that the waste line is above a predetermined level, the conductivity sensor 255 notifies the microcontroller 36, which in turn sends a status message to the host device 32. The operator is first given an opportunity to clear the waste from the tub 254. If the tub 254 is still above the predetermined level, the run is stopped.

The buffer heater 44 is used to heat the wash buffer before it is placed on the slides since it has been determined that better results are achieved by heating the wash buffer to the temperature of the tissue on the slide. The buffer heater 44 consists of a cast aluminum block 249 with a spiral tubing 251 inside the block. When the wash buffer flows through the tubing 251 through the block 249, the temperature of the wash buffer will be the temperature of the aluminum block 249 upon exit from the tubing 251. In order to control the temperature of the block, a buffer heater temperature sensor 66 is used which is physically placed on the aluminum block 249. The microcontroller 36 receives the buffer temperature sensor input via the buffer temp line and can thereby control the temperature of the buffer heater 44 by turning on and off the buffer heater 44 via the buffer heater line on the PCB microcontroller 36.

The liquid valves 248A-J for the Liquid Coverslip™ and the wash buffer are controlled by the liquid valve connections. There is a separate pair of wires (power and ground) for each valve 248A-J shown in FIG. 6A which are omitted for ease of display. Each valve 248A-J is a relay which is activated by the microcontroller 36 by energizing the relay. The volume adjust 266, dual rinse top 263, and two dual rinse bottom 264 devices will be described subsequently in FIGS. 7-9. Further, there is a slide door optical sensor 258 which is input to the slide door switch in line connection and which is used to determine if the front door of the remote device 166 is open. This sensor 258 is used for safety reasons so that, if the front door is open and remains open for five minutes, the slide carousel 24 does not move. Moreover, there is a second optical sensor, the upper level optical sensor 262, which is used to determine if the upper chassis on the remote device 166 has been opened.

Further, as shown in FIG. 6A, the dispense cylinder 282 uses the dispense cylinder extend and the dispense cylinder retract so that the dispense plunger extends and retracts the liquid dispensers. Using air via the system air line, the dispense cylinder 282 is pushed out by using the dispense cylinder extend line. The microcontroller 36 controls the air valves 248A, 248B so that the relay corresponding to the dispense cylinder extend line is activated. In this manner, the dispense cylinder 282 pushes the liquid dispenser down, as described subsequently in FIGS. 12A-12C, thereby dispensing reagent. In order to retract the dispense cylinder 282, the dispense cylinder retract valve 248B is activated using the system air line so that the liquid dispenser is pushed to retraction. Additionally, an extension spring is used to help speed the retraction process, as described subsequently. An optical sensor is used to determine if the dispense is extended, and thereby activated. When the dispense cylinder 282 is extended, the optical sensor is tripped validating that the dispense operation has occurred. Motors 14, 48 move the slide carousel 24 and the reagent carousel 8 and are connected to the slide motor out connection and the reagent motor out connection, respectively. The motors 14, 48 are typically stepper motors.

Sensors 274, 286 are placed in proximity to the slide carousel 24 and the reagent tray in order to determine the "home" position of each. In the case of the slide carousel 24, the slide carousel home sensor 274 is inductive-type and senses a piece of metal placed underneath the slide designated as the "home" position. When the "home" position is found, the sensor 274 sends a signal to the slide home in line of the microcontroller 36. In the case of the reagent tray 10, the sensor 286 also is an inductive-type of sensor. The reagent tray 10 has a large flat metal ring around the entire tray except for the home position. In this manner, when the sensor 286 senses an absence of metal, this is determined to be the home position thereby indicating to the microcontroller 36, via the reagent home in connection, that the home position is found. The sensor 286 senses the reagent tray 10, rather than the reagent carousel 8, since the user may remove the reagent tray 10. Additionally, since the sensor 286 looks for the absence of metal for the home position, the absence of the reagent tray 10 may be tested by looking for the absence of metal in two consecutive positions.

System pressure is determined via the system air line which directly feeds into a transducer 290. The transducer 290 generates an analog voltage which is proportional to the pressure. The output of the transducer 290 is then sent to an analog to digital converter (ADC) 292 whose output is sent to the microcontroller 36 via the system pressure in connection. Contrary to previous pressure switches which only indicated whether the pressure was below a minimum value, the transducer 290 and ADC 292 combination indicates to the microcontroller 36 the exact pressure. Therefore, the microcontroller 36 can determine both whether the pressure is too low and too high. In either instance, the microcontroller 36 sends an error message and shuts down the run.

As shown in FIG. 6A, the bulk fluid module 230 includes the compressor 232 which pressurizes the air to up to 90 psi. The compressed air is sent to a filter 234 in order to filter out the water and other contaminants. Pressure is regulated in a two-step fashion. First, the pressure is regulated at the compressor to approximately 25 psi (±1 psi) via a spring diaphragm (prv) 238. The pry 238 is manufactured by Norgren in Littleton, Colo., part number NIP-702 with a plastic bonnet. Second, the pressure is fine-tuned to 13 psi using an air pressure regulator 236. The pressure regulator 236 is very accurate in terms of precise pressure regulation over long periods of time. In this manner, the compressor 232 need not overwork itself since the pry 238 maintains the pressure at the output of the compressor to 25 psi by opening and letting out excess pressure when the pressure exceeds 25 psi. Water and particulates, which are filtered out of the air via the filter 234, are sent to a waste receptacle. The compressed air pressurizes the Liquid Coverslip™ and wash buffer bottles 244, 246 so that when the valves 248F-J are opened corresponding to the Liquid Coverslip™, volume adjust, dual rinse top, dual rinse bottom lines, the pressure is already on the line and the liquid may flow. In addition, the compressed air is used for the dispense cylinder extend line, the dispense cylinder retract line, the mirror air cylinder line, the vortex mixers line, and the bar code blowoff/airknife line. Filters 240 are used at the outputs of the Liquid Coverslip™ and wash buffer bottles 244, 246 in order to remove particulates which may get caught in the valves 248.

The mirror air cylinder line is used to turn the mirror cylinder 278 so that the bar code reader 276 either reads bar codes on the slides of the slide carousel 24 or bar codes on the liquid dispensers on the reagent carousel 8. The output from the bar code reader 276 is input to the microcontroller 36 via the bar code serial I/O connection. In between the valve 248C for the mirror air cylinder line and the mirror cylinder is a flow restrictor 268. The flow restrictor 268 slows the flow of air in the line while still maintaining the 13 psi pressure on the line. In this manner, this moves the mirror slower than would otherwise be done without the restrictor 268.

The vortex mixers 271 likewise operate off of the 13 psi system air line to mix the contents on the slide. The vortex mixers 271 may be used in a single stream or in a dual stream mode. In particular, a single stream of air or a dual stream of air may be used to mix the contents on the slide. Further, restrictors 268 are used in the vortex mixers lines in order to reduce the flow of air. In this manner, when the vortex mixers 271 are used to mix the contents on the slide, the liquid does not blow off the slide and the mixers do not dry any particular spot on the slide.

The bar code blowoff/airknife 267 is used to blow air on the portion of the slide which contains the bar code. In this manner, the bar code is easier to read. Further, liquid can be kept on the slide better due to surface tension if liquid near the edge of the slide is removed.

Figure 6B:
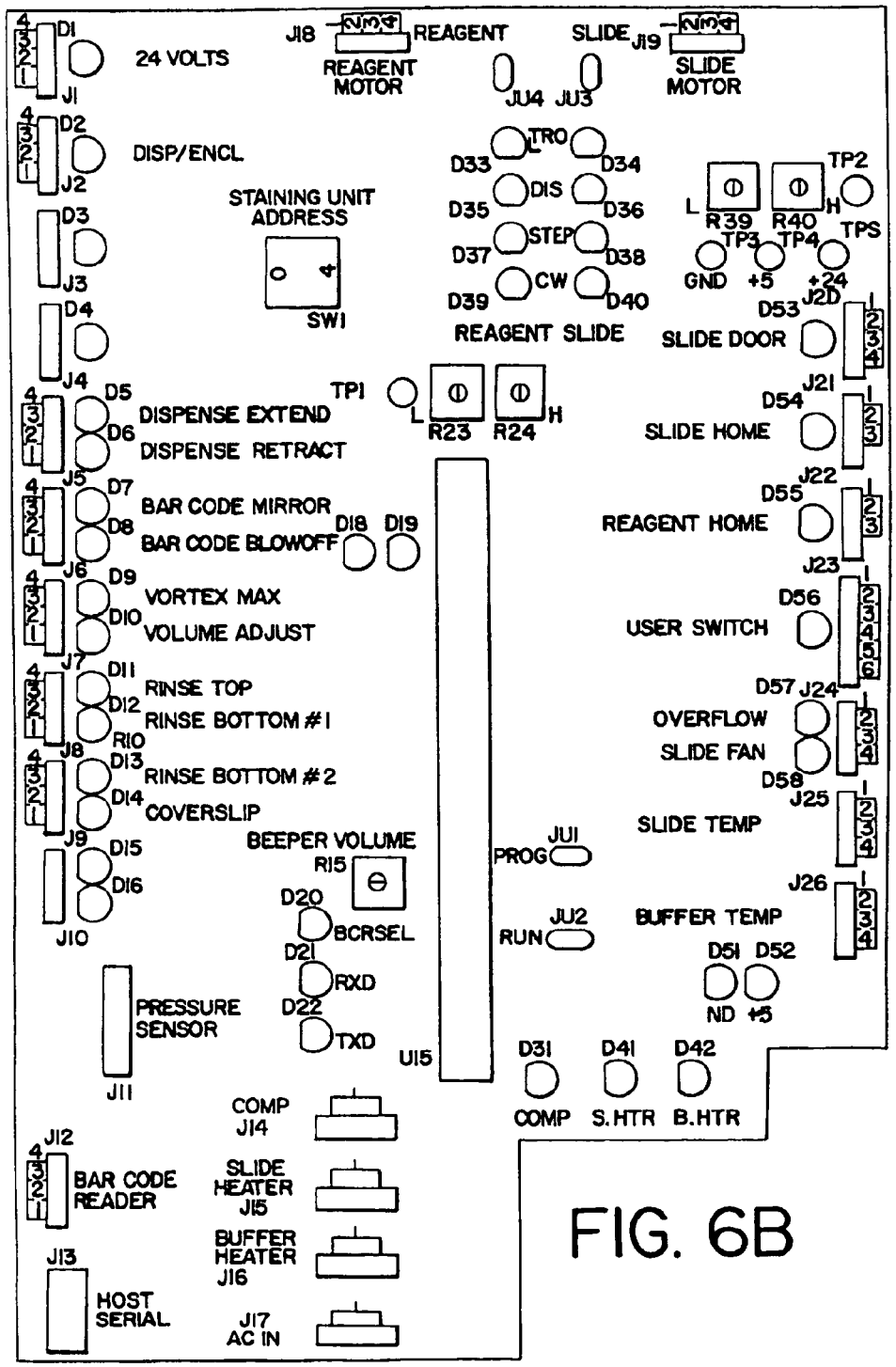
FIG. 6B is a circuit board connection diagram for the microcontroller.

Referring to FIG. 6B, there is shown a circuit board connection diagram for the microcontroller. The sensors and motors for the remote device 166 plug into this board which in turn is in communication with the microcontroller.

Referring to FIG. 7A, there is shown a block diagram of the dual rinse and volume adjust components 263, 264, 266 of the remote device 166 in FIG. 6A. A run is generally executed in a series of steps including the following: reagent is applied to the slide, Liquid Coverslip™ is applied to the slide, the reagent reacts with the tissue on the slide, a different reagent is applied to the slide, Liquid Coverslip™ is applied to the slide, the different reagent reacts with the slide, etc. After the reagent reacts with the slide, but before the next reagent is applied to the slide, the excess reagent which did not react with the sample should be removed from the slide. Otherwise, there is the possibility of having non-specific staining, or background staining, on the slide. This non-specific staining may interfere with the visual analysis of the slide at the end of the run. In order to minimize the non-specific staining, the residual reagent from the previous step is washed from the sample using a wash buffer. Washing may be achieved using a dual rinse device which executes a dual rinse step using a dual rinse top valve 248 and a dual rinse bottom valve 248, as shown in FIG. 7. The microcontroller 36 controls the valves so that the wash buffer pulses the slide with the dual rinse top valve 248H and one of the dual rinse bottom valves 248I or 248J consecutively. In particular, during the dual rinse step, the microcontroller 36 turns on the dual rinse top valve 248H, then one of the dual rinse bottom valves 248I or 248J, and so on. As described subsequently, there are two dual rinse bottom valves 248I or 248J in order to achieve the consistency pulse.

Figure 7B:
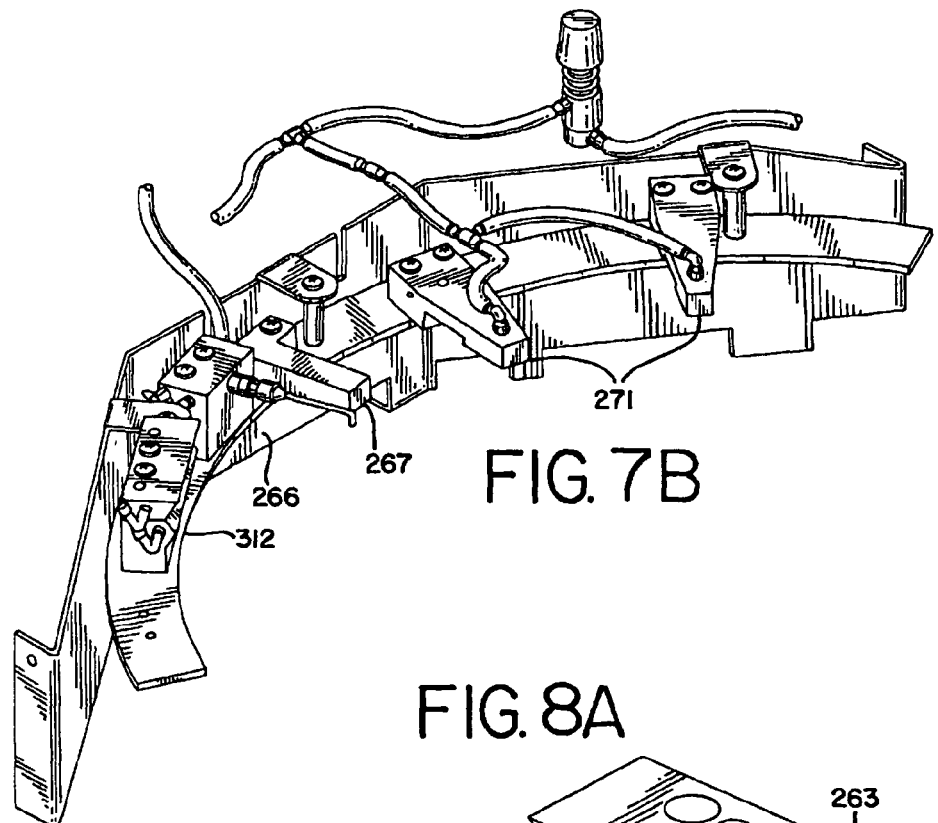
FIG. 7B is a perspective view of the dual rinse top and dual rinse bottom, volume adjust/coverslip, airknife/barcode blowoff and vortex mixers.

Referring to FIG. 7B, there is shown a perspective view of the dual rinse top and dual rinse bottom, volume adjust/coverslip, airknife/barcode blowoff and vortex mixers. The configuration is in the form of a boomerang whereby the boomerang follows the curved portion of the slide carousel 24.

Figure 8A:
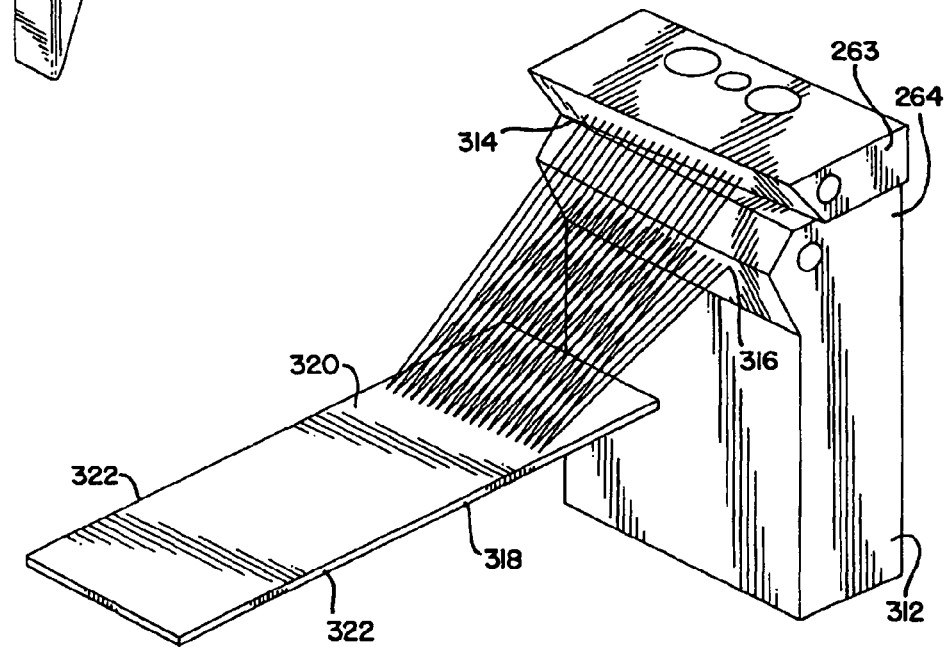
FIG. 8A is a side isometric view of one embodiment of the dual rinse top nozzle and dual rinse bottom nozzle as shown in FIG. 7A.

Referring to FIG. 8A, there is shown a side isometric view of one embodiment of the wash block 312 which employs the dual rinse top nozzle 263 and dual rinse bottom nozzle 264 as shown in FIG. 7. The wash block 312 comprises a lower set of nozzle outlet openings 316 corresponding to the dual rinse bottom nozzle 264 and an upper set of nozzle outlet openings 314 corresponding to the dual rinse top nozzle 263. During the dual rinse step, these openings 314, 316 direct streams of pulsed rinsed liquid towards one or the other of the longitudinal edges 322 of the slide 318. The streams of the pulsed rinsing liquid, from each of the lower and upper sets of nozzle outlet openings 314, 316 preferably impact the slide 318 at the rinse liquid impact zone 320 which is upstream on the slide 318 from the tissue sample (not shown) positioned thereon. Positioning of the wash block 312 is important due to the fragile nature of the tissue sample positioned on the slide. By directing streams of pulsed rinsing liquid at the impact zone 320 of the slide, the rinse liquid is provided with laminar flow by the time the rinse liquid reaches the tissue sample. As a result, undue damage to the fragile tissue sample is prevented.

The upper set of nozzle outlet openings 314 is constructed so that the associated streams of rinse liquid are off-set at an angle from the longitudinal center line of the slide so that the pulsed streams of rinse liquid are directed toward one of the longitudinal edges of the slide 318. The lower set of nozzle openings 316 is constructed so that the associated streams of rinsing liquid are also off-set at an angle from the longitudinal center line of the slide so that the pulsed streams of rinse liquid are directed toward the other one of the longitudinal edges of the slide 318. As a result of this arrangement, pulsed streams of rinse liquid are alternatively and repeatedly directed to one and then the other of the longitudinal edges of the slide.

As shown in FIG. 7, separate plumbing and valving are provided for each of the lower and upper sets of nozzle outlet openings 314, 316 of the dual rinse top nozzle and dual rinse bottom nozzle 263, 264 to permit independent operation thereof. In operation of the dual rinse step, the wash block 312 directs streams of pulsed rinsing liquid, for example from the lower set of nozzle openings 316 toward a single longitudinal edge of the slide and after completion then directs streams of pulsed rinse liquid, for example from the upper set of nozzle openings 314, to the other longitudinal edge of the slide. This procedure is repeated, via control of the valves 248H-J using the microcontroller 36, and has the effect of rinsing the previous layer of rinse liquid and chemicals off of the slide. The wash block nozzle axis of each of the dual rinse top nozzle and dual rinse bottom nozzle 263, 264 forms an angle with the horizontal of between 15 and 35 degrees, preferably substantially 35 degrees for the dual rinse top nozzle 263 and substantially 25 degrees for the dual rinse bottom nozzle 264, as described in FIGS. 8B and 8C. Moreover, the angle of the slide is substantially horizontal (0.5 degrees to 1.25 degrees) so that the wash buffer both washes the excess reagents off of the slide and also flows off of the slide.

After cleaning the excess reagent off of the slide, a precise amount of wash buffer should be applied to the slide. Ordinarily, 270 μL is the optimal amount of buffer which should be placed on the slide for the next step. In executing the dual rinse step, there is residual wash buffer on the slide; however, the amount of wash buffer left on the slide varies considerably. In order to consistently leave a specific amount of liquid on the slide, the microcontroller 36 executes a consistency pulse.

The consistency pulse consistently leaves an amount of liquid on the slide with variation in amount lower than a shorter pulse, and the consistency pulse cleans the slide of excess reagents. The consistency pulse is a pulse of wash buffer which is executed for a longer period of time than the individual pulses of the dual rinse step. To send wash buffer onto the slide, the tubing containing the wash buffer is pressurized. Because of this pressure and because of the turning on and off of the wash buffer valves 248H-J, there is a pressure wave effect generated in the wash buffer tubing. Therefore, one cannot consistently determine where one is on the wave. Because of this wave effect, the amount of pressure that the pulse has varies so that the amount of buffer left on the slide varies as well. In order to minimize the wave effect, the consistency pulse turns the valve on for a period of sufficient time and/or for a sufficient strength in order to let the wave effect minimize within the tubing. The consistency pulse is therefore an extended burst of either the dual rinse top nozzle 263 or the dual rinse bottom nozzle 264 for a period longer than the dual rinse step. For example, as describe in FIG. 9 in more detail below, the period for a pulse during the dual rinse step is 60 mSec whereas the period for the consistency pulse is 300 mSec.

Moreover, in order for the consistency pulse to leave a consistent amount of liquid on the slide, the momentum of the consistency pulse should be greater than that during the dual rinse step. In the preferred embodiment, the increase in momentum of the pulse is achieved by increasing the volume of wash buffer flow using two dual rinse bottom valves 248I and 248J, as shown in FIG. 7, as opposed to using only one dual rinse valve 248I or 248J during the dual rinse step. In this manner, the stream of wash buffer with an increased momentum is sent across the slide with the result that the residual volume of buffer left on the slide after the consistency pulse is lower and also has a lower variation. If a pulse of lower momentum is used, more solution is left on the slide due to interaction with the surface tension of the slide. In an alternative embodiment, the increase in volume and subsequent increase in momentum for the consistency pulse may be achieved using a valve which has an opening which is larger than the opening of the valves 248H-J used during the dual rinse step. The consistency pulse therefore has a strong flow out of the nozzle, generating a laminar, not turbulent, flow on the slide. The laminar flow then washes off the slide, consistently leaving an amount of liquid on the slide. Moreover, the consistency pulse is consistent, not only from run to run on an individual machine, but also from machine to machine as well.

Further, when both a consistent and a minimal amount of buffer is desired to be left on the slide, the dual rinse bottom nozzle 264 should be used rather than the dual rinse top nozzle 263. The angle of the dual rinse bottom nozzle 264 is less than the angle for the dual rinse top nozzle 263; therefore, the less steep the angle, the more likely the buffer will flow off of the slide, not interacting with the surface tension of the slide. For example, using a dual rinse top nozzle 263 with a single valve leaves approximately 275±40 µL on the slide whereas using a dual rinse bottom nozzle 264 with a dual valve leaves approximately 180±20 µL on the slide.

With varying the time of the pulse, the angle of the pulse, and the momentum, the consistency pulse may be used in several ways. The first way is for the consistency pulse to leave a minimal amount of wash buffer on the slide with minimal variation from run to run and machine to machine (180±20 µL) for any given instrument. In particular, this variation of ±20 µL is across all machines so that, in the event that one machine must be replaced by a second machine, the variation is small enough so that the amount of liquid left on the slide is within acceptable parameters. Moreover, the variation from run to run within a single machine is approximately ±10 µL so that, once the machine is calibrated, and the amount of volume dispensed from the volume adjust is determined to achieve a total volume of 270 µL, which is discussed subsequently, the liquid on the slides for a particular machine does not vary significantly run to run.

The modification of the consistency pulse is done by using a time longer than the individual dual step pulse, the dual rinse bottom nozzle 264, and the two valves 248I and 248J; after the consistency pulse step, the required amount of buffer on the slide (as determined by the experiment) may be added using the volume adjust 266, which is described subsequently, with extreme precision.

Apart from using the consistency pulse to leave a minimal amount of buffer on the slide, the consistency pulse may be used to leave an amount greater than a minimal amount while still having a low variation in the amount left on the slide. For example, the operator may adjust the amount of momentum of the pulse, the angle of the outlet nozzle with respect to the slide, and the angle of slide with respect to horizontal. As one example, the outlet of the nozzle may be designed with an angle which is less than the angle of the dual rinse bottom nozzle. In this manner, the operator may tailor the amount left on the slide depending on the amount and variance of the buffer necessary for the experiment.

After the consistency pulse, if additional buffer is necessary to be placed on the slide to run the experiment, the volume adjust is used, as shown in FIG. 7. The microcontroller 36 turns on the valve 248G for the volume adjust line to place buffer on the slide. As described previously, the volume adjust line has a restrictor 268 which reduces the volume flow of the wash buffer through the line. This is done so that the buffer does not disturb the tissue on the slide since the needle of the volume adjust nozzle 388 is directly above the slide and the wash buffer is dropped onto the slide. A precise amount of buffer is able to be placed on the slide. This is based on the amount of pressure in the wash buffer bottle, the amount of time the valve 248G for the volume adjust line is open, and the amount of flow through the restrictor 268. Based on these parameters, the amount of volume placed on the slide may be adjusted by changing the dial nozzle which controls the amount of time the valve for the volume adjust line is open. In the alternative, the amount of time the valve is open may be adjusted using a potentiometer.

In operation, the volume adjust 266 is more accurate when it is turned on for more than 60 mSec. Operating the volume adjust 266 less than 60 mSec makes the dispensing of the buffer less accurate. Therefore, when designing a system which combines both the consistency pulse with the volume adjust, the consistency pulse should leave a volume of liquid on the slide low enough so that the volume adjust may be turned on for more than 60 mSec. In order to accomplish this, the consistency pulse is designed to leave a minimal amount of liquid on the slide by using the dual rinse bottom nozzle 264 and the two valves 248I and 248J. In practice, after the consistency pulse using the dual rinse bottom nozzle 264 and the two valves 248I and 248J, there is 180±20 µL. By turning on the volume adjust for approximately 100 mSec, the volume on the slide is increased to approximately 270 µL.

Referring to FIGS. 8B and 8C, there are shown side views of the angles of the dual rinse top nozzle 263 and dual rinse bottom nozzle 264, respectively, as shown in FIG. 8A. The angle, as described previously, is 35 degrees from the horizontal for the outlet of the dual rinse top nozzle (263) is 25 horizontal for the outlet of the dual rinse bottom nozzle (264). These angles may be varied in order to modify the amount and/or variation of liquid left on the slide after the consistency pulse.

Referring to FIG. 8D, there is shown a side view of one embodiment of the volume adjust as shown in FIG. 7. The needle 388 of the volume adjust is composed of a stainless steel with a 90 degree needle. Fluid therefore goes at a downward angle and drops onto the slide. The connector pieces which connect the needle 388 to the acrylic block 392 of the volume adjust are also composed of stainless steel. The stainless steel is used since it does not react with the wash buffer. At the back of the acrylic block 392 is a connector 394 which connects to the volume adjust line of FIG. 6A. At the side of the acrylic block is a connector 396 which connects to the Liquid Coverslip™ line of FIG. 6A.

Figure 9A:
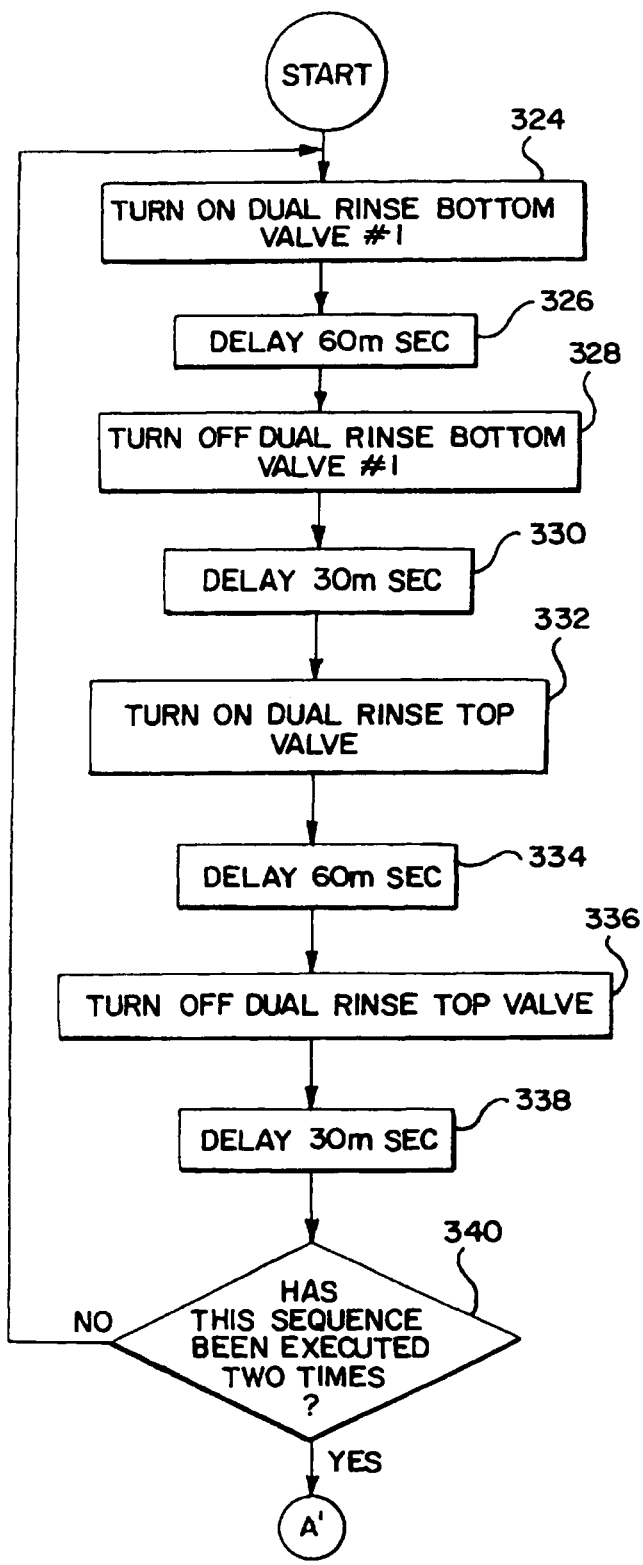
FIG. 9 is a flow chart of the dual rinse, the consistency pulse and the volume adjust steps.
Figure 9B:
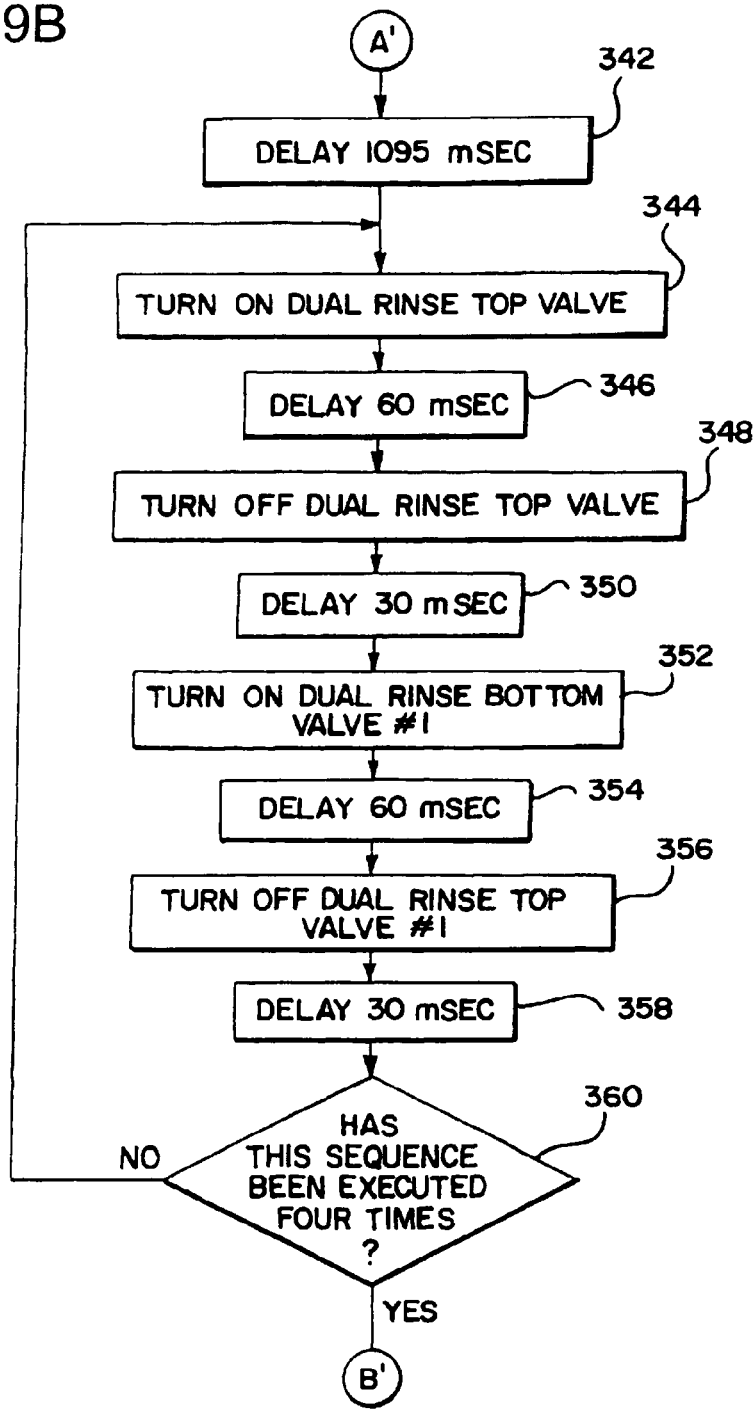
Figure 9C:
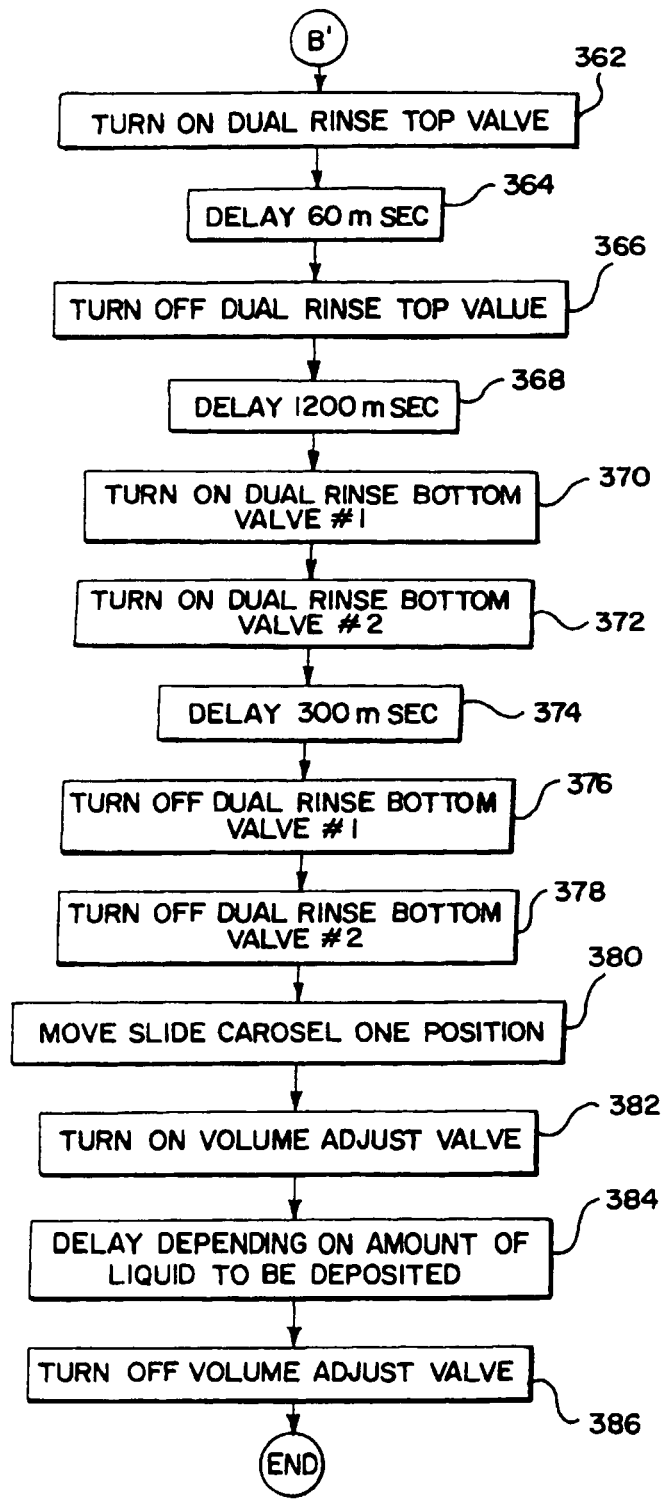

Referring to FIG. 9, there is shown a flow chart of the dual rinse, the consistency pulse and the volume adjust steps. For the dual rinse step, one of the dual rinse bottom valves (248I or 248J) is first turned on 324, the microcontroller 36 waits for 60 mSec 326, and the dual rinse bottom valve (248I or 248J) is turned off 328. The microcontroller 36 then delays for 30 mSec 330. The dual rinse top valve (248H) is then turned on 332, the microcontroller 36 waits for 60 mSec 334, and the dual rinse top valve (248H) is turned off 336. The microcontroller 36 then delays for 30 mSec 338. This sequence is repeated two times 340. Then, the microcontroller 36 waits 1100 mSec 342. Then the dual rinse top valve (248H) is turned on 344, the microcontroller 36 waits for 60 mSec 346, and the dual rinse top valve (248H) is turned off 348. The microcontroller 36 then delays for 30 mSec 350. One of the dual rinse bottom valves (248I or 248J) is first turned on 352, the microcontroller 36 waits for 60 mSec 354, and the dual rinse bottom valve (248I or 248J) is turned off 356. The microcontroller 36 then delays for 30 mSec 358. This sequence is repeated four times 360. Then the dual rinse top valve (248H) is turned on 362, the microcontroller 36 waits for 60 mSec 364, and the dual rinse top valve (248H) is turned off 366. The microcontroller 36 then waits 1200 mSec 368.

In the preferred embodiment, the dual rinse step begins with a bottom-top, bottom-top rinse cycle, and then a top-bottom, top-bottom, top-bottom, top-bottom rinse cycle. In this manner, the slide is cleaned better. This switching of the dual rinse step, starting with one set of nozzles (in the preferred embodiment, the dual rinse bottom valve), and in the next step, starting with the other set of nozzles (in the preferred embodiment, the dual rinse top valve), allows for quicker cleaning of the slide while using less buffer.

For the consistency pulse step, both the dual rinse bottom valves (248I and 248J) are turned on 370, 372, the microcontroller 36 then delays 300 mSec 374, and both the dual rinse bottom valves (248I and 248J) are turned off 376, 378. For the volume adjust step, after the slide carousel 24 is moved into position 380, the valve 248G for the volume adjust line is turned on 382. The microcontroller 36 waits, depending on the amount of liquid to be deposited on the slide 384. Then, the valve (248G) for the volume adjust line is turned off 386. Delays in between the dual rinse step, consistency pulse step, and volume adjust step are inserted in the steps above in order to minimize the possibility of having too many valves on in the system at the same time. If this occurs, this drops the pressure and, in turn, reduces the force of liquid of wash buffer and Liquid Coverslip™.

Figure 10:
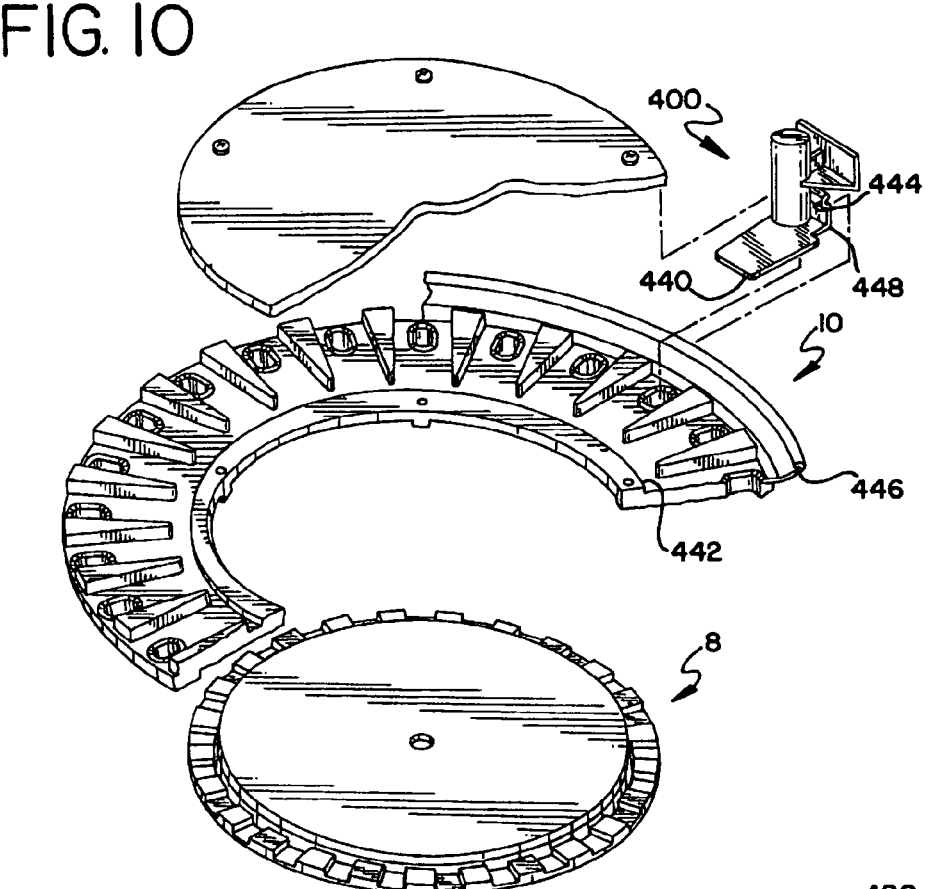
FIGS. 10 and 11 illustrate the mounting of a liquid dispenser on a reagent tray and the manner in which a reagent tray is engaged with a drive carousel.
Figure 11:
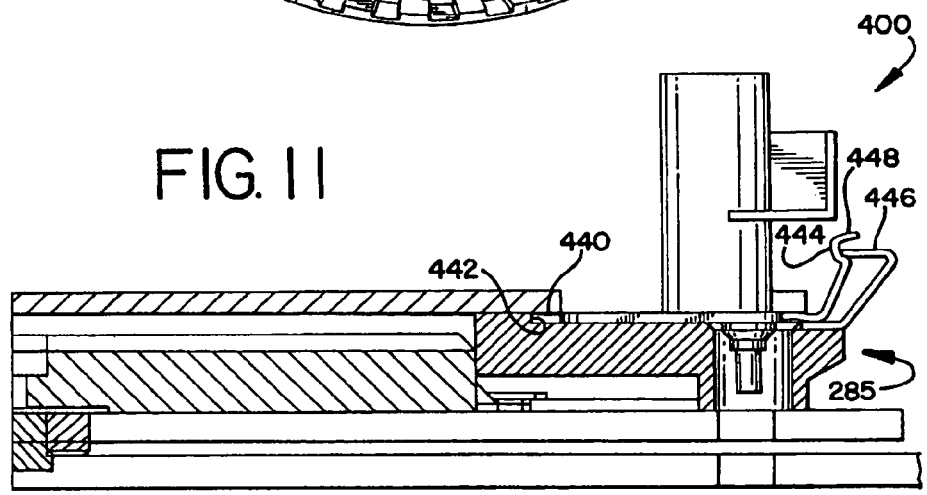

FIGS. 10 and 11 illustrate the manner of mounting a liquid dispenser 400 in a reagent tray which is engaged in the reagent carousel 8. The foot 440 is initially inserted into a circular U-shaped groove 442 formed in the reagent tray 10. In an alternative embodiment, the foot is inserted into a rectangular shaped groove. Groove 444 of spring member 448 engages a circumferential lip 446 of the reagent tray 10. FIG. 11 shows a cross sectional view of the liquid dispenser 400 after it has been mounted on the reagent tray 10 showing in particular the manner in which foot 440 fits into groove 442 and showing the flexing of spring member 448 to hold the liquid dispenser 400 firmly in place. To remove the liquid dispenser 400, spring member 448 is simply bent inward slightly so that the groove 444 clears the lip 446, and the foot 440 is withdrawn from groove 442.

Referring to FIG. 12A, there is shown an elevational cutaway view of a prefilled liquid dispenser 400 in the extended position. FIG. 12B shows an elevational cutaway view of a user fillable liquid dispenser 400 in the extended position. The main difference between the prefilled and customer fillable dispensers is the substitution of a flip cap 402 to replace the snap cap 404. The liquid dispenser 400 has a reservoir chamber 410, which stores the liquid, and a dispense chamber 412, whereby the reservoir chamber 410 is above the dispense chamber 412. The reservoir chamber 410 is substantially in line with the dispense chamber, and in the preferred embodiment, coaxial with the dispense chamber 412.

Previous liquid dispensers included a reservoir chamber 410 which was to the side of the dispense chamber 412 requiring a connecting or horizontal section which connected the reservoir chamber 410 with the dispense chamber 412. In addition to potential problems of clogging of the horizontal section, the previous design was more difficult to manufacture. In particular, the side-by-side design required that the molding process of the horizontal or connecting piece be carefully controlled so that all sides of the connecting piece interact correctly with the reservoir chamber 410, the dispense chamber 412, and the ball chamber 432 and nozzle 430. As described subsequently, the ball chamber 432 includes a check ball 426 which seats in the upper part of the ball chamber 432 during a portion of the operation of the liquid dispenser 400. In previous designs, the coupler was formed via a T-shaped chamber a horizontal chamber abutting two vertical pieces. At the intersection of the pieces, the ball seat area was formed. In manufacturing this coupler, the consistency of the T-shaped piece varied so that the ball seat area was, at times, difficult to manufacture properly. In the present invention, the liquid dispenser 400 requires no horizontal or connecting portion between the reservoir chamber 410 and the dispense chamber 412. The reservoir chamber 410 is on top of dispense chamber 412 and, in the preferred embodiment, the reservoir chamber 410 is coaxial with the dispense chamber 412. Since the flow is substantially in one line or vertical, the T-shaped piece is removed. Moreover, the ball seat area is replaced by a check valve ball insert 424 which is a separate and smaller molded piece and therefore can be controlled, from a manufacturing standpoint, better than in previous designs.

Figure 18:
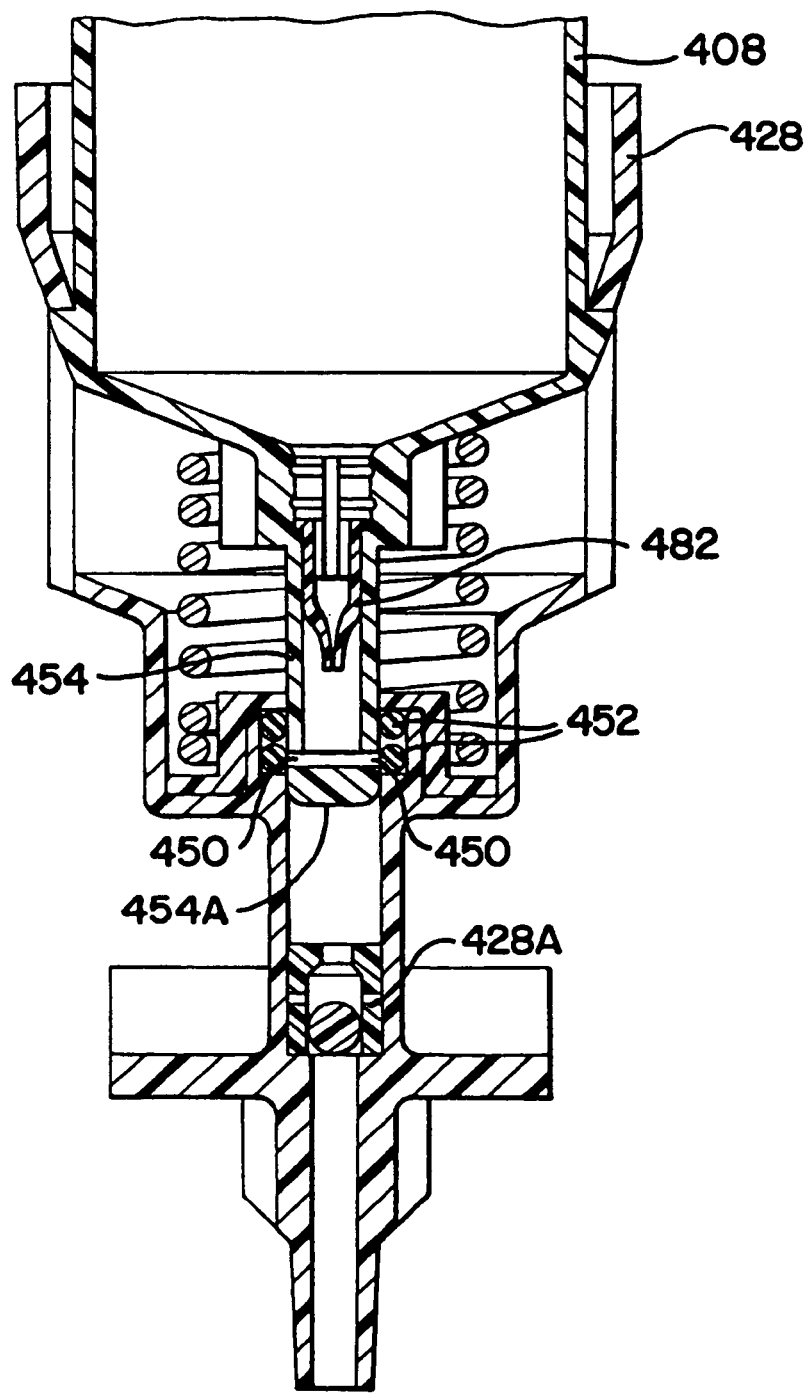
FIG. 18 is an alternative embodiment of a cutaway view of the lower portion of the barrel, duckbill, duckbill insert, quad seal, check ball, check ball insert and coupler of a liquid dispenser.

In the preferred embodiment, the reservoir chamber 410 shape is as shown in FIGS. 12A and 12B. The reservoir shape may also be funnel-like or any other shape which drains the fluid through the connecting means between the reservoir chamber 410 and the dispense chamber 412. The connecting means between the reservoir chamber 410 to the dispense chamber 412 in the preferred embodiment is a valve, such as a duckbill 416 which has a means to sense pressure differentials. In alternate embodiments, the connecting means is any device which transfers liquid in one direction (from the reservoir chamber 410 to the dispense chamber 412) and which passes liquid based on a pressure differential. This includes using an umbrella valve. Further, in an alternative embodiment as shown in FIG. 18, there is shown a barrel 408 which has a lower section which acts as a piston 454 at its lower end, similar to FIGS. 12A-12C; however, the liquid dispenser does not have duckbill valve. Instead, at the lower section of the barrel, in the piston area, there are holes 450 in the side of the barrel 408 which contact O-ring seals 452. In this manner, when the barrel 408 is pushed downward, the holes 450 are exposed, expelling liquid and dispensing liquid from the reservoir chamber 410. Further, the end of the piston 454A is closed thereby sealing the bottom of the barrel 408 except for the holes 450.

Liquid is ejected from the dispense chamber 412 by exerting a downward force on the cap, against the force of the compression spring 418. This forces the barrel 408 downward until it reaches the stop 420 which prevents the barrel 408 from further downward movement, as shown in FIG. 12C. When the liquid dispenser 400 is mounted on a reagent tray 10, as described in FIGS. 10 and 11, the downward force on the cap 404 is applied by the dispense cylinder extend air line, as described in FIG. 6A, or by some other means to push the barrel 408 downward. The downward movement of the barrel 408, including the lower portion of the barrel which acts as a piston, expels liquid from the dispense chamber 412. In this manner, problems associated with a piston which is a separate piece in the dispense chamber 412 are avoided.

Figure 13A:
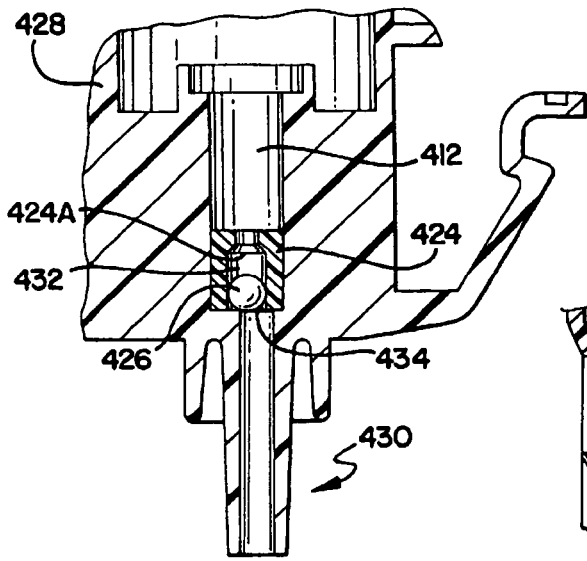
FIG. 13A is a cutaway view of the ball chamber and nozzle.

As the spring 418 expands, the barrel 408 moves upward and the check ball 426 moves upward as well. Referring to FIG. 13A, there is shown a detailed view of the ball chamber 432 and nozzle 430. The coupler 428 is formed where a hole in the coupler is offset for ball chamber 432 so that an inner edge of nozzle 430 protrudes into the outlet of ball chamber 432. Ball chamber 432 contains a check ball 426 which fits loosely against the cylindrical surface of ball chamber 432 and is free to move between an uppermost position and a lowermost position. In its uppermost position, check ball 426 mates with the check valve ball seat 424, thereby preventing liquid flow in the direction from nozzle 430 to dispense chamber 412. At its lowermost position, the check ball 426 is restrained by inner edge of nozzle 430 and prevented from falling into nozzle 430. This does not prevent liquid from flowing from ball chamber 432 to nozzle 430, however.

Using the above described structure as a basis, the operation and unique characteristics of liquid dispenser 400 will now be described. At the beginning of a dispense stroke, the liquid dispenser 400 is in the positions shown in FIGS. 12A and 12B. When liquid is to be dispensed, a downward force is applied against cap 402. This overcomes the force of compression spring 418 and forces the barrel 408 downward until it reaches the seat of the stop 420, thereby dispensing a predetermined volume of liquid equal to about 100 μL. This is equal to the liquid volume of the area that the barrel 408 moves down minus the "suck back" (which is the amount of fluid that travels past the check ball on the upstroke of the barrel 408 before the check ball 426 shuts off the flow). The liquid flows from dispense chamber 412 into ball chamber 432. The downward flow through ball chamber 432 forces check ball 426 to its lowermost position, abutting edge, but this does not prevent flow in this direction and the measured amount of liquid is ejected from nozzle 430.

When the barrel 408 has reached its lower extreme position, the downward force on cap 402 is released, by the microcontroller 36 actuating the valve 248B for the dispense cylinder retract air line, as described in FIG. 6A, and compression spring 418 takes over, forcing barrel 408 and cap 402 in an upward direction. Liquid begins to be sucked into dispense chamber 412, which was described previously as the "suck back."

It is here that the interplay of check valve ball seat 424 and ball chamber 432 is described. Check valve is a duck bill valve 416, which requires a predetermined threshold pressure differential in order to permit flow in the forward direction. In contrast, check ball 426 moves freely within ball chamber 432, and therefore provides essentially no resistance to liquid flow from nozzle 430 until it reaches its sealing position at the check valve ball seat 424. When the dispenser operation is completed, the liquid flow has forced check ball 426 to its lowermost position, abutting edge 434. As the upward movement of the barrel 408 begins to draw liquid back into dispense chamber 412, the upward flow of fluid in ball chamber 432 pulls check ball 426 upward until it reaches check valve ball seat 424, where it cuts off any further liquid flow toward dispense chamber 412. Until check ball 426 reaches the check valve ball seat 424, however, there is virtually no resistance to liquid flow from nozzle 430, and therefore no pressure differential is created across duck bill check valve 416 sufficient to cause liquid flow from reservoir chamber 410 to dispense chamber 412.

The volume of liquid which flows from nozzle towards dispense chamber 412 ("suck back") while check ball 426 is moving from its lowermost to its uppermost position is preselected to be a volume exactly equal to the volume of the hanging drop left at tip at the end of the dispense cycle. Thus, the drip is effectively drawn back into nozzle 430 and an internal meniscus forms at tip.

When check ball 426 reaches the check valve ball seat 424, it shuts of further flow from nozzle 430 into dispense chamber 412. This immediately creates a pressure differential across check valve and causes liquid to flow from reservoir chamber 410 into dispense chamber 412. The suction generated in dispense chamber 412 keeps check ball 426 firmly seated against the check valve ball seat 424 and prevents any further flow from nozzle 430. When compression spring 418 has forced barrel 408 upward, as shown in FIGS. 12A and 12B, the liquid dispenser 400 is ready for another dispense cycle. Check ball 426, being made of a material slightly more dense than the liquid, falls through ball chamber 432 until it make contact again with edge 434.

Figure 13B:
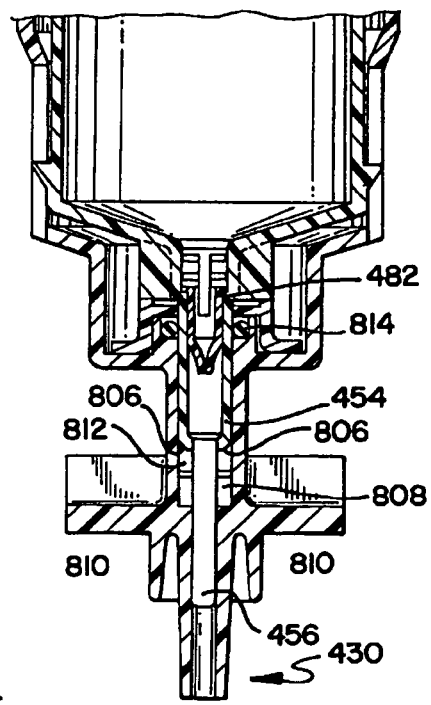
FIGS. 13B and 13C are front and side cutaway views of the lower portion of the barrel with an extension section.
Figure 13C:
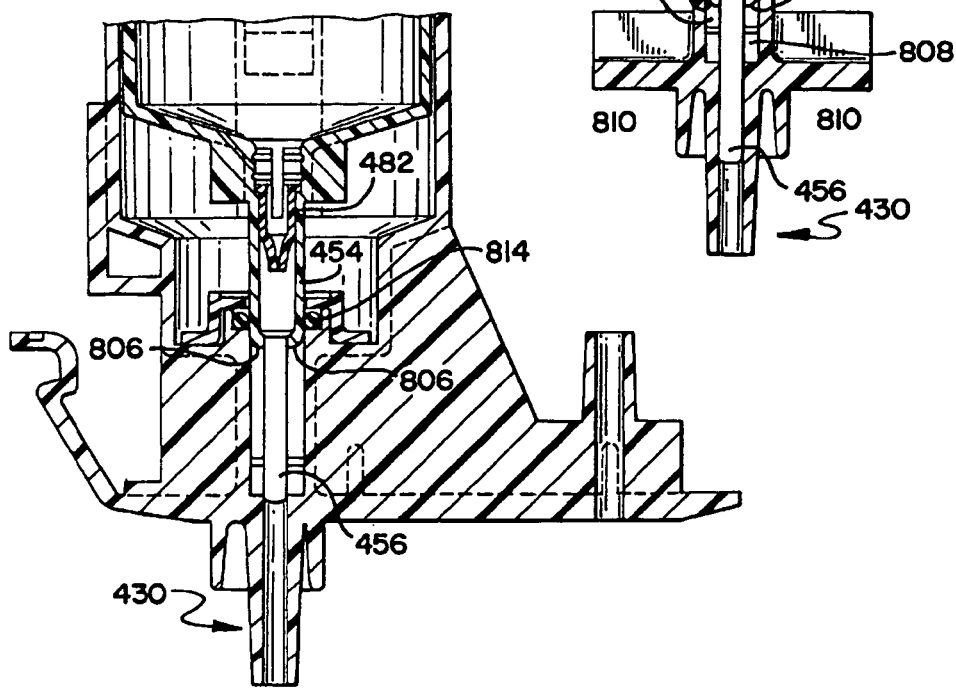

Referring to FIGS. 13B and 13C, there is shown a front and side cutaway of the lower portion of the liquid dispenser 400, respectively, in an alternative embodiment of the invention wherein the check valve ball seat 424 and check ball 426 are removed. In order to retract a hanging drop from the edge of the nozzle 430, the piston 454 on the end of the barrel 408 has an extension piece 456 connected to it. In this manner, when the barrel 408 is raised upward, the extension piece 456 moves upward as well, thereby retracting any drops on the edge of the nozzle 430.

Referring to FIGS. 14A and 14B, there are shown exploded views of a cutaway of a prefilled and user fillable liquid dispenser 400, respectively. As described previously, the difference between the prefilled and the user fillable liquid dispensers is the snap cap 404, as shown in FIGS. 14A and 14B. Fluid can be filled into the reservoir through a fill hole and subsequently closed using a snap cap 404 in order to close the system. For prefilled liquid dispensers, the snap cap 404 is permanently attached over the fill hole after filling. The fill hole and the snap cap 404 are matched using a luer fitting design in order to be a tight seal, as shown in FIG. 16. The user fillable liquid dispenser 400 utilizes a living hinge design and luer slip design between the fill hole and the flip cap 402. The cap 406, as previously described, is sonically welded to the barrel 408. The cap 406 also has a vent 460, which is described subsequently with respect to FIG. 16. The duckbill insert 414 holds the duckbill 416 in place and creates a seal so that fluid cannot drip either from the dispense chamber 412 to the reservoir chamber 410 or from the reservoir chamber 410 to the dispense chamber 412. Further, the duckbill insert 414 has a protrusion, or a nipple, which holds the duckbill to it for ease of assembly, as shown in more detail in FIG. 17B. The duckbill 416, which serves as a check valve, is snapped to the duckbill insert 414. The duckbill valve 416 is a one way valve with a high cracking pressure of between 0.6 to 2.5 psi. This acts to hold the liquid in the reservoir chamber 410 since the cracking pressure is greater than the head pressure of the reservoir chamber 410. And, the duckbill passes fluid from the reservoir chamber 410 to the dispense chamber 412 on the upstroke of the barrel 408 while preventing liquid to pass during the downstroke of the barrel 408. The duckbill 416 and duckbill insert 414 are seated in the lower portion of the barrel 408 as shown in FIG. 17A.

Figure 17A:
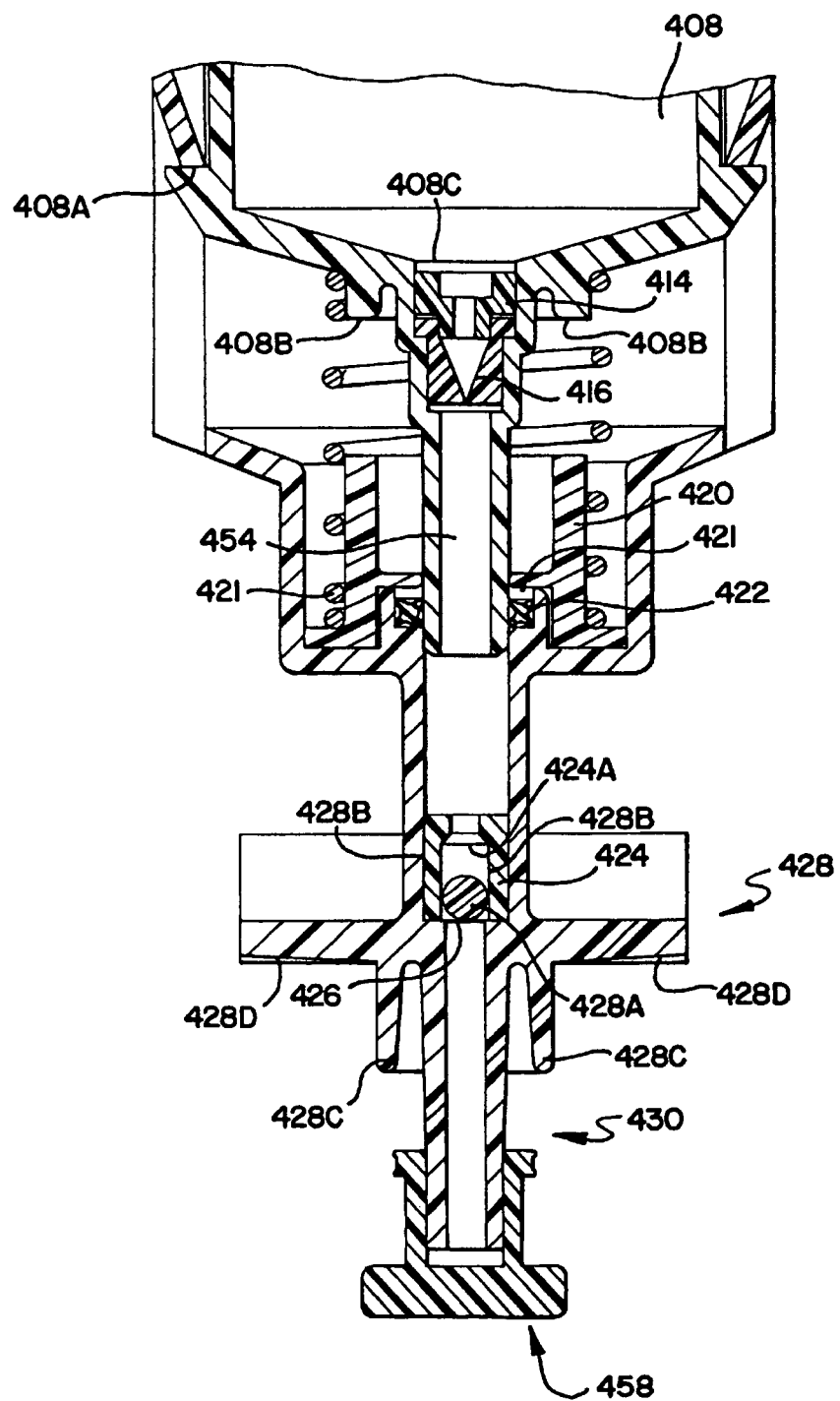
FIG. 17A is a cutaway view of the lower portion of the barrel, duckbill, duckbill insert, quad seal, check ball, check ball insert and coupler of a liquid dispenser.
Figure 17B:
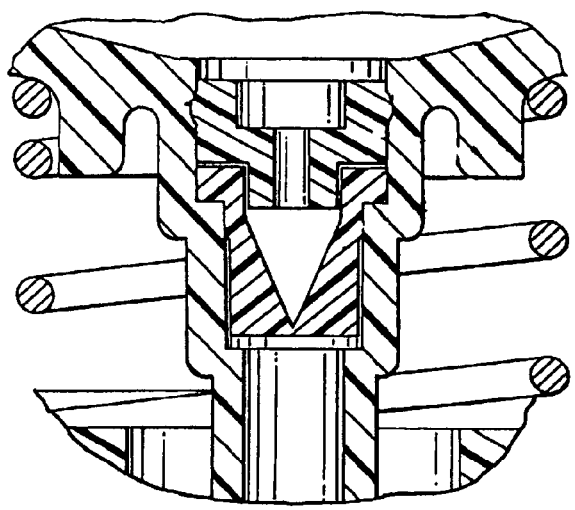
FIG. 17B is a cutaway view of the lower portion of the barrel, duckbill, and duckbill insert of a liquid dispenser.
Figure 17C:
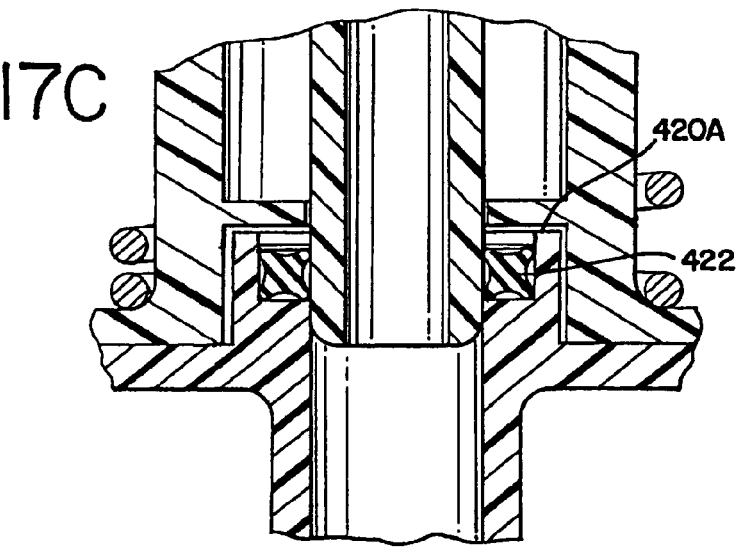
FIG. 17C is a cutaway view of the quad seal of a liquid dispenser.

The spring 418 is a compression spring which expands and contracts based on the movement of the barrel 408. The stop 420, as described previously, stops the downward stroke of the barrel 408. The stop also holds the quad seal 422 in place during movement of the liquid dispenser 400. The manner in which the assembly is assemble, the stop 420 is held in place based on the compression spring 418. The force varies based on the movement of the barrel 408. The stop 420 is held in place, in turn, keeps the quad seal 422 in place via a ledge 420A, as shown in FIG. 17C, on the stop 420. The quad seal 422 ensures that the liquid dispenser 400 is always a closed system thereby keeping the liquid dispenser 400 primed. The check valve ball seat 424 is a separate part from the coupler 428 and is seated inside the coupler 428, being snapped into place by grooves in the chamber of the coupler 428 and by being seated on a ledge 428A, as shown in FIG. 17A. The check valve ball seat 424 has a ball seat 424A on the inside with which to engage the check ball 426 on the upstroke of the barrel 408. Previous liquid dispensers integrated the coupler with the check valve ball seat for the check ball. However, manufacturing of the coupler integrating those functions was difficult, as described above. Therefore, processing is simplified by separating the check valve ball seat 424 from the coupler 428. The inner cavity 432 of the check valve ball seat 424, which engages the check ball 426, may then be manufactured more easily. The check ball 426 is made of a borosilicate (which is a type of glass). In an alternative embodiment, a check ball 426 composed of rubber may be used. In certain instances, a rubber ball may seat better in the plastic check valve ball seat 424, provided there is no chemical interaction of the rubber ball with the reagents.

Assembly and filling of the liquid dispenser 400 is simple based on the invention. The duckbill 416 and duckbill insert 414 are placed in the lower part of the barrel 408. The cap 406 is welded to the barrel. The check ball 426 is placed, the check valve ball seat 424 is snapped and then the quad seal 422 is inserted into the coupler 428. The stop 420 and the spring 418 are inserted into the coupler 428 and the coupler 428 is snapped on to the barrel 408. The barrel 408 is filled with reagent and the liquid dispenser 400 is primed. The snap cap 404, for prefilled liquid dispensers, or flip cap 402, for user fillable liquid dispensers, is placed on the top of the dispenser and the nozzle cap 458 is placed on the output of the nozzle 430 on the coupler 428.

Further, the present invention allows for easier manufacture and filling of the reagents in the liquid dispenser 400. Previous liquid dispensers required gluing and sonic welding of many pieces requiring a certain level of skill and training. In contrast, the liquid dispenser of the present invention requires snapping in of pieces and only the sonic welding of the vent 460 to the cap 406 and the cap 406 to the barrel 408. Moreover, the filling of the reagents in the liquid dispenser 400 is easier in the present invention. In previous liquid dispensers, the liquid dispenser is assembled except for the piston, piston guide and cap. The reservoir chamber 410 is filled with reagent. The piston is then placed in the reservoir chamber 410 and any leftover fluid on top of the piston is evacuated. Finally, the cap is sonically welded onto the top of the barrel 408. In the present invention, since there is no piston in the reservoir chamber 410, there is no need to evacuate the area on top of the piston. Instead, the cap 406 is first sonically welded to the barrel 408, and then the reagents are added to the reservoir chamber 410. In this manner, there are fewer steps in the filling of the dispenser. Moreover, in the present invention, some of the more manufacturing sensitive parts are smaller, thereby making manufacturing easier. In the preferred embodiment, the material used is high-density polyethylene. Under these conditions, smaller parts have a higher level of dimensional stability. Therefore, smaller components, such as the check valve ball seat 424 (which is, in the present invention, a separate component from the coupler 428) are able to be processed more consistently.

Figure 19:
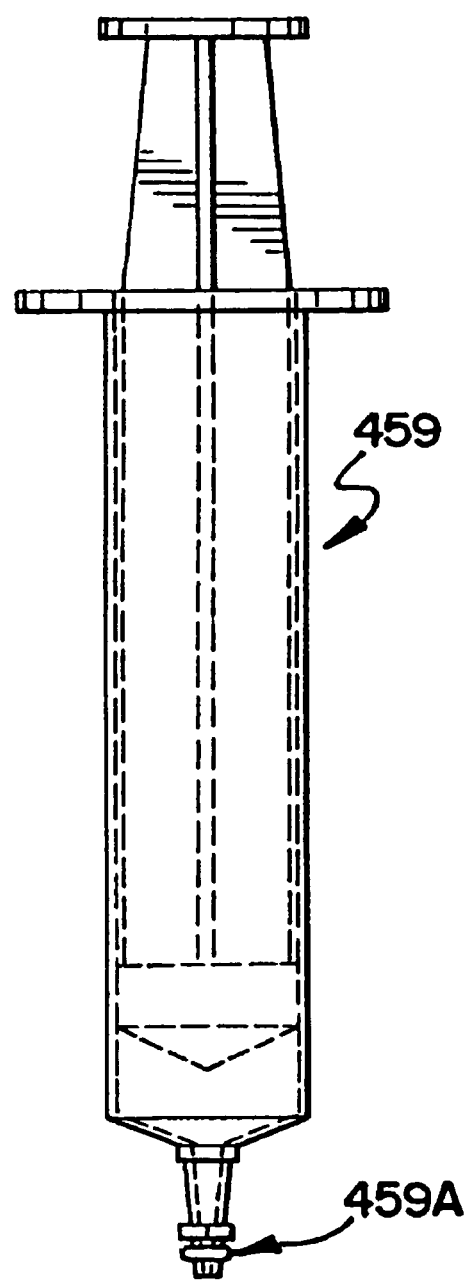
FIG. 19 is a cutaway view of a syringe with a restrictor for use in the nozzle of the coupler.

Referring to FIGS. 15A and 15B, there are shown side views of a prefilled liquid dispenser 400 and customer fillable liquid dispenser 400, respectively. Both types of dispensers have barcode labels which are read by the barcode reader, as described above. In order to allow the customer to fill the liquid dispenser 400 with reagent, the snap cap 404 is replaced by a flip cap 402 which varies in two ways from the snap cap: (1) the flip cap has an attachment to the cap; and (2) the flip cap has a protrusion 402A which acts as a thumbpad to prop open the flip cap 402. In previous liquid dispensers, the liquid dispenser had to be inverted in order to prime the syringe. The customer was required to first fill up a transfer syringe manually upside down, push on an epindorf syringe to force fluid from the reservoir chamber 410, through the connecting section between the reservoir chamber 410 to the dispense chamber 412, to the dispense chamber 412. The customer had to then pump the plunger, at least 6 to 8 times, until fluid came out of the nozzle which did not have any bubbles. In the present invention, the customer opens the flip cap, fills the reservoir chamber 410, and closes the flip cap. The customer, without turning the liquid dispenser upside down, uses a typical syringe 459, as shown in FIG. 19, to prime the liquid dispenser 400. The syringe 459 has a restrictor 459A which has an internal diameter of approximately 5 thousandths of an inch. The syringe 459 is placed inside the nozzle 430 of the coupler 428 and the syringe plunger is expanded to draw liquid from the reservoir chamber 410 and the dispense chamber 412. To prime the liquid dispenser 400 more quickly, the barrel 408 is pushed down, and is released simultaneously when the syringe plunger is expanded. In this manner, there is significantly less waste of reagent. In the previous liquid dispensers, the pumping of the plunger 6-8 times wasted reagent. In the present liquid dispenser 400, any reagent is sucked into the syringe 459. Because the syringe 459 is clean, its contents may be placed back into the reservoir chamber 410 through the flip cap 402.

Figure 16A:
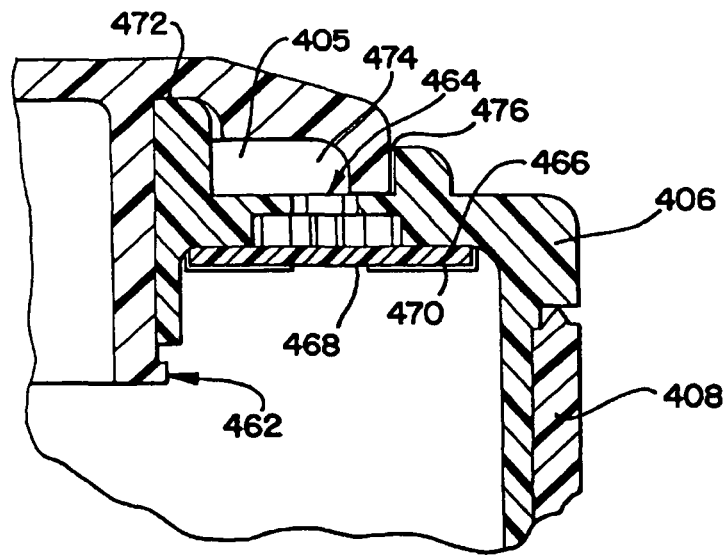
FIG. 16A is a cutaway view of the cap and vent of a prefilled liquid dispenser according to one embodiment.

Referring to FIG. 16A, there is shown a cutaway view of the cap 406 and vent 460 of a liquid dispenser 400. The vent is the component adjacent the top of the cap and includes the vent area 464, vent material 466, and backing 468. The cap 406 and snap cap 404 (or flip cap 402 for user fillable liquid dispensers) are luer fitting design so that the cap 406 and snap cap 404 portion which engage each other to seal the fill hole is conical. At the lower portion of the conical section of the snap cap 404 is a ring or a lip 462 which is used to snap the snap cap 404 into place. In this manner, the snap cap 404 is pushed down until it locks into the cap 406. The snap cap 404 has a curved section 472 which abuts against a curved section of the cap thereby stopping the snap cap 404 at that point. The snap cap 404 also engages the cap 406 to form a hollow section air space 474 which is adjacent to the vent area. This hollow section air space 474 forms a ring, so that regardless of the orientation of the snap cap to the cap, a hollow section is adjacent to the vent area 464 (which is approximately 70 thousandths of an inch or less). Further, the outside diameter of the snap cap 404 is slightly smaller than the inner diameter of the cap 406 so that a small air gap 476 is formed adjacent to the hollow section air space 744 to the outside of the dispenser. The hollow air gap 474 serves as a buffer between the outside of the dispenser and the vent 460.

Figure 16B:
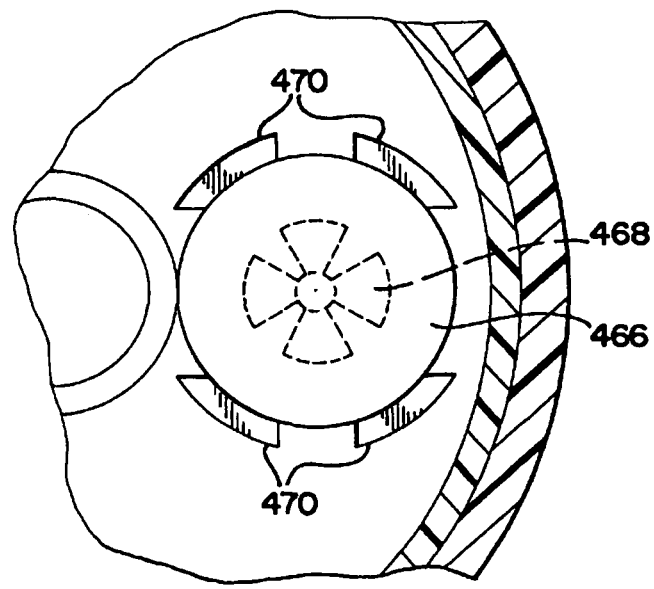
FIG. 16B is an underside view of the cap and vent of FIG. 16A.

The vent 460 is used as a means to allow air to flow both into and out of the reservoir chamber 410. The vent 460 equalizes the pressure in the reservoir chamber 410 with the pressure in the atmosphere. The vent 460 is a hydrophobic vent which allows air to flow through the vent while keeping fluid trapped inside the reservoir chamber 410. The vent is composed of a filter material 466 such as a teflon material with a polypropylene backing to sonically weld the vent to the cap. The vent opening or area, as described previously, is approximately 70 thousandths of an inch. The pressure inside the reservoir chamber 410 is constant, even though the level of reagent may be changing inside the reservoir chamber 410 since air is allowed to flow into the reservoir chamber 410. Moreover, some reagents produce a by-product of gas (called outgassing). In the event that a reagent outgasses, the hydrophobic vent 460 allows gas through the vent 460, thereby avoiding any pressure build-up inside the reservoir chamber 410. In this manner, previous liquid dispensers which required a piston to exert force on the liquid in the reservoir chamber 410 may be removed. The piston in the previous design suffered from several drawbacks. First, certain reagents (such as proteins) may stick to the barrel. Additionally, the interaction between the piston and the barrel relying on lubricants, certain reagents that are composed, in part, of detergents. The detergents interfere with the lubrication between the piston and the barrel. Both effects interfere with the performance of the liquid dispenser, thereby giving inconsistent dispensing of liquid. Further, outgassing interacts with the piston either to increase the flow out of the reservoir chamber 410 or to create a compressible air gap between the piston and the main section of the reservoir chamber 410. Referring to FIG. 16A, there are protrusions 470 on the inside upper portion of the cap which are used to align the piece of vent material. The vent 460 is therefore centered on top of that upper portion of the cap. Referring to FIG. 16B, there is shown an underside view of the vent 460. Included with the vent 460 is a platform 468 for the vent 460, star-shaped in design, which holds the vent 460 flat. When air is passing through the vent 460, particularly when outgassing, the vent 460 has a tendency to flex which may damage the teflon in the vent. In order to minimize flexing of the vent 460, the platform 468 is adjacent to the vent. Therefore, the surface area of the vent may still be relatively large but still have a grid support to stabilize the vent 460 during outgassing. The platform 466 is star-shaped due to ease of molding.

Figure 16C:
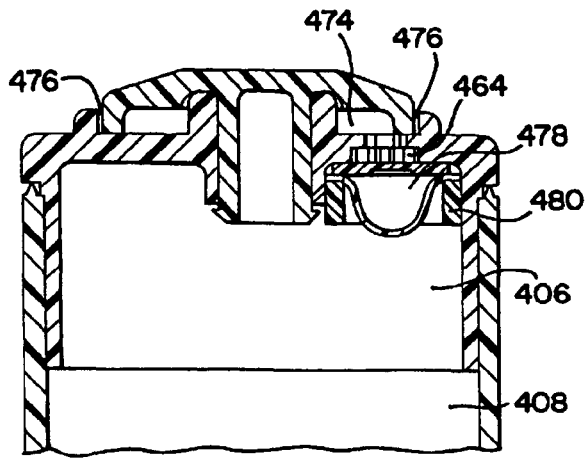
FIG. 16C is a cutaway view of the cap and vent of a prefilled liquid dispenser with a bi-directional duckbill valve.

In an alternative embodiment, as shown in FIG. 16C, the vent may be substituted with a bi-directional valve 478 or bi-directional duckbill (or two valves or two duckbills) as another means by which to allow air to flow into and out of the reservoir chamber 410. The bi-directional valve 478 has a bi-directional valve insert 480 for placement of the bi-directional valve 478. The bi-directional valve 478 also has a hydrophobic layer which allows air to flow through the bi-directional valve 478 while keeping fluid trapped inside the reservoir chamber 410. In one direction (air flowing into the reservoir chamber 410), the bi-directional duckbill 478 has a low cracking pressure, in order to equalize the pressure in the reservoir chamber 410 when liquid is dispensed. In the second direction (air flowing out of the reservoir chamber 410), the bi-directional duckbill 478 has a high cracking pressure, in order to alleviate any pressure due to outgassing. The bi-directional duckbill 478 allows air to flow through while keeping fluid trapped inside the reservoir chamber 410. Therefore, the bi-directional duckbill 478 allows air to flow into and out of the reservoir chamber 410 and allows for equalization of the pressure. In practice, a bi-directional duckbill 478 may have less refinement in terms of control when compared to two uni-directional duckbills. If additional refinement is required, the bi-directional duckbill 478 may be replaced by two uni-directional duckbills. Moreover, when integrating the two uni-directional duckbill, with another uni-directional duckbill at the bottom of the barrel, the system becomes a three duckbill system. In this configuration, the duckbill that releases to atmosphere has the lowest cracking pressure, the duckbill that allows air into the reservoir chamber has the highest cracking pressure, and the duckbill 416 that is down in the barrel has a medium cracking pressure.

Figure 16D:
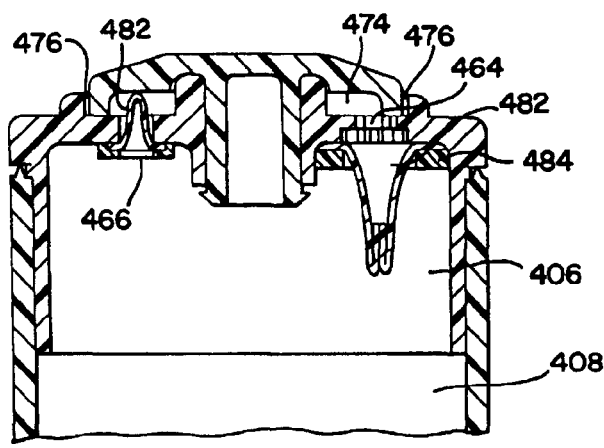
FIG. 16D is a cutaway view of the cap and vent of a prefilled liquid dispenser with a uni-directional duckbill valve.

Pressure differentials caused by outflow of liquid from the reservoir chamber 410, as discussed previously, may make the dispensing of liquid difficult. Further, in certain instances, outgassing may not interfere with the operation of the liquid dispenser 400. Therefore, in another embodiment, as shown in FIG. 16D, the vent 460 may be substituted with a uni-directional valve or duckbill 482, with a duckbill valve insert 484. In the one direction (air flowing into the reservoir chamber 410), the uni-directional duckbill 482 has a low cracking pressure to alleviate pressure due to outflow of liquid from the reservoir chamber 410. In this embodiment, vent material is not required since the air is flowing only into the reservoir chamber.

Figure 16E:
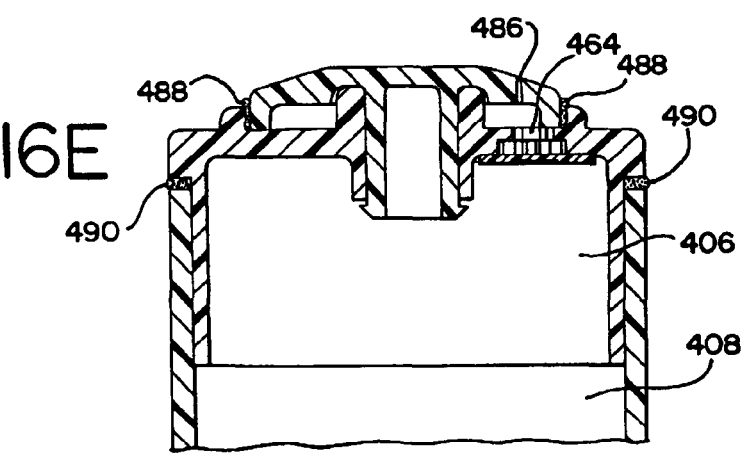
FIG. 16E is a cutaway view of the cap and vent of a prefilled liquid dispenser according to another embodiment.

In a further embodiment, as shown in FIG. 16E, the vent opening 464 may be reduced to approximately 10 thousandths of an inch (from 70 thousandths of an inch) and the snap cap 404, for prefilled liquid dispensers, or the flip cap 402, for user fillable liquid dispensers, may be modified to include a seal 488 where the snap cap 404 or flip cap 402 engages the cap 406. Thus, this alternative embodiment does not have a gap 476 between the snap cap 404 (or flip cap 402) and the cap 406, but instead includes a seal 488. In order for the flow of air into or out of the reservoir chamber 410, there is an opening 486, such as a pin hole or a second vent, placed in the top of the snap cap 404 (or flip cap 402) which is adjacent to the hollow region 474 formed between the snap cap 404 and the cap 406.

Referring to FIG. 17A, there is shown a cutaway view of the lower portion of the barrel 408, duckbill 416, duckbill insert 414, quad seal 422, check ball 426, check valve ball seat 424 and coupler 428 of a liquid dispenser 400. The barrel 408 has protrusions 408A which mate with the coupler in order to maintain the position of the barrel 408 on the upstroke. Otherwise, if the spring pushes the barrel 408 upward too high, the seal, as provided by the quad seal 422, may be broken thereby creating an air path and causing the liquid dispenser 400 to lose prime. The barrel 408 also has a flange 408B which mates with the stop 420 on the downstroke. The barrel 408 also has a pocket 408C, where the duckbill insert 414 is inserted. This pocket acts as a funnel so that no puddles are formed at the bottom of the barrel 408 at the interaction point with the duckbill 416 or duckbill insert 414, thereby minimizing waste. The barrel 408 also has at its lower portion a piston 454 by which liquid is expelled in the dispenser 400. At the lower portion of FIG. 17A is a nozzle cap 458 for engagement with the nozzle 430 of the coupler 428. The nozzle cap 454 and nozzle 430 are matched using a luer fitting design in order to be a fluid tight seal. Referring to FIG. 17B, there is shown a cutaway view of the lower portion of the barrel, duckbill, and duckbill insert of a liquid dispenser. Referring to FIG. 17C, there is shown a cutaway view of the quad seal of a liquid dispenser.

Referring to FIG. 17A, there is shown a cutaway view of the coupler 428. The coupler 428 has grooves 4288 in which the check valve ball seat 424 snaps. The grooves 428B act to prevent any leakage of fluid downward or air upward through the walls of the check valve ball seat 424 and the coupler wall. The coupler 428 also has protrusions 428C, or wings, which ensure that the dispenser is aligned on the reagent tray. For example, if the dispenser is misaligned, the dispense cylinder may not engage the dispenser properly. The coupler also has stabilizing bumps 428D which reduce any rocking back and forth of the liquid dispenser 400.

In another embodiment of the invention, there is provided a means by which to transfer data from the manufacturer to the customer. The manufacturer uses a manufacturing database in order to maintain a record of reagents, master lots, and serial numbers for kits and dispensers. The manufacturing database is an Interbase (client/server) database contained in a single file. The manufacturing database definition consists of domains, tables, views, and triggers. Domains define the variable types and requirements used in tables. Tables define the data that is stored for each record. Views (meta-tables) are accessed as tables but do not contain data. The views collect data from tables. Triggers are programs that are executed on the Interbase server in response to defined events.

Information is stored on the database to define kits (which contain several dispensers) or single dispensers. Each package, whether a kit or a dispenser, will include a barcode identifying the contents. For kits, the barcode will contain the part number, master lot number and serial number. For single dispensers, the barcode will contain the part number, lot number and serial number. Serial numbers are assigned to kits sequentially for each master lot starting at 1 (i.e., the first kit created from each master lot will be assigned serial #1). The package barcodes are separate from the bar codes that appear on the individual dispensers within the package. In particular, in the case of a single dispenser package, the serial on the package barcode label need not match the serial number of the single dispenser contained in the package.

The barcode is encoded with the Code 128 Symbology. The plain text interpretation of the barcode is to appear as standard ASCII text below the barcode. This allows for operator verification of the data obtained by scanning. The three fields on the package label will be fixed in length and combined into a single barcode by concatenation.

Figure 20:
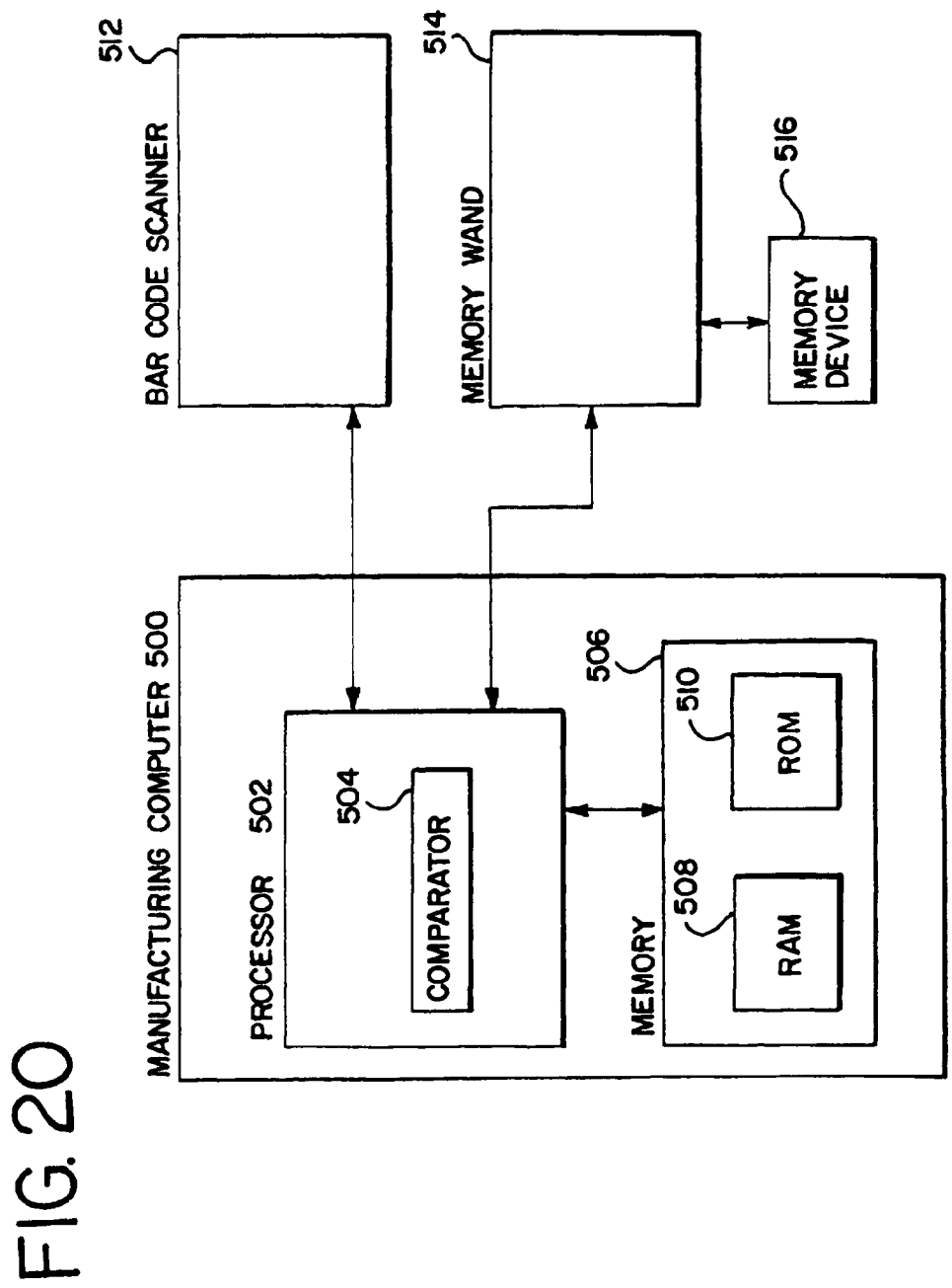
FIG. 20 is a block diagram of the manufacturer's system for programming an external memory device.

Referring to FIG. 20, there is shown a block diagram of the manufacturer's system for programming an external memory device. The manufacturing computer 500 is a typical personal computer, with a processor 502 including a comparator 504, and memory 506 including RAM 508 and ROM 510. As described subsequently, the processor 502 is in communication with a barcode scanner 512 and a memory device 516 such as an EPROM (erasable programmable read only memory). In the preferred embodiment, the processor 502 is in communication with the memory device 516 via a memory wand 514, as described subsequently.

Figure 21A:
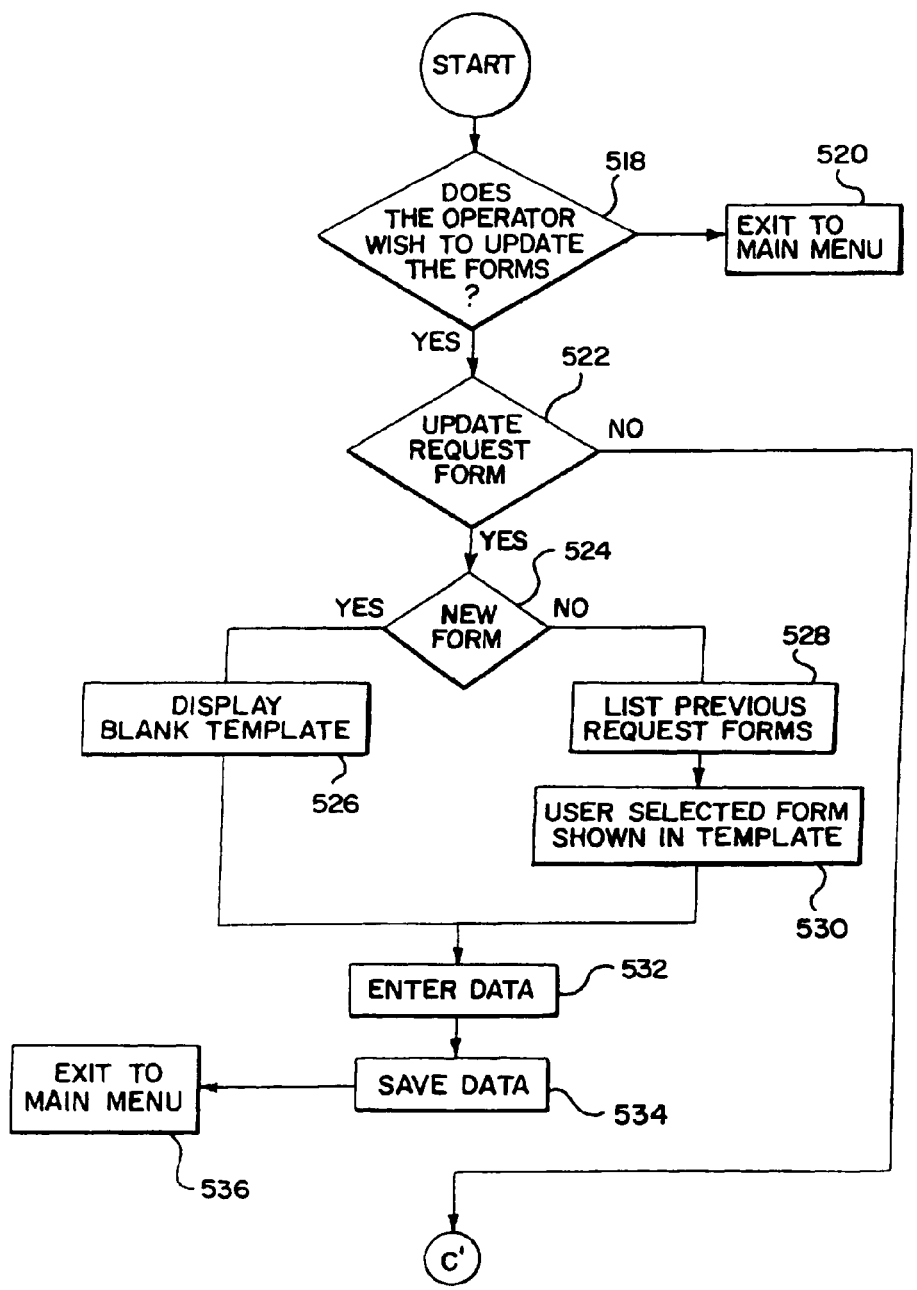
FIG. 21 is a flow chart for updating the forms on the manufacturer's reagent database.
Figure 21B:
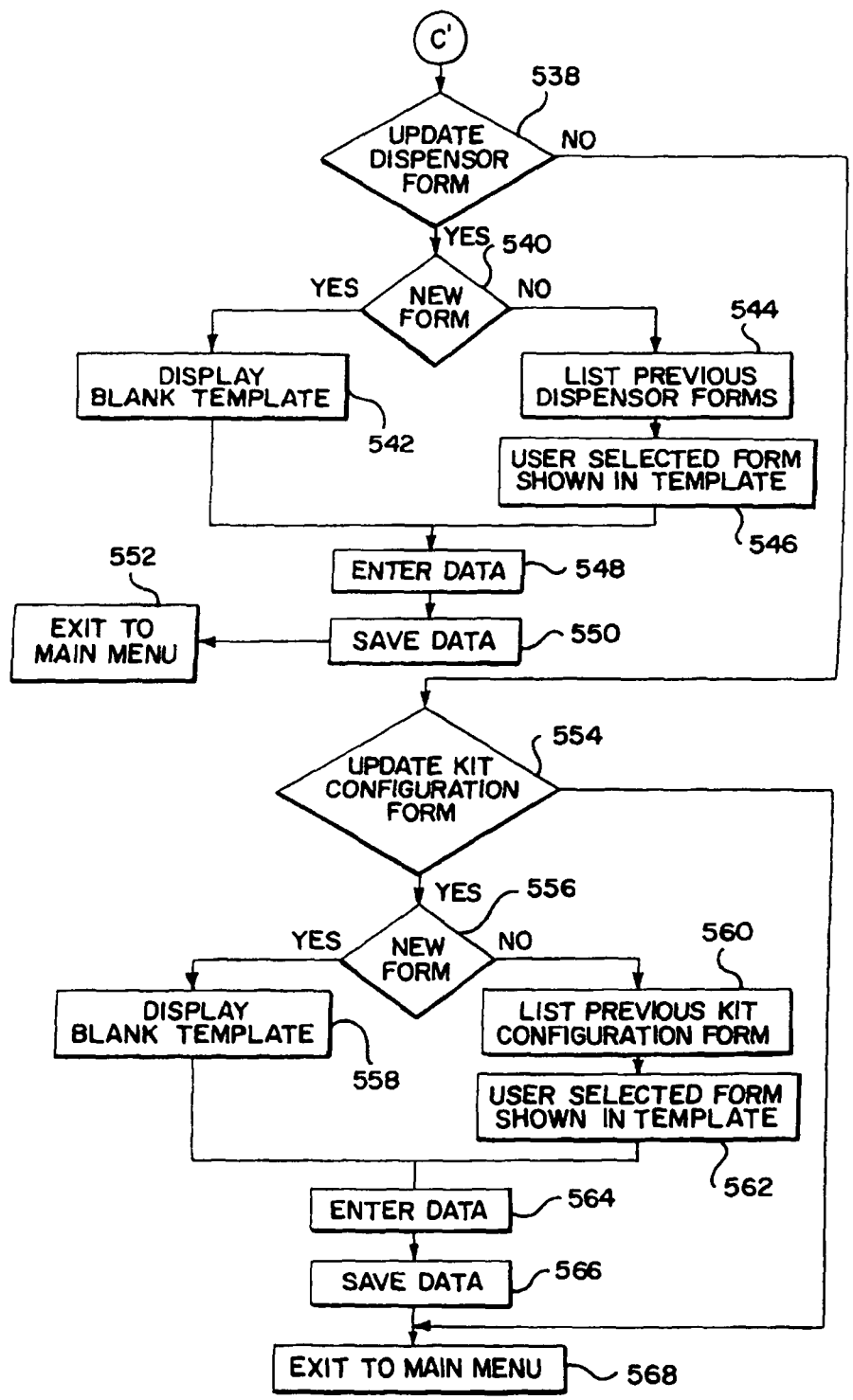

As described in Appendix A, there is software which implements the acquisition of data from registration tables, and stores the data into an external memory device. Referring to FIG. 21, there is shown a flow chart for updating the forms on the manufacturers database. The forms are used as templates for the manufacturing database for kits, dispensers, dispenser models, etc. which are later entered. The forms include reagents, dispenser models, dispensers, kits and filled kits. For example, in the reagent form, data about a particular reagent, such as the reagent name, group name, etc. may be entered. The dispenser models include user fillable and pre-fillable dispensers. Referring to FIG. 20, the operator is asked if he or she wishes to update the reagent form 522. If so, the manufacturing database determines if the reagent form is new or old 524. If new, a blank template is displayed for the operator to enter data 526. If a reagent form is to be modified, the reagent template is displayed 528, 530. The contents are entered or modified and the data saved to the database 532, 534. Likewise, the forms may be modified for the dispenser form, which includes data on the part number, reagent, code, whether the dispenser is prefillable, the dispenser model, whether the reagent is active, etc. The operator is prompted whether the form is new 540, and if new a blank template is displayed 542. If old, the previous dispenser forms are displayed 544 and the user selects a form 546. Data is entered 548 and saved 550. The forms may be modified for the kit configuration as well. The kit configuration includes data on the dispensers included in a kit sent to the end user. This information includes the part number, the description of the kit, whether the dispensers in the kit are active, the number of reagents in the kit, and data on the dispensers in the kit. The operator is prompted whether the form is new 556, and if new a blank template is displayed 558. If old, the previous dispenser forms are displayed 560 and the user selects a form 562. Data is entered 564 and saved 566. The forms interact with one another for ease of updating. For example, if the dispenser model is modified, the dispenser form, which is dependent on the dispenser model, is modified as well. Further, if the dispenser is modified, so is the kit configuration, which in turn depends on the dispenser.

Figure 22A:
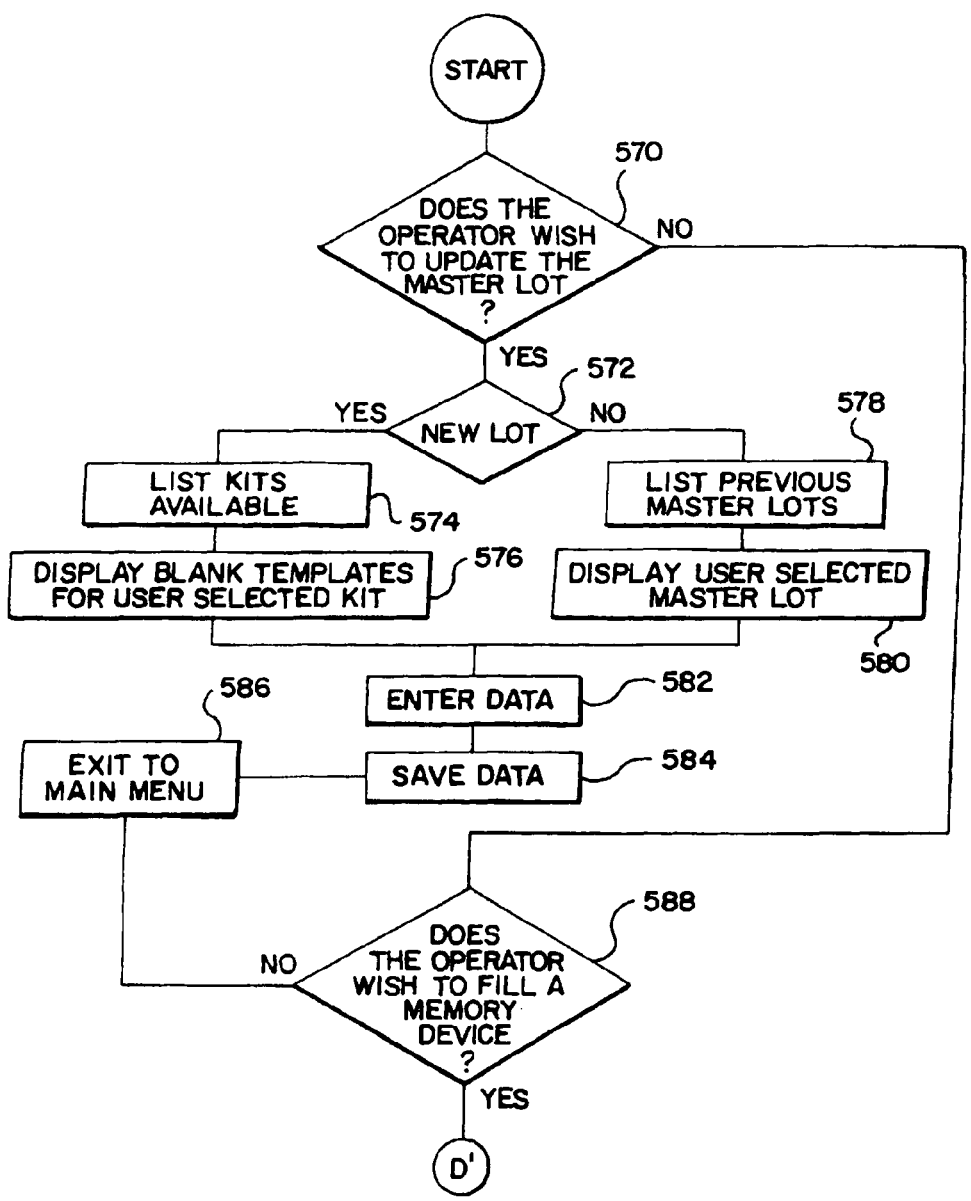
FIG. 22 is a flow chart for updating the master lot on the manufacturers reagent database and for inputting data into a memory device.
Figure 22B:
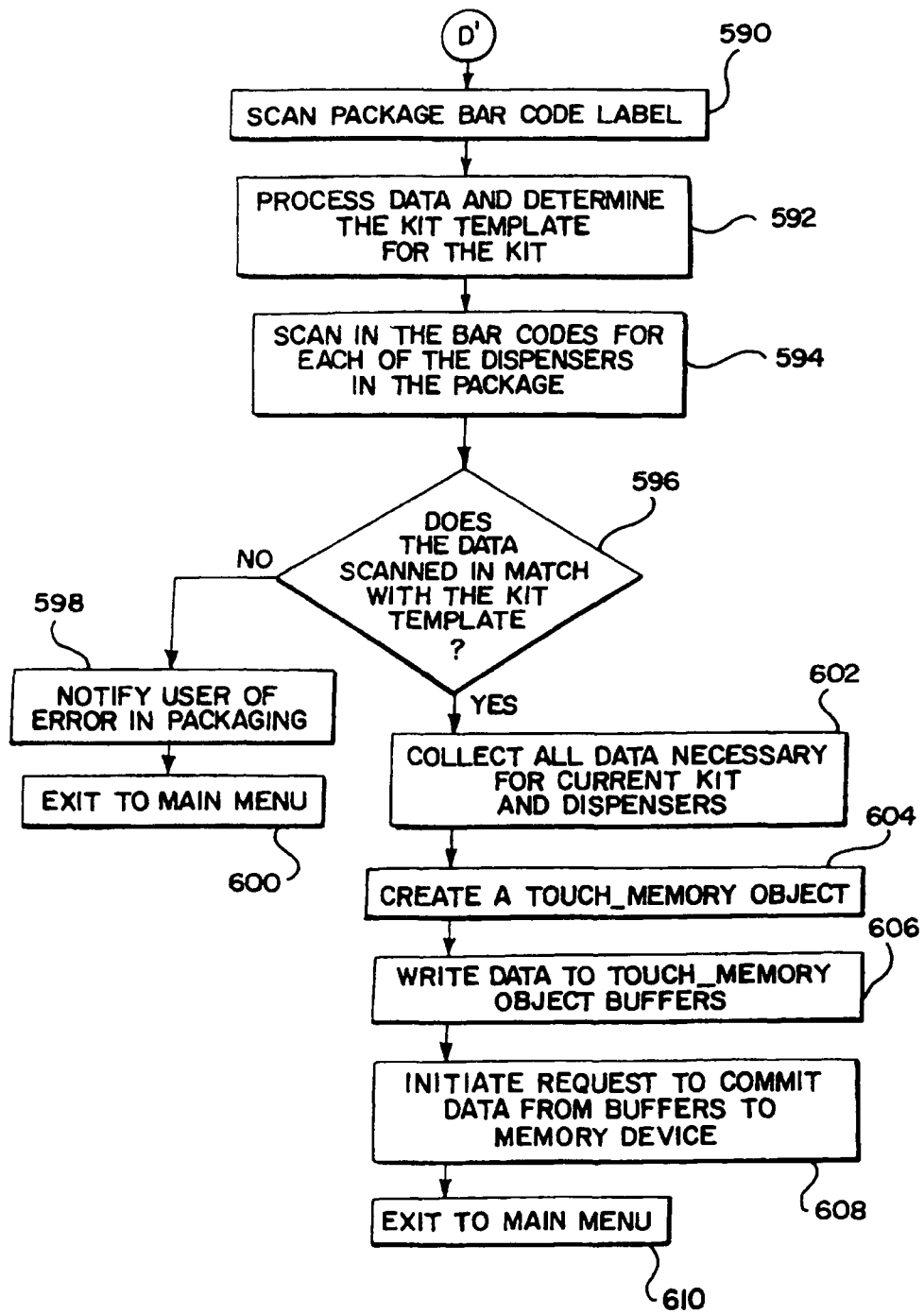

The updating the master lot and entering data into the memory device is shown in the flow chart in FIG. 22. The master lots form supports assignment of master lot numbers to predefined kits, as well as lot numbers and expiration dates to each of the dispensers in the kit. The expiration date of the kit is the earliest of the expiration dates of the dispensers in that kit. If the operator wishes to update the master lot 570, the manufacturing database determines if the master lot is old or new 572. If new, the list of kits is displayed 574 and a blank template for the user selected kit 576. If old, the previous master lots is listed 578 and the user selected master lot is displayed 580. Data is entered for the master lot 582 and then saved 584.

When the operator wishes to fill the memory device 588, in the preferred embodiment, the memory device 576 is an EPROM such as the Dallas Semiconductor DS1985 F5 16 Kbit add-only touch memory device. Other memory devices may be used to store the information and allow the end user to retrieve the information. First, the package bar code labels are scanned 590. A Welsh Allyn Scanteam 5400/5700 hand held scanner is used. The scanner need only be configured once to identify the hardware platform and bar code symbology. The scanner is programmed to send a T as a prefix character and also a T as a suffix character. The prefix is used to differentiate input from the scanner from input from the keyboard. The suffix is used to identify completion of acquisition.

Based on the information scanned from the package, the kit type is determined based on the information in the kit forms 592. The barcodes for each of the dispensers in the package is then scanned 594. Information in the kit form is compared with the information scanned in 596. For example, the number of dispensers in the package is checked. If the number is too high or too low, the user is notified and the memory device is not programmed. Further, if the type of the dispensers in the package does not match the type of dispensers in the kit form, the user is notified and the memory device is not programmed.

This is one of the methods to increase the quality control. If there was an error in the packaging of the package, (e.g., an incorrect dispenser was placed in the package), the user will be notified to correct the problem 598.

If the number and type of dispensers are correct, the database collects all data necessary for the current kit and dispensers 602. A touch_memory object is created which contains the form in which the memory will be stored 604. The data for the current kit and dispensers is written to the touch_memory object buffers 606. Finally, the touch_memory object buffers are transferred to the touch memory device 608. In order to program or read the touch memory device, a probe (Dallas Semiconductor DS9092GT) mounted in a hand held wand 514 is used. This wand 514 is attached to the serial port of the manufacturing computer 500 programming the touch memory device 516 through a Dallas Semiconductor DS9097 or DS9097E serial port (DB-25) adapter.

Figure 23:
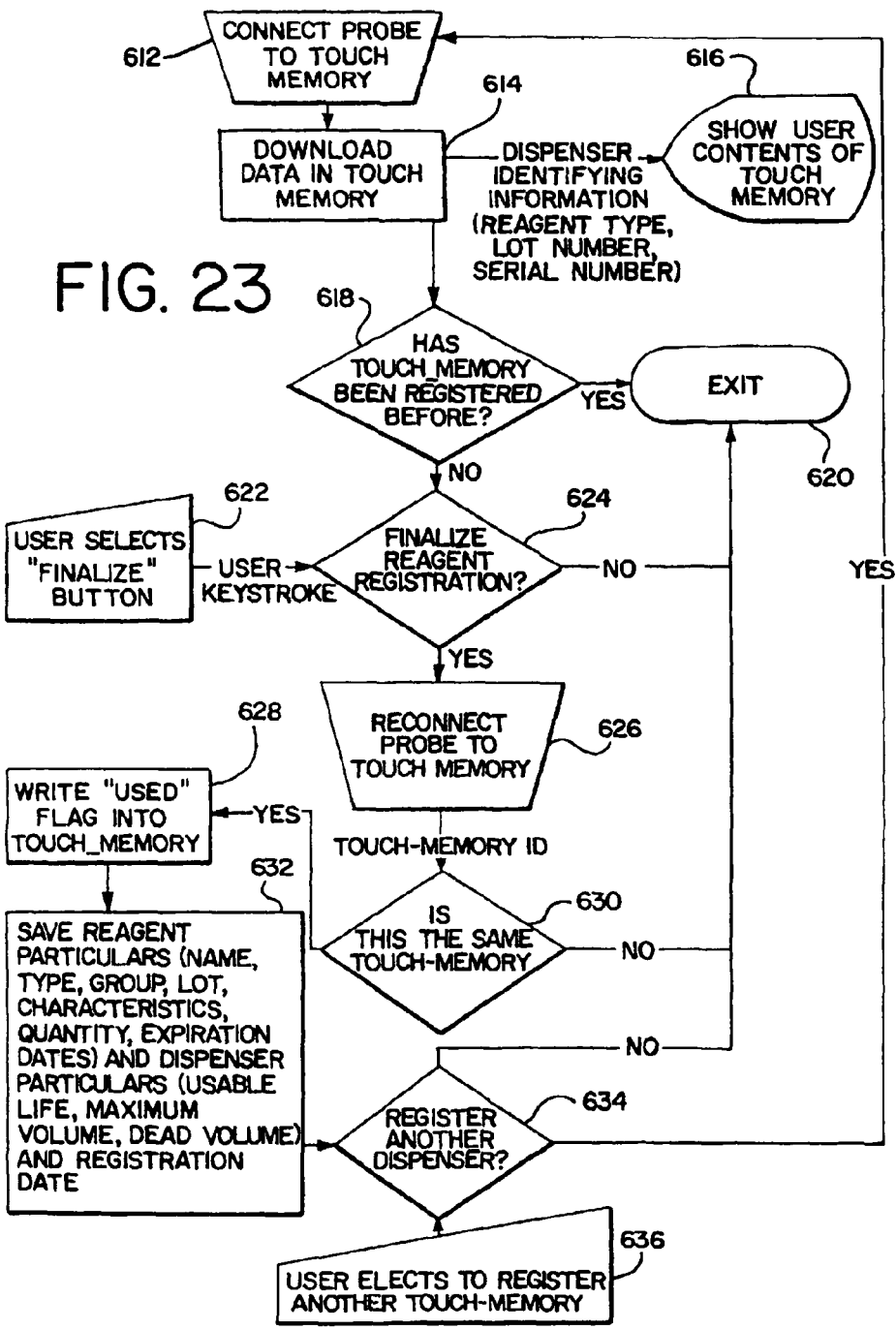
FIG. 23 is a flow chart for downloading data from a memory device to the host system.

At the end user, the kit or single dispenser is accompanied by the memory device. Referring to FIG. 23, there is shown a flow chart for downloading data from a memory device to the host system. The probe is first connected to the touch memory device 612. The contents of the touch memory device are downloaded to the host computer 614 and displayed to the user 616. It is then determined whether the touch memory device has been downloaded previously 618. This is done based on the contents of the touch memory device. If the memory contents were previously downloaded, a flag is set in the memory contents. Therefore, this kit has already been "used" and therefore should not be reprocessed. The user is prompted whether he or she wants to update the user's databases with the kit/dispenser data 624. If so, the probe is reconnected to the touch memory device 626, verified that it is the same touch memory device by comparing the current downloading with the previous download of data 630. The flag indicating that the touch memory device is "used" is set inside the memory device 628. In this manner, a memory device may be downloaded only once for purposes of security. The contents of the user's databases are updated with information contained in the touch memory device such as name, type, group, lot, characteristics, quantity, expiration dates for the reagents, and the usable life, maximum volume, dead volume and registration date for the dispenser 632.

Information in the touch memory device is used to update various tables contained in the user's database including the registration, receive and quality control tables for use by the operator. There are five different types of things that each have registration, receive and quality control tables: (1) antibodies; (2) reagents; (3) kits; (4) consumables and (5) control slides. Antibodies are chemicals that have living cells within which attach to the patient's tissue. Reagents are non-antibody chemicals which typically contain no living material. Kits, as described above, contain various combinations of dispensers. Consumables are materials such as the Liquid Coverslip™, wash buffer, etc. Each of these materials are regulated in different manners, thereby requiring different information contained within the registration, receive and quality control tables. For example, since antibodies are living material, they are regulated more highly and therefore require additional information in the tables.

The registration table contains the background information for the specific material. For example, the registration table contains the name of the material (antibody, reagent, kit, or consumable), the manufacturer, the clone number (antibody) and other information describing the material. This table is updated only when the material is first received. The receive table is a table which records each time when a certain material is received and the expiration date of that material as well as other information specific to this lot of material. Therefore, while the registration table may describe a specific antibody, the receive table will describe on which dates each dispenser of an antibody was received, the expiration date for the antibody, and the lot number. This information is used not only to generate reports which are required by regulation, but also to check for the expiration date of the chemical during a run, which is described subsequently. The quality control table records when a particular chemical was validated. Regulations require that when a new chemical or when a new lot for a previously received chemical is received, the lab must check to make sure the material performs in the expected manner (i.e., the material was processed correctly and not damaged in shipment). To determine if the material is "acceptable" to use in testing on patient tissue samples, end users have tissue that is known to test positive with undamaged reagents. The quality control table will track whether the chemical was tested for effectiveness and which tissue sample was used to test the chemical. In this manner, the tables, which are generated in large part by information from the touch memory, allow the end user to comply with regulation.

Other tables are used during a run which provides for better quality assurance in testing. For example, there is a dispenser table which contains, for each dispenser, the pertinent information for quality assurance during a run. For example, for each dispenser with a corresponding barcode, the table contains the expiration date, and the number of drops in the dispenser.

Figure 24A:
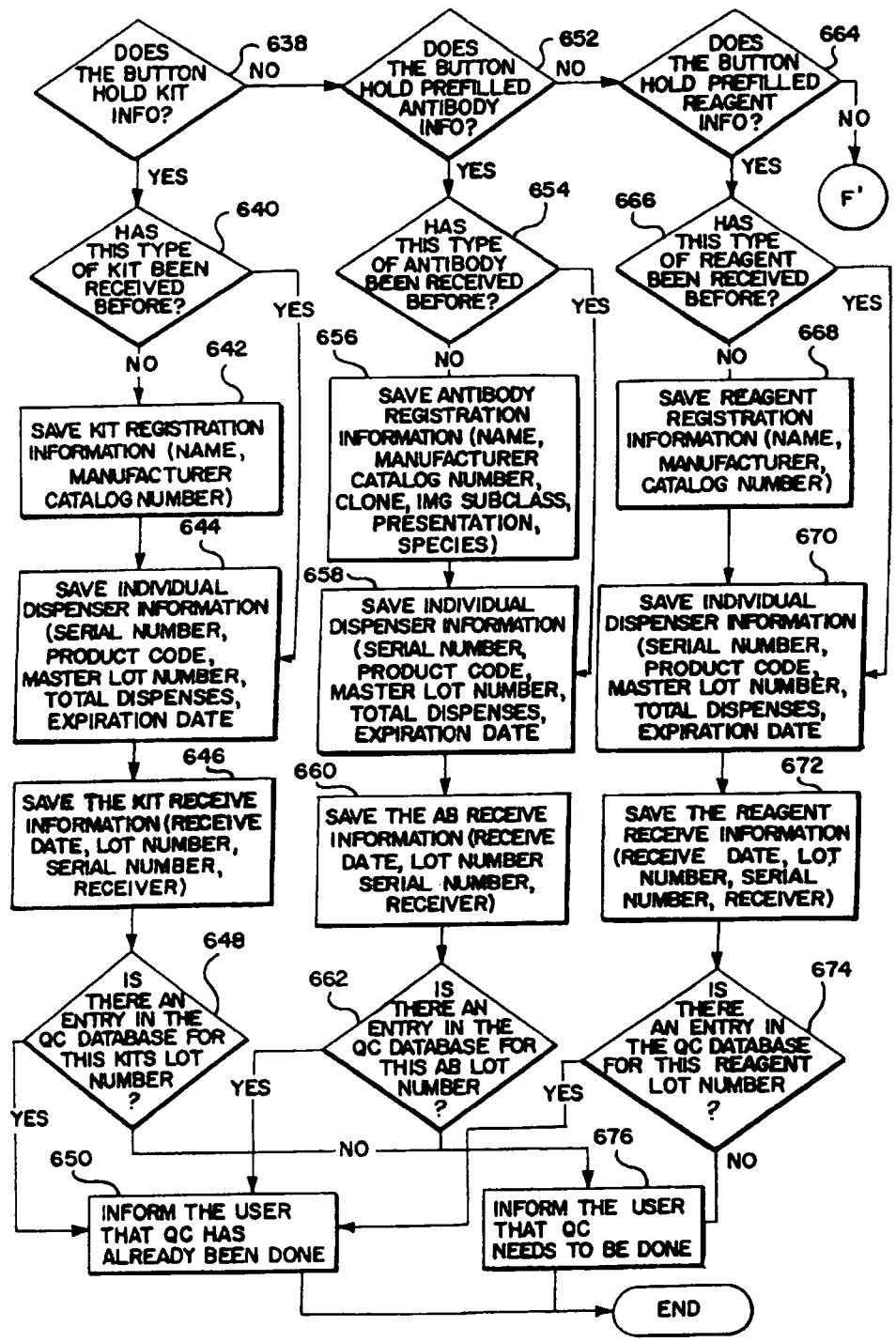
FIG. 24 is a flow chart for updating the memory devices of the user through information downloaded from an external memory device.
Figure 24B:
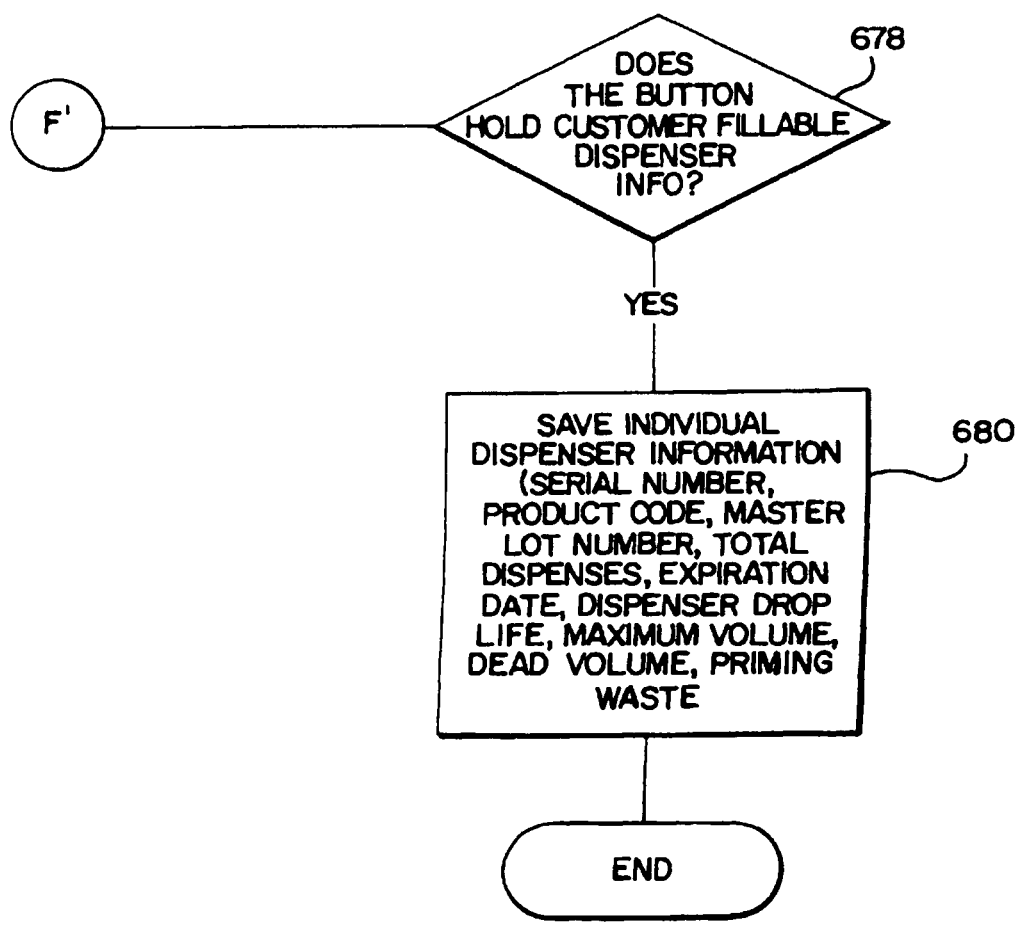

Referring to FIG. 24, there is shown a flow chart for updating the registration, receive and quality control tables on the host computer for use by the operator. Dispenser/kit information is read from the touch memory device. The computer determines if the touch memory device holds kit information 638. If so, the touch memory device searches the registration table to determine if the kit was previously received 640. If the kit was not received previously, the registration table must be updated with the kit registration information such as manufacturer and catalog number 642. The individual dispenser information within the kit is updated in the dispenser table including the serial number, product code, master lot number, total dispenses (by number of drops) and expiration date 644. The receive table is updated to include the receive date, lot number, serial number, and receiver 646. The quality control table is searched to determine if there is an entry in the table for this kit's lot number (i.e., if this is a new kit or a new kit lot number) 648. If the kit lot number has already been quality control tested, the user is informed that this has already been done 650. If not, the user is informed that a quality control test must be performed 676. In an alternative embodiment, a separate look-up table of known tissue samples used to test the effectiveness of a chemical received is archived. The known tissue samples are suggested to the user to test the effectiveness of the chemical received in order to update the quality control table.

The computer determines if the touch memory device holds prefilled antibody information 652. If so, the touch memory device searches the registration table to determine if the antibody information was previously received 654. If the antibody information was not received previously, the registration table must be updated with the antibody registration information such as name, manufacturer, catalog number, clone, 1 mg subclass, presentation, and species 656. The individual dispenser information is updated in the dispenser table including the serial number, product code, master lot number, total dispenses (by number of drops) and expiration date 658. The receive table is updated to include the receive date, lot number, serial number, and receiver 660. The quality control table is searched to determine if there is an entry in the table for this antibody lot number (i.e., if this is a new antibody or a new antibody lot number) 662. If the antibody lot number has already been quality control tested, the user is informed that this has already been done 650. If not, the user is informed that a quality control test must be performed 676.

The computer determines if the touch memory device holds prefilled reagent information 664. If so, the touch memory device searches the registration table to determine if the reagent information was previously received 666. If the reagent information was not received previously, the registration table must be updated with the reagent registration information such as name, manufacturer, and catalog number 668. The individual dispenser information is updated in the dispenser table including the serial number, product code, master lot number, total dispenses (by number of drops) and expiration date 670. The receive table is updated to include the receive date, lot number, serial number, and receiver 672. The quality control table is =searched to determine if there is an entry in the table for this reagent lot number (i.e., if this is a new reagent or new reagent lot number) 674. If the reagent lot number has already been quality control tested, the user is informed that this has already been done 650. If not, the user is informed that a quality control test must be performed 676.

The computer determines if the touch memory device holds customer fillable dispenser information 678. If so, the individual dispenser information is input including the serial number, product code, master lot number, total dispenses, expiration date, dispenser drop life, maximum volume, dead volume and priming waste 680. In an alternative embodiment, the user is prompted to input the amount of liquid, in milliliters is placed in the dispenser. This amount in milliliters is converted into a number of drops and stored in the table. The user may, at a later time, fill the user fillable dispenser and, at that later time, update the dispenser table with the amount of liquid put in the dispenser.

Figure 25:
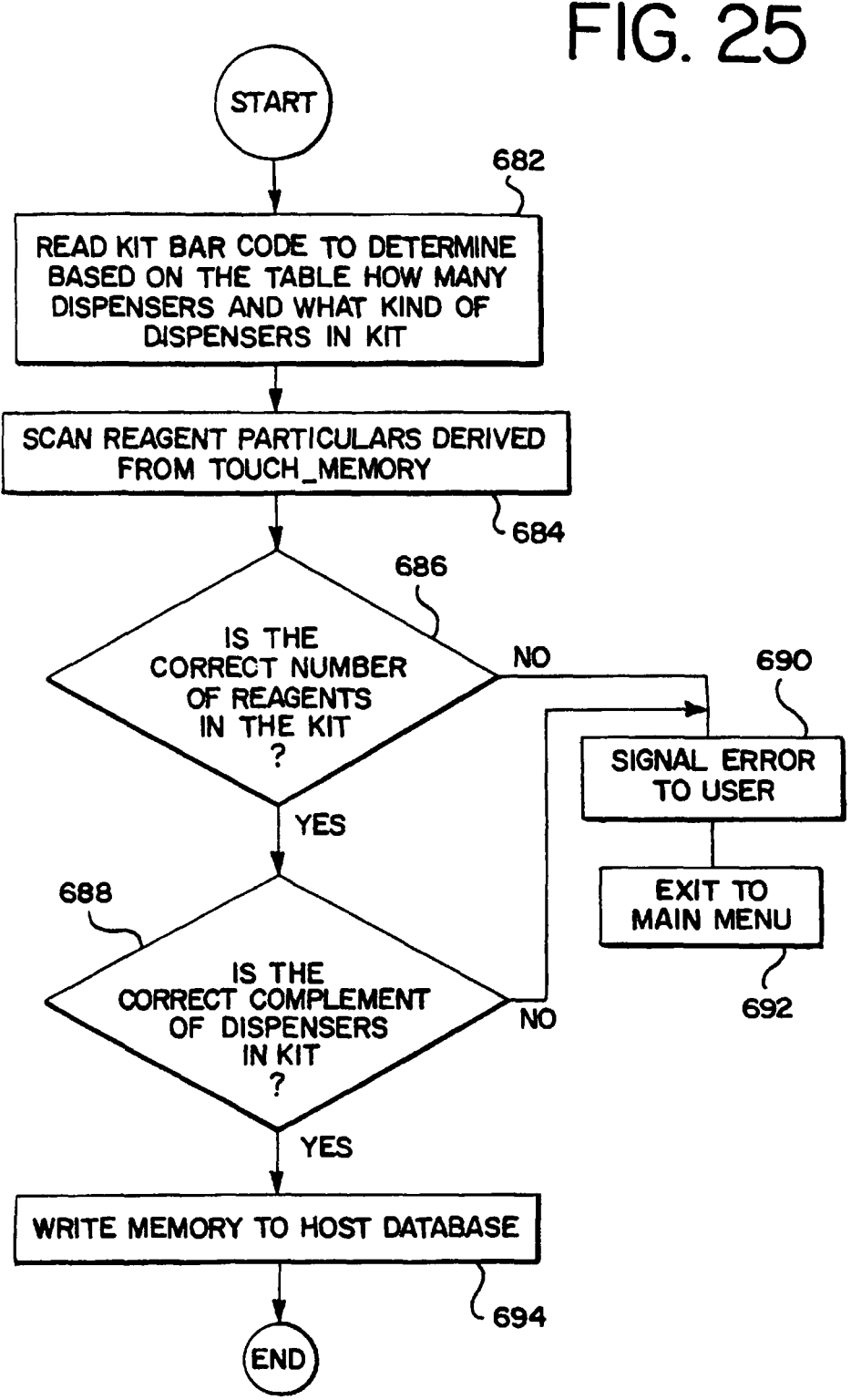
FIG. 25 is a flow chart for determining if the kit/dispensers for use by the operator is the correct number and correct complement.
Figure 26A:
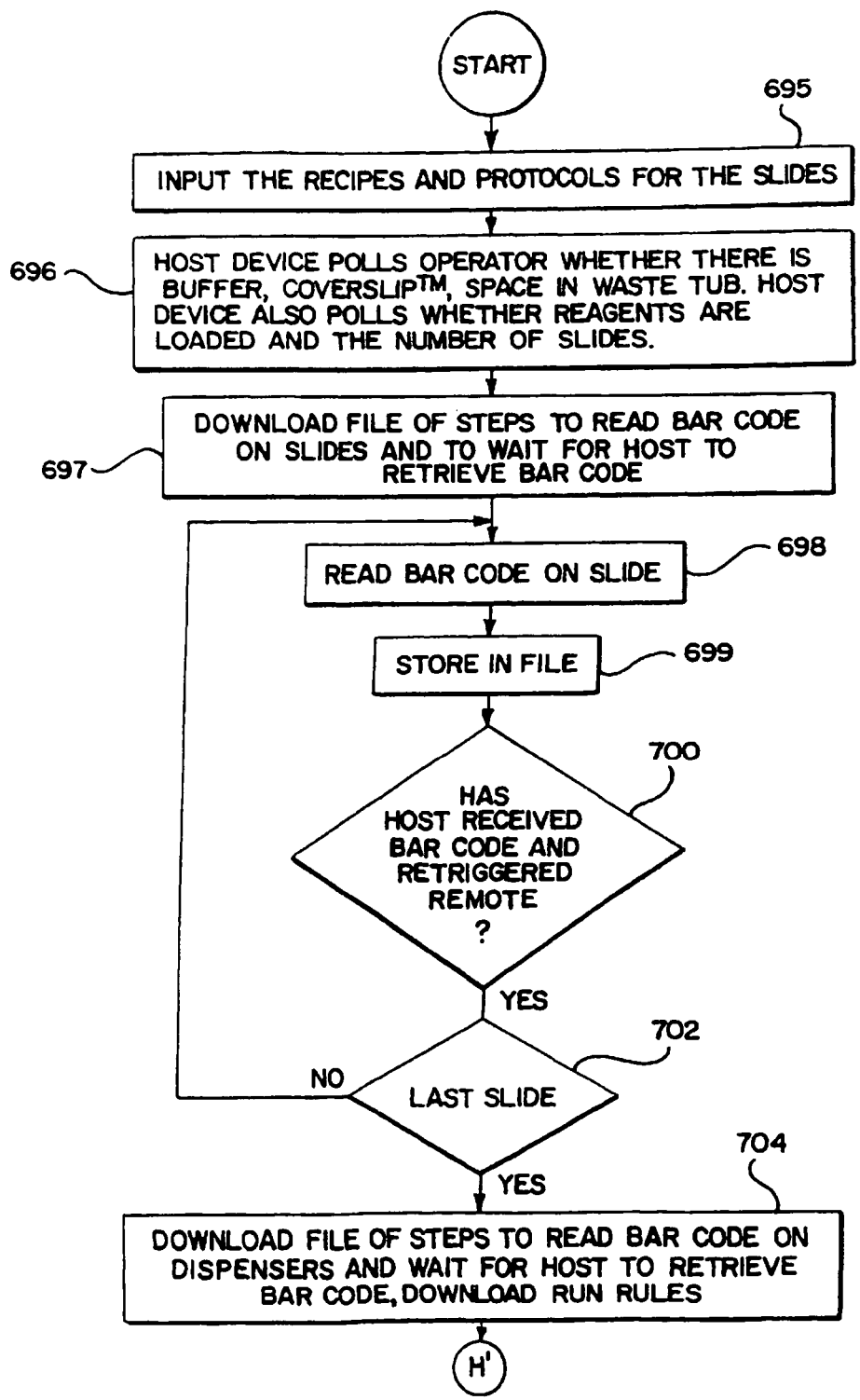
FIG. 26 is a flow chart of a preparation for a run using the dispense table.
Figure 26B:
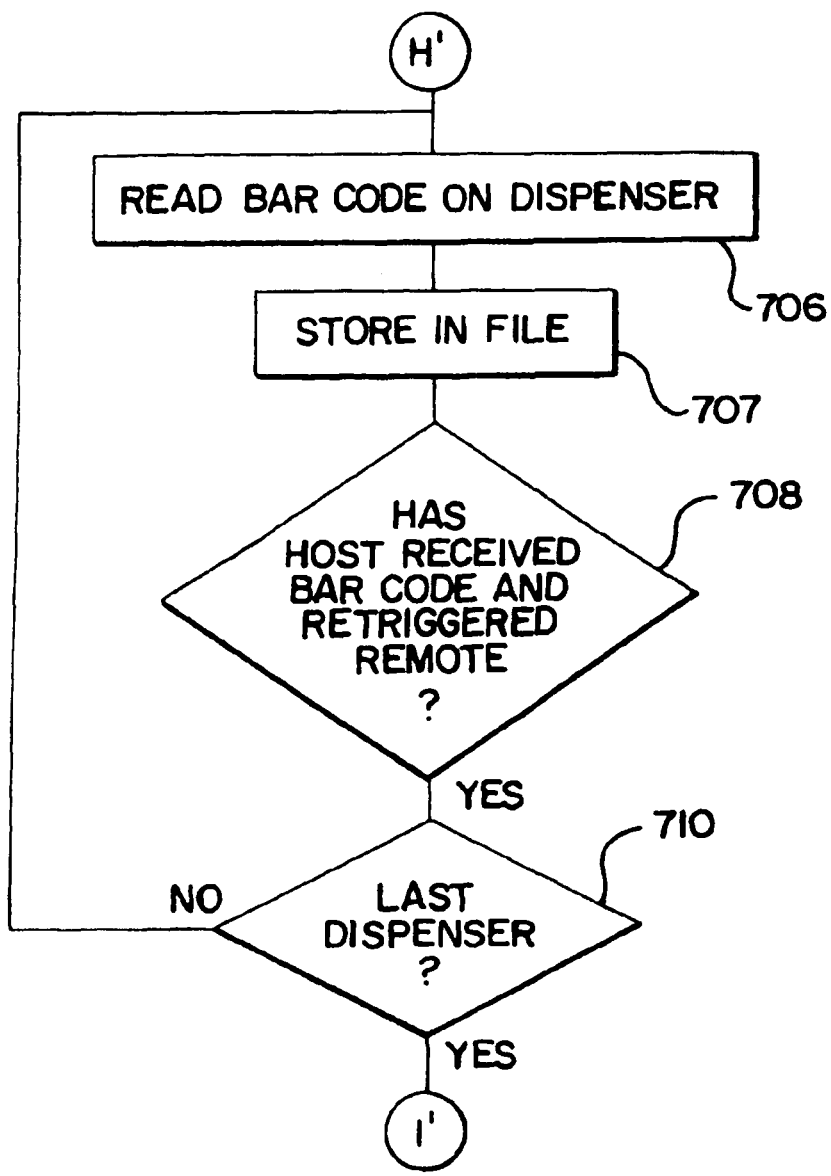
Figure 26C:
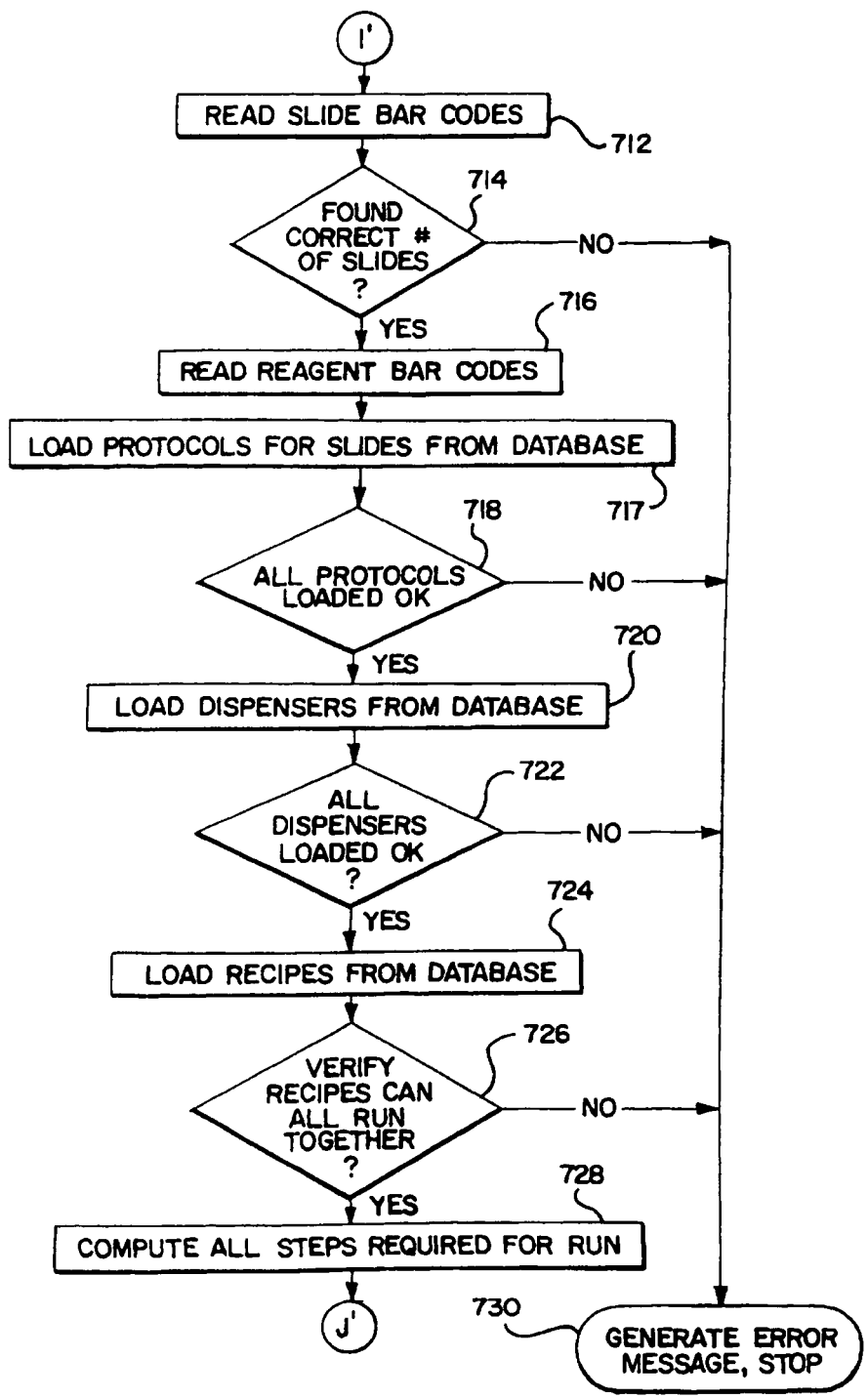
Figure 26D:
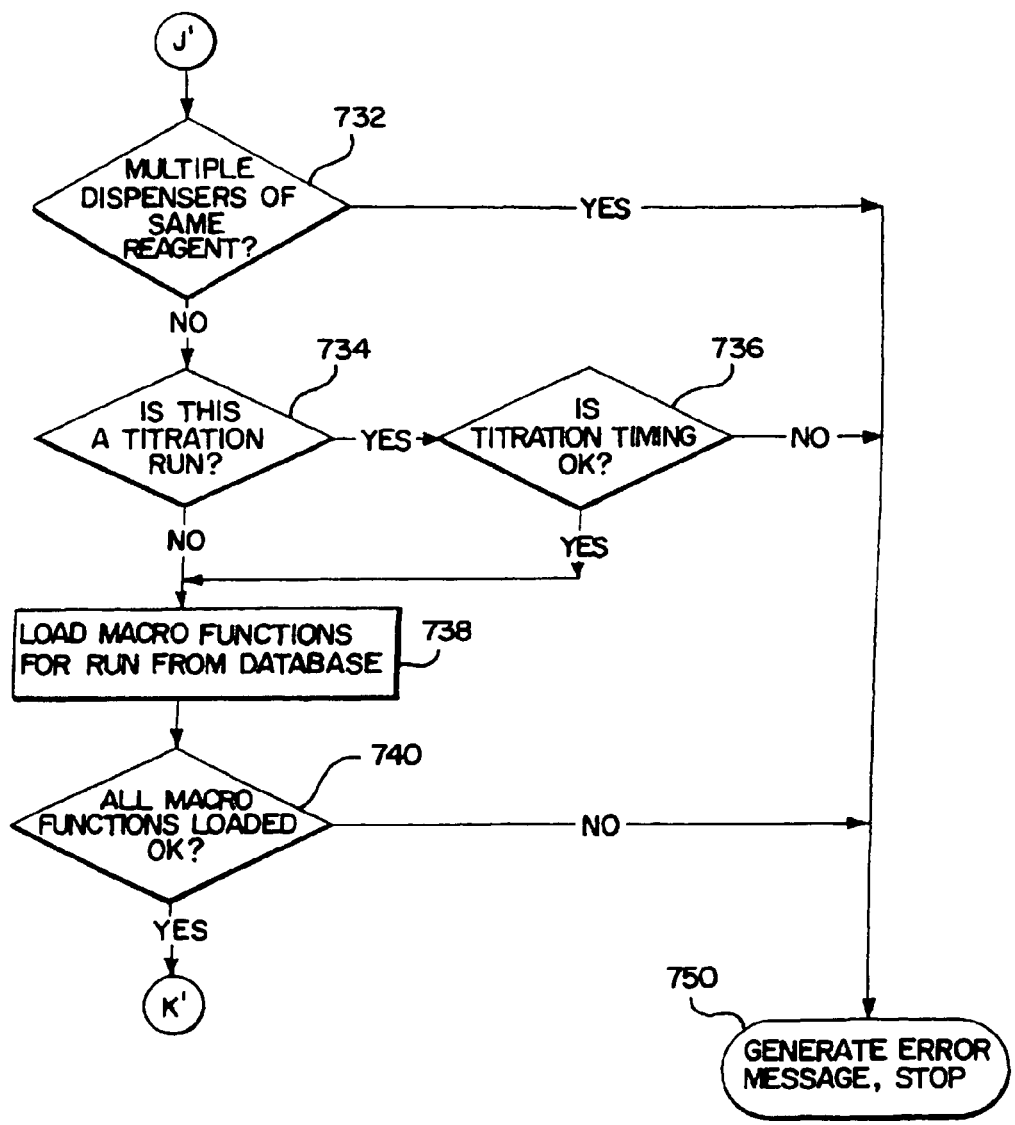
Figure 26E:
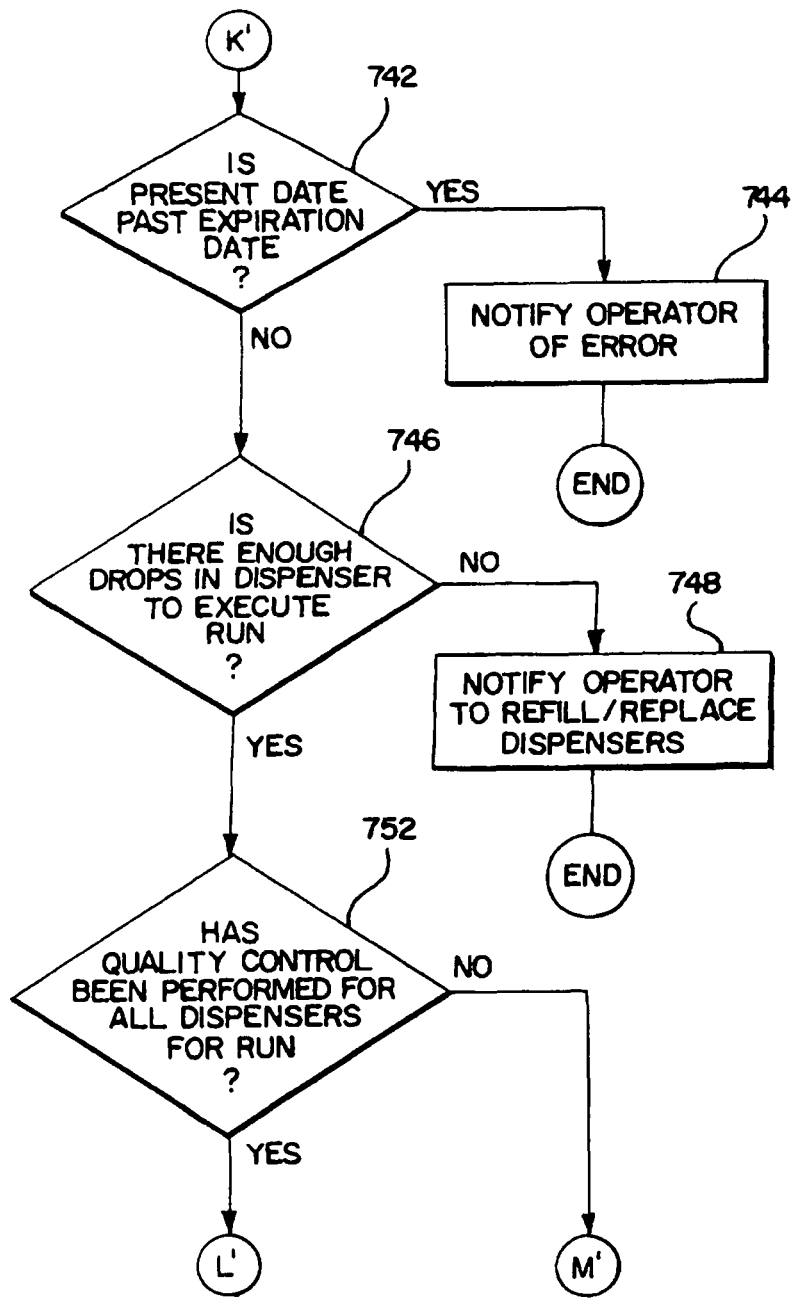
Figure 26F:
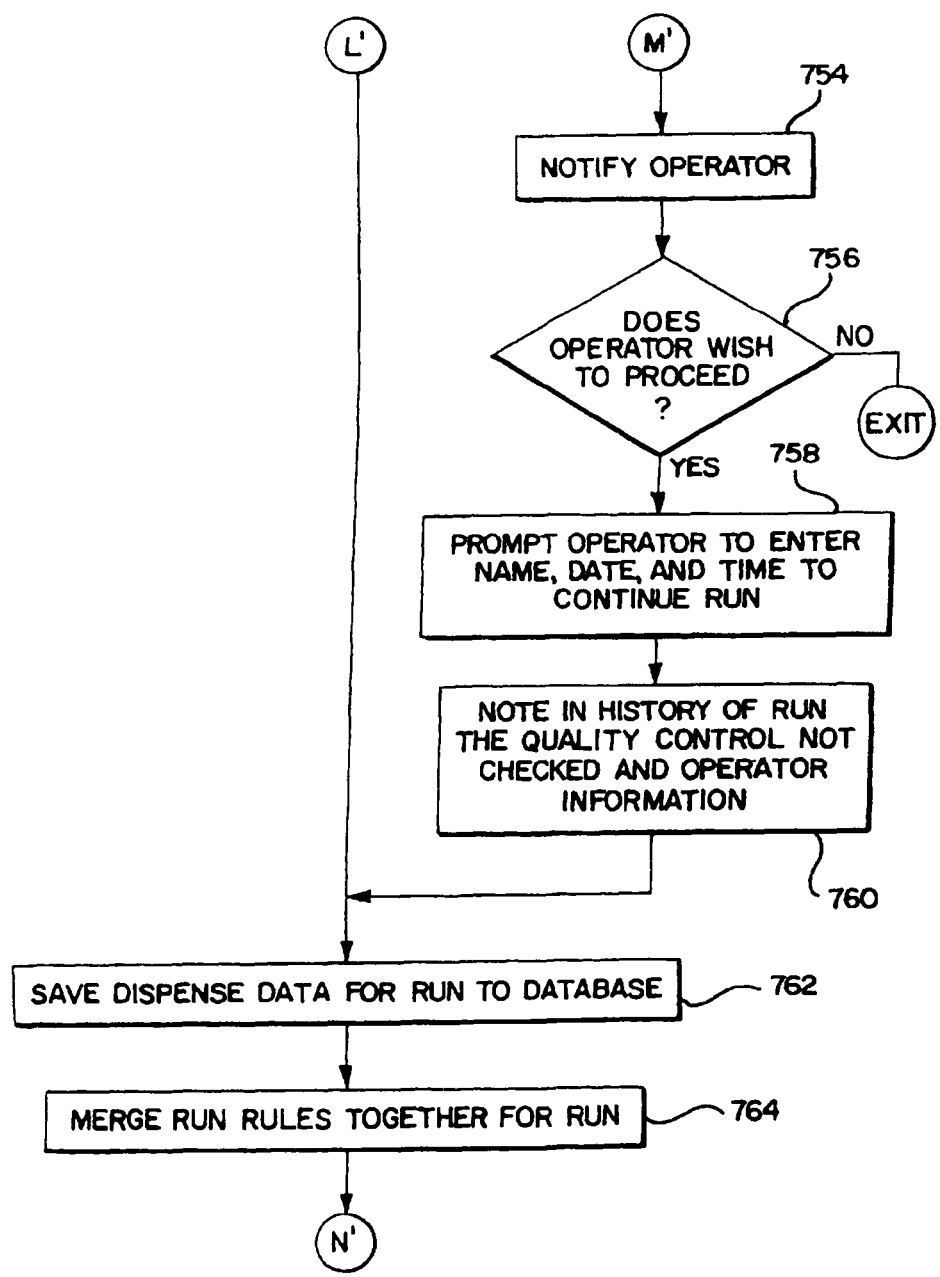
Figure 26G:
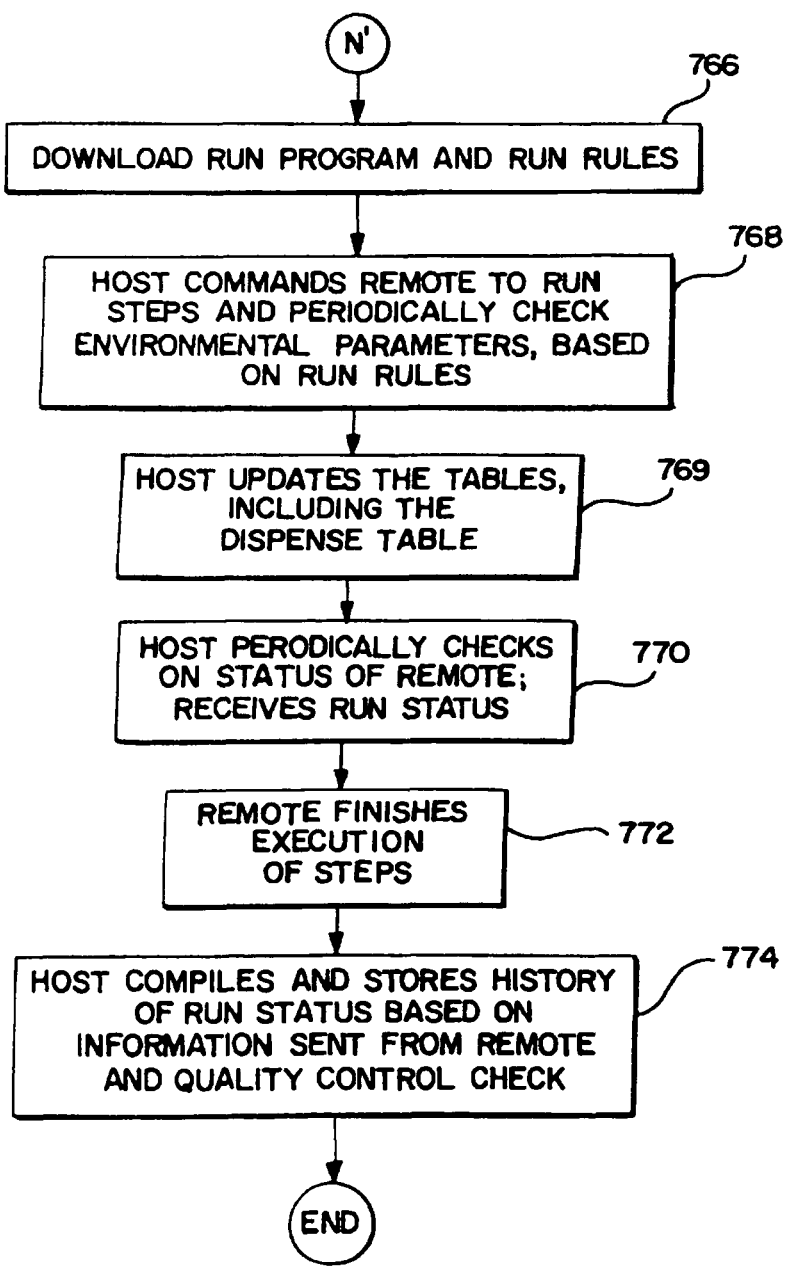

There are a series of checks using the information from the touch memory. Referring to FIG. 25, there is shown a flow chart for determining if the kit/dispensers for use by the operator is the correct number and correct complement, in an alternate embodiment of the invention. The kit barcode information from the touch memory is read to determine the type of kit and dispensers contained in the package 682, 684. Based on this barcode information, there is a look-up table which describes the number of reagents in the kit and the type or complement of reagents in the kit. This historical information in the look-up table is compared with what was actually sent in the package. If there is a discrepancy as to the number of dispensers in the kit or in the type of reagents in the kit 686, 688, the user is notified and the user's database is not updated with the kit barcode information 690. In this manner, the quality control may be increased by checking whether the proper dispensers were included in the kit.

After the downloading of the data, the host device 32 and remote devices 166 may execute a run. As described previously, the host device 32 and remote devices 166 are modular in design in that higher level system functions are handled by the host whereas the execution of the steps for staining is performed by the remote devices 166. This modularity of design utilizing a personal computer as a host device 32 is beneficial in several respects. First, the host computer can be used to start runs on other remote devices 166. Second, the host device 32 can periodically update the software more efficiently on the remote device 166 based on upgrades in the operating system. For example, the lowest level code in the remote devices 166, which handles the basic input and output for the remote device 166 and the execution of programs, may be updated based on changes in error messaging, changes in output device design (such as different types of valves), and changes in the messaging protocols between the host and the remote. Third, the modularity multiplies the number of staining modules which may be run by a single machine. Fourth, since the host device 32 is comprised, in the preferred embodiment, of a personal computer, the host machine may be easily upwardly compatible, as opposed to previous standalone staining modules. Further, the personal computer can be integrated with a network environment to integrate with other computers. For example, there is a trend in hospitals to standardize the computer hardware used and to interconnect the computer hardware. The host device 32 may be connected to a hospital network, receiving commands from other computers on the network to execute a staining run, described subsequently, or sending results of a run to another computer on the network. Fifth, the host device 32 may serve as a platform through which various staining modules may be integrated. For example, there are various types of staining modules, some which use dispensers versus vials, some which use horizontal slide trays versus vertical slide trays, etc. The host device 32 may be integrated with a variety of staining modules, downloading programs to the different modules, described subsequently, depending on the particular configuration of the module. Sixth, the remote devices 166, as a modular piece in the automated biological reaction system, may be serviced more easily. Instead of having a large machine dedicated to staining, the remote device 166 is smaller and can be shipped through the mail easily. In this manner, when an end user has difficulty with a remote device 166, the user may receive a second remote device through the mail, and send the faulty remote device back to be fixed. Therefore, the user need not rely on on-site maintenance for the remote device, and the attendant cost associated with on-site maintenance.

The host may execute three different types of runs. The first run is a test run, which is described subsequently. The second run is a system run, whereby the remote device 166 reads the barcodes for the slides or the dispensers, or other non-staining functions required to setup a staining run. The third run is a staining run whereby the remote device 166 stains the slides. The second and third runs are described in FIG. 26. When executing a run, the host downloads a sequence of steps in a run program to the remote device 166. The run program is comprised of two separate pieces: (1) a main program (defined as macro 0); and (2) subroutines (defined as macros 1-255). The main program is can be composed of, but not limited to, calls to the subroutines. Therefore, the entire length of the run program through calls to subroutines is less than a line by line execution of the entire program. For example, if a subroutine is called 50 times, the main program calls the subroutine 50 times rather than downloading a program which includes the code for the subroutine 50 times. In addition, the subroutines are defined by a programming language of thirty-one low-level commands which perform basic functions on the remote such as checking the timer, turning on an output such as a valve or a heater, or moving the carousel. When downloading the run program, the macros are downloaded as needed to execute a single run.

In addition to downloading a run program, the host device 32 downloads the sensor monitoring and control logic called the run rules. This program is made up of a series of continuous checks that must be done during the execution of the run program. As discussed previously, one of the checks is the upper and lower limit of the temperature of the slides. If, during a run, the environmental temperature is below the lower limit, as indicated by slide temperature monitoring sensor, the slide heater is turned on. Likewise, if the environmental temperature is above the upper limit, as indicated by slide temperature monitoring sensor, the slide heater is turned off. Another run rule relates to the opening of a system door. Additional run rules relate to the environment in which the remote device 166 executes the run. If any of the sensors are outside of the boundaries sent by the run rules, the remote device 166 sends a message which is retrieved by the host device 32. As discussed generally in FIG. 5C with respect to placing messages in the queue, the first priority is the execution of the steps in the run program. In addition to this, where spare processing is available, the host device 32 polls the remote device 166 for status. The host device 32 does this approximately every 1½ seconds to receive the status of the remote device 166 including the current temperature of the remote device 166, current step number being processed in the run program, elapsed time of the run, and any errors during the run. The host makes a record of any anomalies during the remote device run and prints the final report at the end of the run.

An example of a staining run is shown in flow chart form in FIG. 26. The first run is a system run to read the barcode on the slides. In executing this run, the host device 32 downloads a run program and the run rules 696. The remote device reads a barcode 698, stores the barcode in a file 699 to be used subsequently, then waits for the host to retrieve the barcode and retrigger the remote to read another barcode on the slide 700. The remote device 166 does this until the last slide is read 702. The host then downloads the run program and run rules for the second system run, which concerns the reading of the barcodes on the dispensers 704. Similar to the first system run, the remote device 166 reads a barcode 706, stores the barcode in a file 707 to be used subsequently, then waits for the host to retrieve the barcode and retrigger the remote to read another barcode on the dispenser 708. The remote device 166 does this until the last dispenser is read 710.

The host device 32 then reads the slide bar codes already stored in the file 712. If the number of entries is the file is different from the number previously entered by the operator, an error message is generated 730. This is done since the barcode reader, at times, may not read one of the barcodes on the slide. In that case, the run is stopped. The host device then reads the barcodes for the reagents already stored in the file 716. Based on the barcodes, the host device loads the protocols for the slides from the database. In order to simplify the procedure, each barcode on a slide is standardized. For example, if the staining for the slide is to test for prostate cancer, a particular barcode is placed on that slide which is used for every slide which is to be tested for prostate cancer. For each specific test, there are a series of macros which are to be executed by the remote device 166. In the case of the test for prostate cancer, a look-up table indicates the series of steps or macros corresponding to the particular barcode designated as a test for prostate cancer. As discussed previously, there are macros from 1 to 255 which define basic operations of the remote device 166. For the specific task of testing for prostate cancer, the look-up table includes all the necessary macros, in the proper sequence, to perform the test. Based on these macros, the host device 32 determines the types of reagents and amount of drops required to execute the steps 714. Moreover, in creating the run program, calls to the macros are included in macro 0 and macros 1-255 which are to be called are included after macro 0. The protocols correspond to the user defined options for a particular staining run. In the case of the example for testing for prostate cancer, the options include the type of reagents, the number of drops, etc. All the protocols are loaded and determined if they exist in the database. If so, the host device loads data from the dispense table 720 and determines if all of the dispensers are present and loaded 722. If so, the recipes are loaded from the database 724. In contrast to the protocols, the recipes define steps which the user does not control. For example, turning on valves, heating the slides, etc. are operations which the users cannot alter. The host device 32 then verifies that the recipes can be run together 726. For example, if there are two recipes which dictate the temperature of the slides (where the slides are in close proximity), and the temperatures are different, the two recipes cannot be executed; therefore, and error message is generated 730. The steps for the run is then computed 728. Because there are several slides being tested at the wheel at once, and each slide has a series of steps associated with it, the host device generates the run program which can execute all the steps for all of the slides. The host device is constrained by being able, for example, to mix with the vortex mixers at a certain station on the slide carousel, to dual rinse at a certain station, to add the volume adjust, etc. Based on these constraints, the run program is generated which tells the remote to execute the steps in the proper sequence at the proper station 728.

The host device determines if there are multiple dispensers of the same reagent 732. If so, an error message is generated since, for quality control purposes, dispensers from the same kit may only be used in a run. The host device then determines if this is a titration run 734. In a user filled dispenser, the user may wish to test varying concentrations of reagent in the liquid dispenser. If so, the user executes a titration run whereby the user is allow, via the program, to stop the run in the middle and titrate different concentrations. The amount of time for the titrations must be short enough so that the slide will not dry out 736. Otherwise, an error message is generated 750. The macro functions are loaded from a database for the run 738 and determined if all the macro functions loaded properly 740. The host device 32 determines, based on the dispenser table, whether any of the dispensers are past the expiration date 742. If so, the operator is notified 744. Similarly, the dispenser table is checked to determine if the dispensers have sufficient liquid to conduct the run 746. If not, the operator is notified to refill or replace the dispensers 748. Optionally, quality control can be checked to determine if all of the dispensers have been tested under quality control protocols 752.

Therefore, the host device 32 looks up in the dispenser table 716, described in FIG. 24, to determine if the reagents necessary (1) are past their expiration date; (2) are present to perform the run; (3) have enough drops in the dispensers to execute the run; or, optionally, (4) have been tested for quality control. If any of the first three conditions fail, the run cannot be executed and the operator is notified (i.e., one of the dispensers is past its expiration date, one of the dispensers is missing, or one of the dispensers is low on liquid).

Optionally, for quality control purposes, the dispenser table is searched to determine if quality control was performed on the dispenser 752. If it has not yet performed, the operator is notified 754 and asked if he or she wishes to proceed 756. If the operator wishes to proceed, he or she must enter his or her name, the date and time in order to continue the run 758. Finally, when the run is executed, the information entered by the operator is included in the history of the run, described previously, to indicate that at least one of the dispensers had not been tested in compliance with the regulations, but that the run was performed anyway 760. In this manner, the quality of the run may be increased due to monitoring of the dispensers used in the testing of the tissue samples. The host device 32 then saves the dispense data for the run to a database 762 and merges the run rules, which determine the operating environment of the run, together for the run 764. The host device 32 downloads the run program and the run rules for the current staining procedure 766. The host device 32 commands the remote to run the steps and to run the checks or the run rules 768. As discussed previously, the host device 32 periodically checks the status of the remote device 770. After the remote device 166 finishes execution of the run program 772, the host device 32 compiles the history of the run and stores the information sent from the remote 774.

The host device 32 also communicates with the remote devices 166 by reading and writing information regarding the operation of the remote devices 166. For example, the host device 32 downloads a command indicating to the remote device the amount of time (in 10's of milliseconds) the valve 248G for the volume adjust line is on. This value is stored in non-volatile RAM on the remote device 166. Further, the host device 32 may poll the remote device to send its stored value for the volume adjust time stored in non-volatile RAM. Other information, such as the slide temperature monitoring sensor 68, buffer heater temperature sensor 66 and system pressure transducer 290, as described in FIG. 6A, may be read by the host device 32 and may be calibrated by the host device 32. When reading the sensor information from the remote device 166, the current calibration data is sent back to the host. Calibration data is used to adjust for constant errors inherent in each temperature sensor and pressure transducer. In order to correct for errors, the host device writes to the remote. For example, when calibrating the pressure sensor, the host device 32 commands the remote device to perform span calibration of the system pressure transducer 290 at the preset pressure of 13.0 psi. The remote device 166 registers the current raw pressure as the 13.0 psi analog to digital point.

Figure 27:
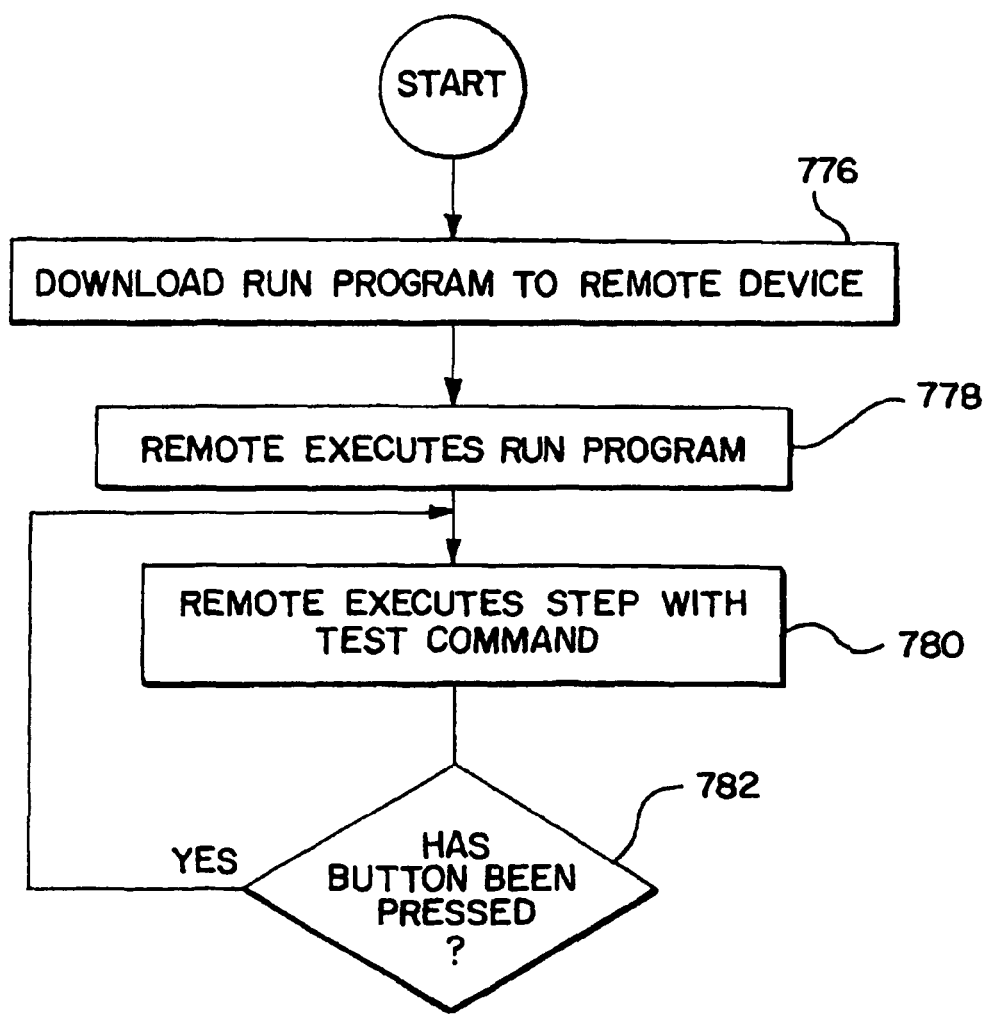
FIG. 27 is a flow chart of the testing run for the remote device.

Referring to FIG. 27, there is shown a flow chart of the testing run for the remote device. One of the commands or steps downloaded to the remote device is a test command 776. The remote processes the commands in the run program 778 until the remote device 166 receives the test command 780. The remote device 166 then waits until a button 295 is pressed on the remote device 782, as described in reference to FIG. 6A. When the button 295 is pressed, the remote device executes the previous command, and then waits for the button 295 to be depressed again. In this manner, the operator may test individual steps or commands by pressing the button 295 and re-executing the previous command. In an alternative embodiment, the remote device interprets the test mode as a means by which to single step through the program. Every time the button 295 is pressed, the remote device 166 executes a command. In this manner, the operator may step through the run program and determine if there are any errors in the sequence of steps.

From the foregoing detailed description, it will be appreciated that numerous changes and modifications can be made to the aspects of the invention without departure from the true spirit and scope of the invention. This true spirit and scope of the invention is defined by the appended claims, to be interpreted in light of the foregoing specification.

We claim:

1. An automated biological reaction system, comprising:
   at least one dispenser for applying a reagent to a sample undergoing a reaction in the automated biological reaction system;
   a reagent memory device accompanying the at least one dispenser, the reagent memory device containing data for a reagent used in the automated biological reaction system, wherein the data includes expiration date information for the reagent;
   a host device comprising a processor and a host memory device connected to the processor, the host memory device including a reagent table;
   a device that is used to transfer the data in the reagent memory device to the host memory device; and
   a flag in the reagent memory device that indicates whether memory contents of the reagent memory device were previously downloaded,
   wherein, upon said transfer, the flag is set in the reagent memory device indicating said memory contents were previously downloaded,
   and wherein the processor updates the reagent table in the host memory device.

2. The system as claimed in claim 1, wherein the device used to transfer the data in the reagent memory device writes in the reagent memory device that the memory contents of the reagent memory device has been transferred to the host memory device by setting the flag.

3. The system as claimed in claim 1, wherein the device includes a probe mounted in a wand and an adapter coupled to the wand.

4. The system as claimed in claim 1, wherein the device includes a probe mounted in a wand.

5. The system as claimed in claim 1, wherein the data for the reagent comprises any of a reagent type, a name, a lot number, a group, a quantity, characteristics, and a reagent serial number.

* * * * *